(12) United States Patent
Chan et al.

(10) Patent No.: US 10,894,149 B2
(45) Date of Patent: Jan. 19, 2021

(54) DILATION CATHETER ASSEMBLY WITH ADJUSTMENT FEATURES

(71) Applicant: Acclarent, Inc., Irvine, CA (US)

(72) Inventors: Randy S. Chan, San Jose, CA (US); John Anastasiadis, Tinton Falls, NJ (US); Samantha M. Weber, Somerville, NJ (US); Ketan P. Muni, San Jose, CA (US); Don Q. Ngo-Chu, Irvine, CA (US)

(73) Assignee: Acclarent, Inc., Irvine, CA (US)

( * ) Notice: Subject to any disclaimer, the term of this patent is extended or adjusted under 35 U.S.C. 154(b) by 733 days.

(21) Appl. No.: 15/440,415

(22) Filed: Feb. 23, 2017

(65) Prior Publication Data

US 2017/0259043 A1 Sep. 14, 2017

Related U.S. Application Data

(60) Provisional application No. 62/305,008, filed on Mar. 8, 2016.

(51) Int. Cl.
*A61M 25/10* (2013.01)
*A61M 25/09* (2006.01)
(Continued)

(52) U.S. Cl.
CPC ......... *A61M 25/1025* (2013.01); *A61B 17/24* (2013.01); *A61M 25/0113* (2013.01);
(Continued)

(58) Field of Classification Search
CPC .......... A61M 25/0053; A61M 25/0141; A61M 25/1025; A61M 25/0113; A61M 25/09;
(Continued)

(56) References Cited

U.S. PATENT DOCUMENTS 7,630,676 B2 12/2009 Pirwitz
9,155,492 B2 10/2015 Jenkins et al.
(Continued)

FOREIGN PATENT DOCUMENTS

| EP | 2977073 A2 | 1/2016 |
| WO | WO 2011/002854 A1 | 1/2011 |
| WO | WO 2017/034705 A1 | 3/2017 |

OTHER PUBLICATIONS

U.S. Appl. No. 15/278,588, filed Sep. 28, 2016.
(Continued)

*Primary Examiner* — Manuel A Mendez
*Assistant Examiner* — Justin L Zamory
(74) *Attorney, Agent, or Firm* — Frost Brown Todd LLC

(57) ABSTRACT

A dilation catheter system includes a body, a guidewire, and a dilation catheter having an elongate shaft. The dilation catheter system may include a locking mechanism to prevent the guidewire from moving relative to the elongate shaft or to lock the guidewire to the dilation catheter to form a fixed wire unit. The dilation catheter system may include a stabilizing tube extending from an actuator, to provide rigidity to the guidewire. The dilation catheter may include a grip element having a plurality of grip features disposed thereon. The dilation catheter may include a cap biased toward a first longitudinal position and movable to a second longitudinal position. A guide catheter secured to the cap is prevented from changing angular orientation in the first longitudinal position and is free to change angular orientation in the second longitudinal position.

20 Claims, 44 Drawing Sheets

(51) Int. Cl.

| | |
|---|---|
| *A61B 17/24* | (2006.01) |
| *A61M 29/02* | (2006.01) |
| *A61M 25/01* | (2006.01) |
| *A61B 17/00* | (2006.01) |
| *A61M 25/06* | (2006.01) |
| *A61B 17/22* | (2006.01) |
| *A61M 25/00* | (2006.01) |

(52) U.S. Cl.
CPC ...... *A61M 25/09* (2013.01); *A61M 25/09041* (2013.01); *A61M 29/02* (2013.01); *A61B 2017/00331* (2013.01); *A61B 2017/00389* (2013.01); *A61B 2017/00424* (2013.01); *A61B 2017/00473* (2013.01); *A61B 2017/22038* (2013.01); *A61B 2017/22049* (2013.01); *A61M 25/0041* (2013.01); *A61M 2025/0681* (2013.01); *A61M 2025/09116* (2013.01); *A61M 2025/09125* (2013.01); *A61M 2210/0618* (2013.01); *A61M 2210/0681* (2013.01)

(58) Field of Classification Search
CPC ........ A61M 25/09041; A61M 25/0041; A61M 2025/0681; A61M 2025/09116; A61M 2025/09125; A61B 17/24; A61B 2017/00331; A61B 2017/00389; A61B 2017/00424; A61B 2017/00473; A61B 2017/22038; A61B 2017/22049
See application file for complete search history.

(56) References Cited

U.S. PATENT DOCUMENTS

| | | | |
|---|---|---|---|
| 9,554,817 | B2 | 1/2017 | Goldfarb et al. |
| 2001/0025134 | A1* | 9/2001 | Bon .................. A61M 25/0136 600/146 |
| 2005/0126469 | A1* | 6/2005 | Lu ....................... A61M 15/009 116/307 |
| 2010/0030031 | A1 | 2/2010 | Goldfarb et al. |
| 2010/0312101 | A1* | 12/2010 | Drontle ................. A61B 17/24 600/424 |
| 2011/0004057 | A1 | 1/2011 | Goldfarb et al. |
| 2012/0071856 | A1* | 3/2012 | Goldfarb ............... A61M 29/00 604/514 |
| 2013/0261388 | A1* | 10/2013 | Jenkins ................ A61B 1/0014 600/104 |
| 2013/0274715 | A1 | 10/2013 | Chan et al. |
| 2014/0074141 | A1 | 3/2014 | Johnson et al. |
| 2015/0224298 | A1 | 8/2015 | Albritton, IV et al. |
| 2015/0374963 | A1 | 12/2015 | Chan et al. |
| 2016/0058985 | A1 | 3/2016 | Lam et al. |
| 2017/0056632 | A1 | 3/2017 | Jenkins et al. |

OTHER PUBLICATIONS

U.S. Appl. No. 62/305,008, filed Mar. 8, 2016.
U.S. Appl. No. 62/305,083, filed Mar. 11, 2016.
International Search Report and Written Opinion dated Aug. 14, 2017 for International Application No. PCT/US2017/021301, 17 pages.

* cited by examiner

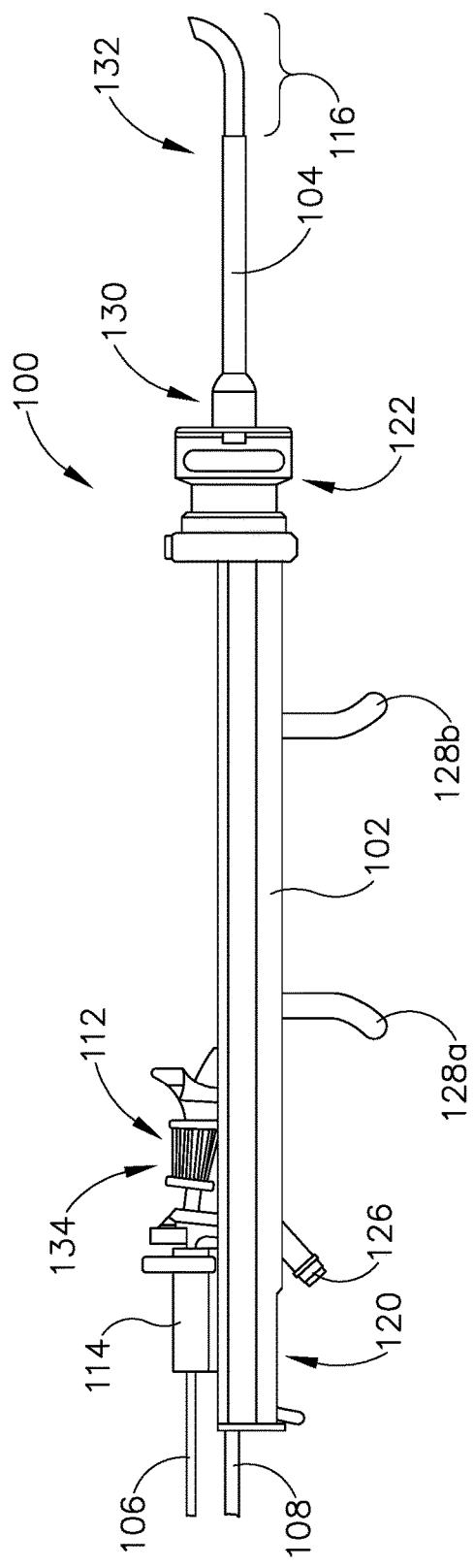
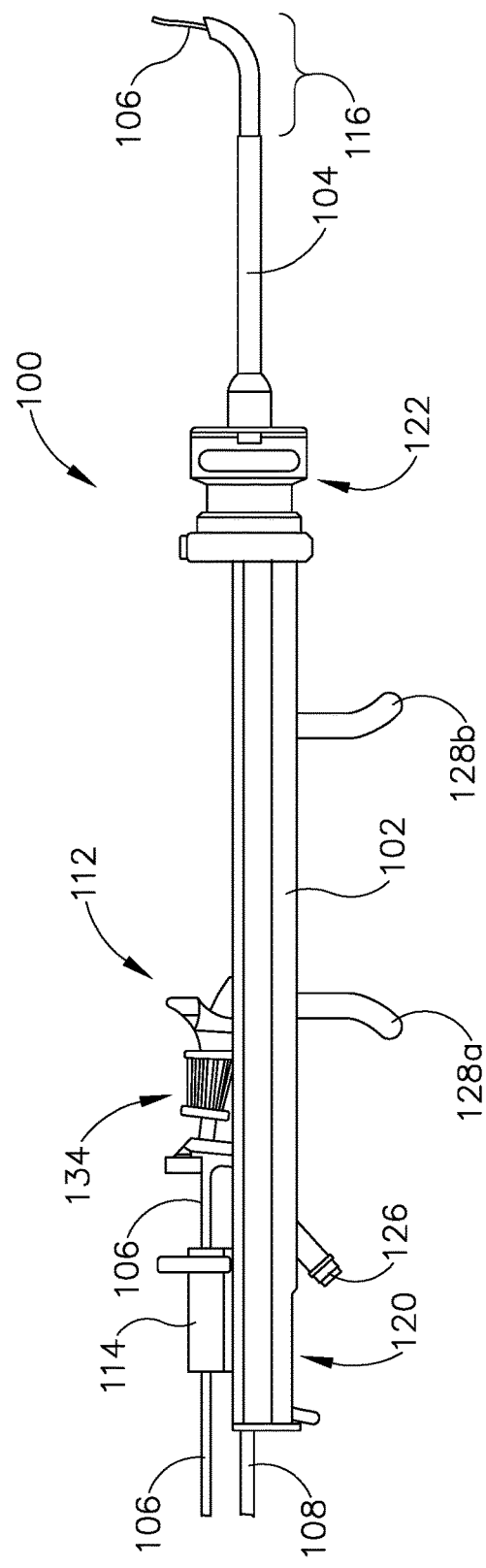

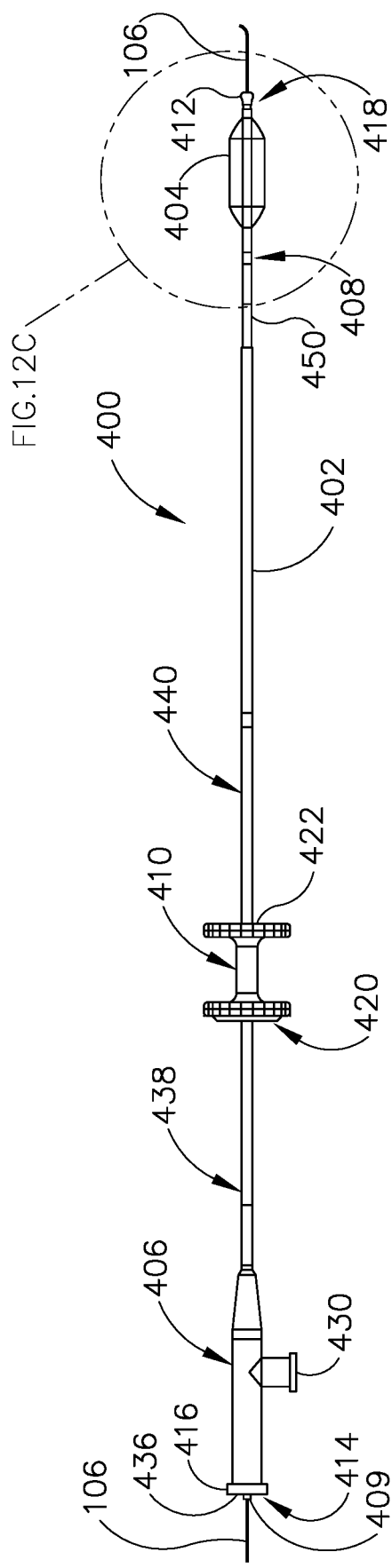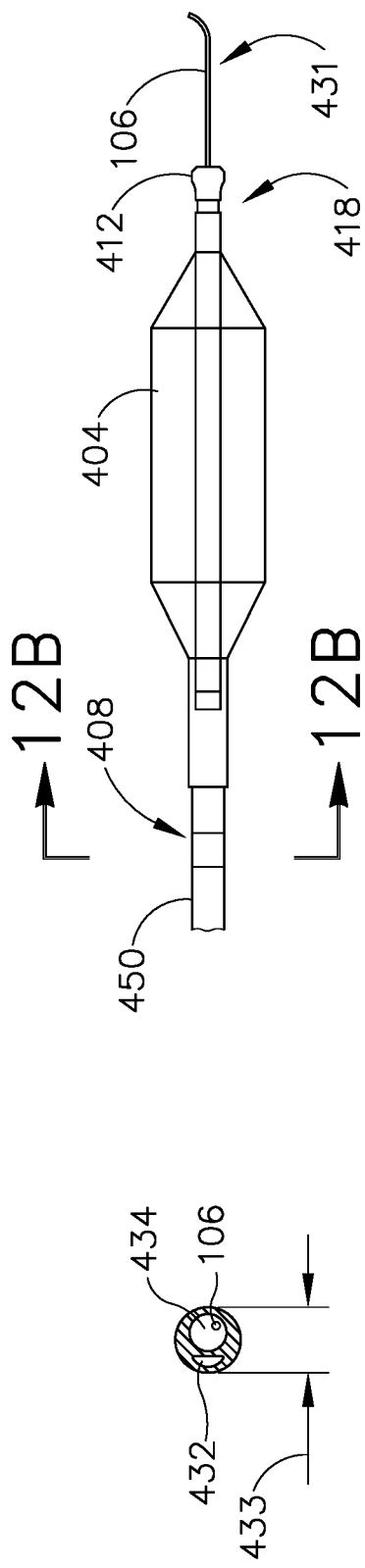
Fig.12A Fig.12B Fig.12C

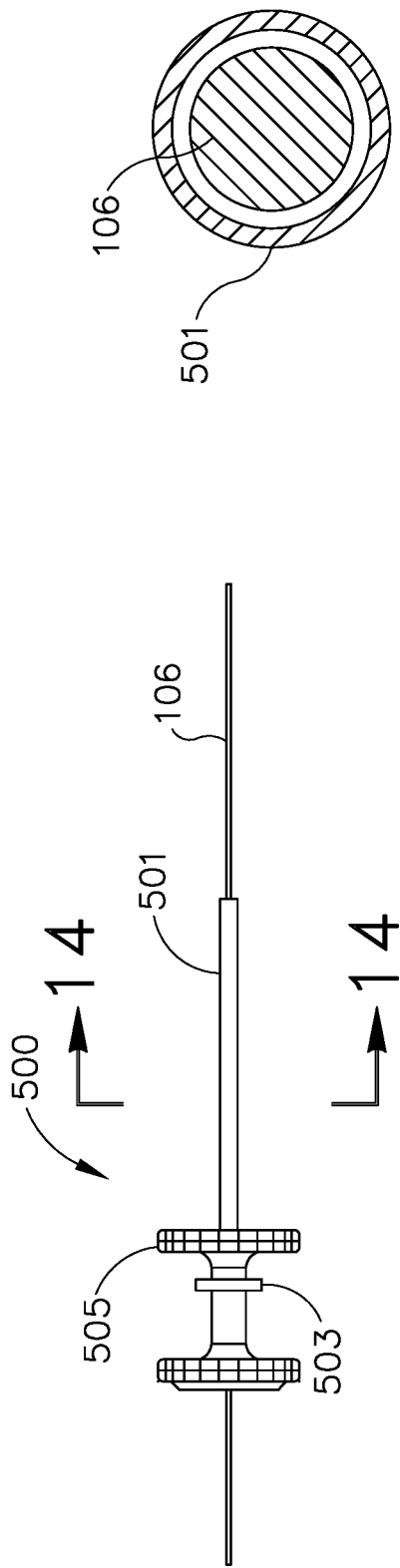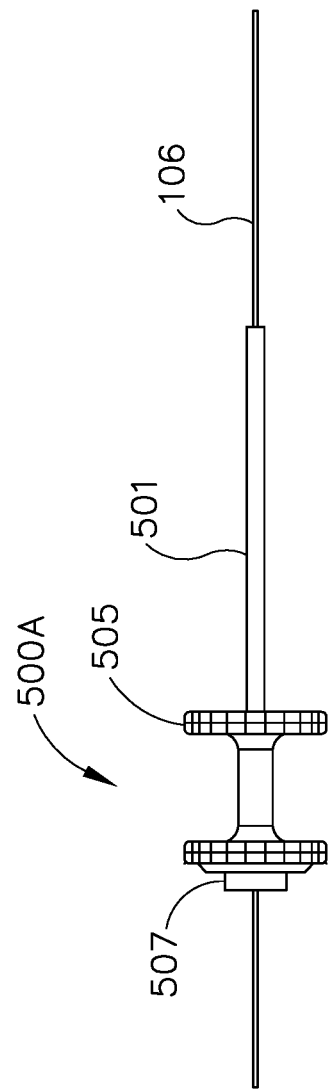

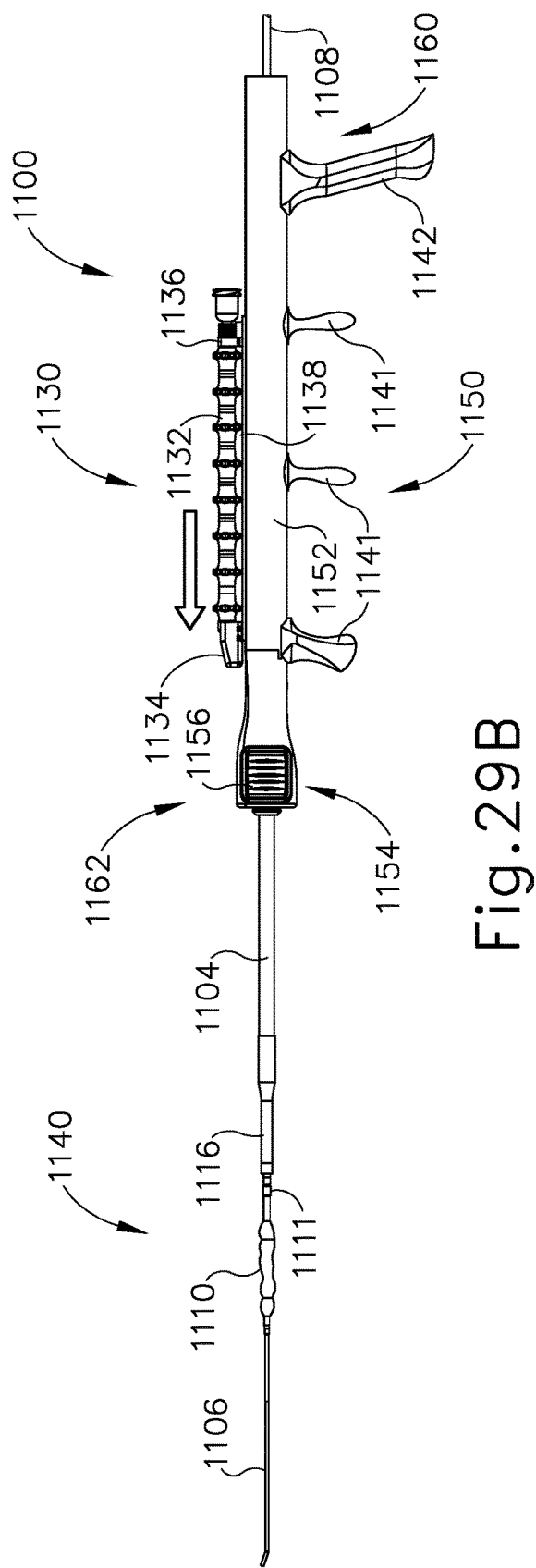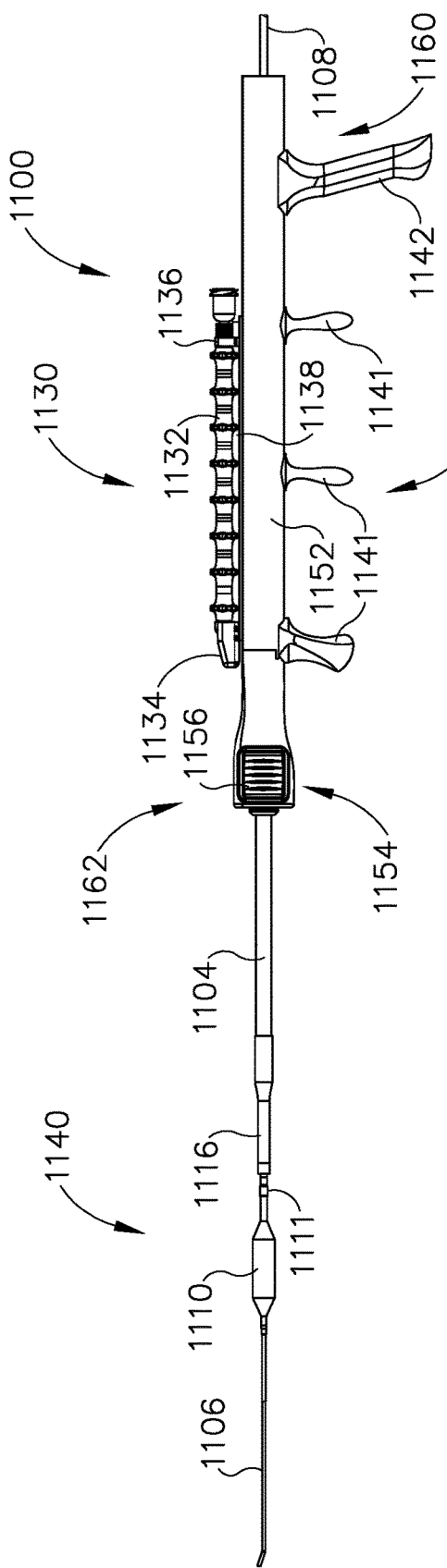

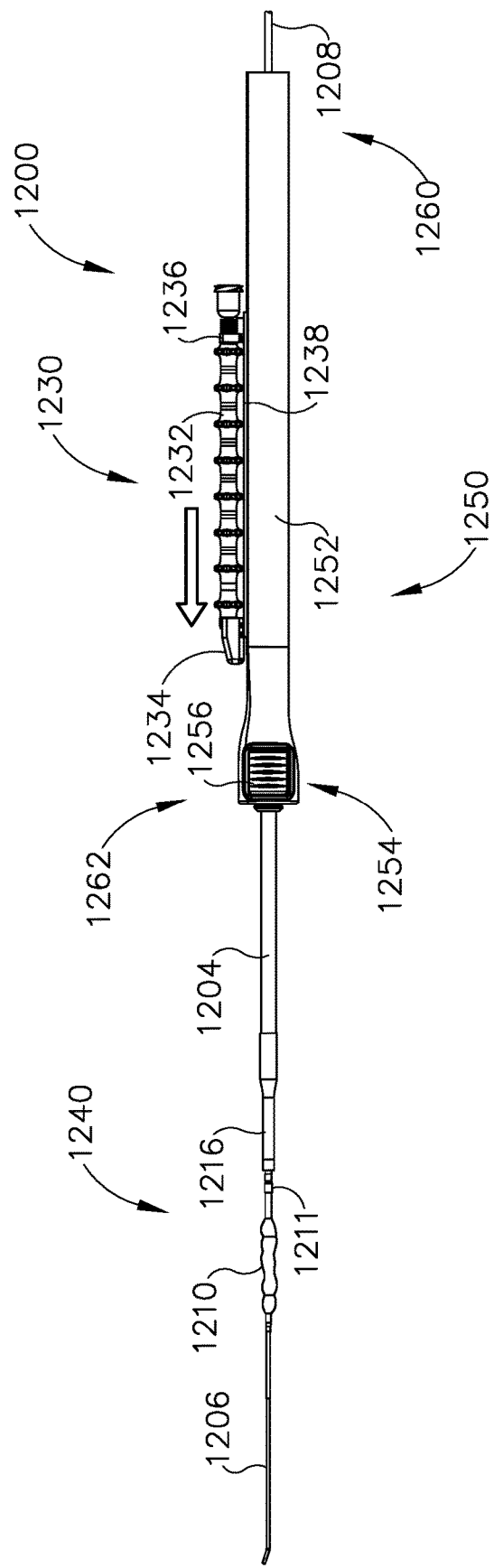
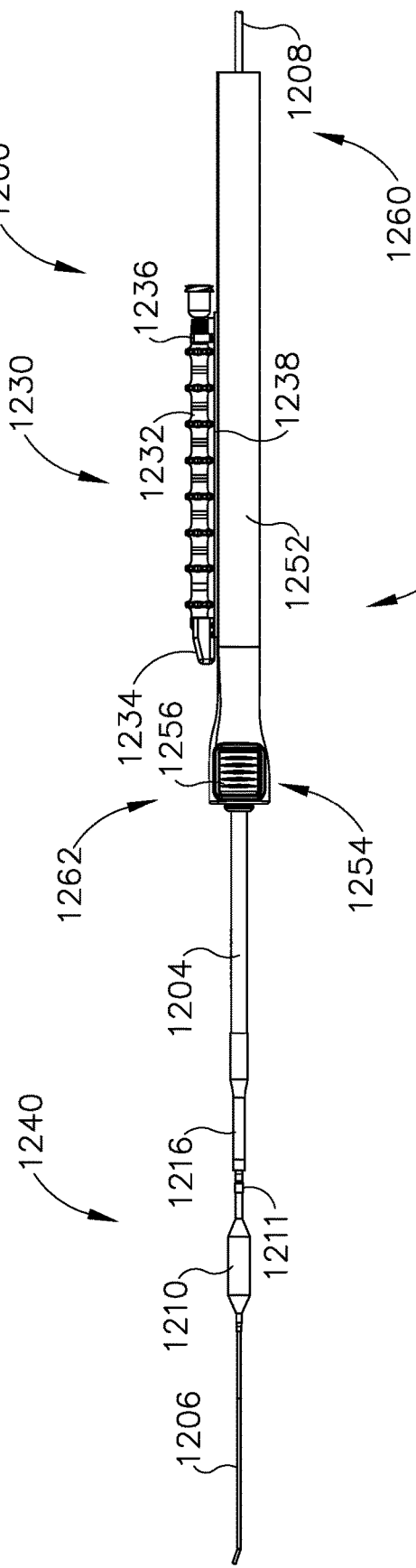
Fig. 35B
Fig. 35C

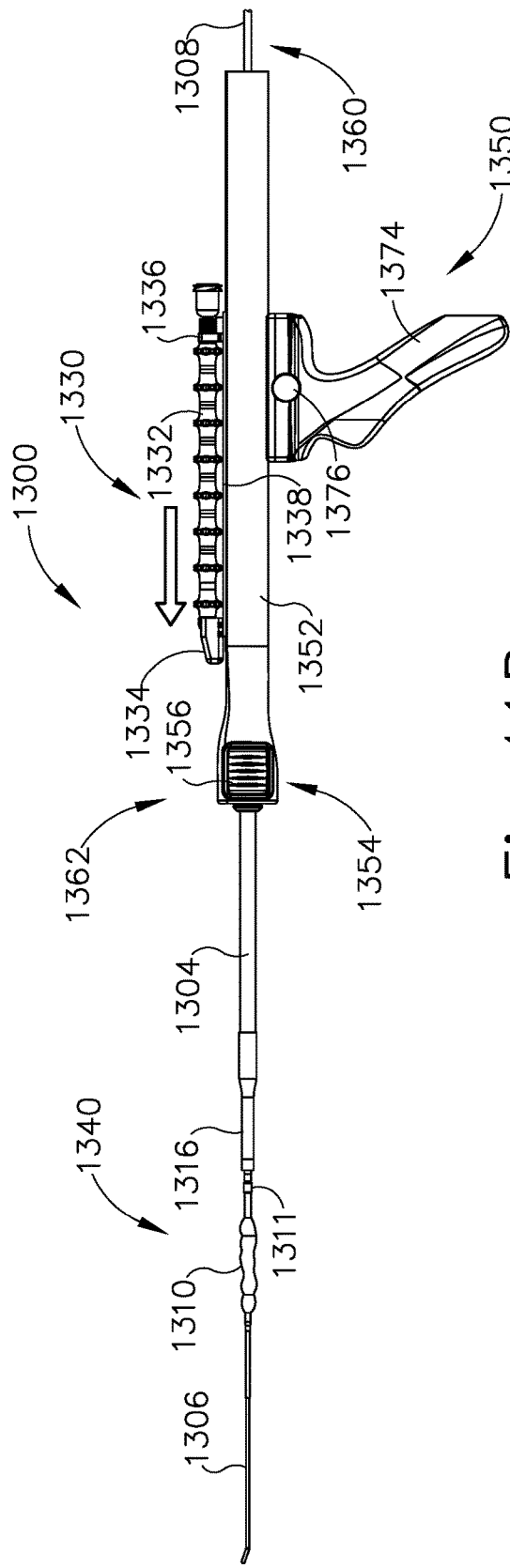
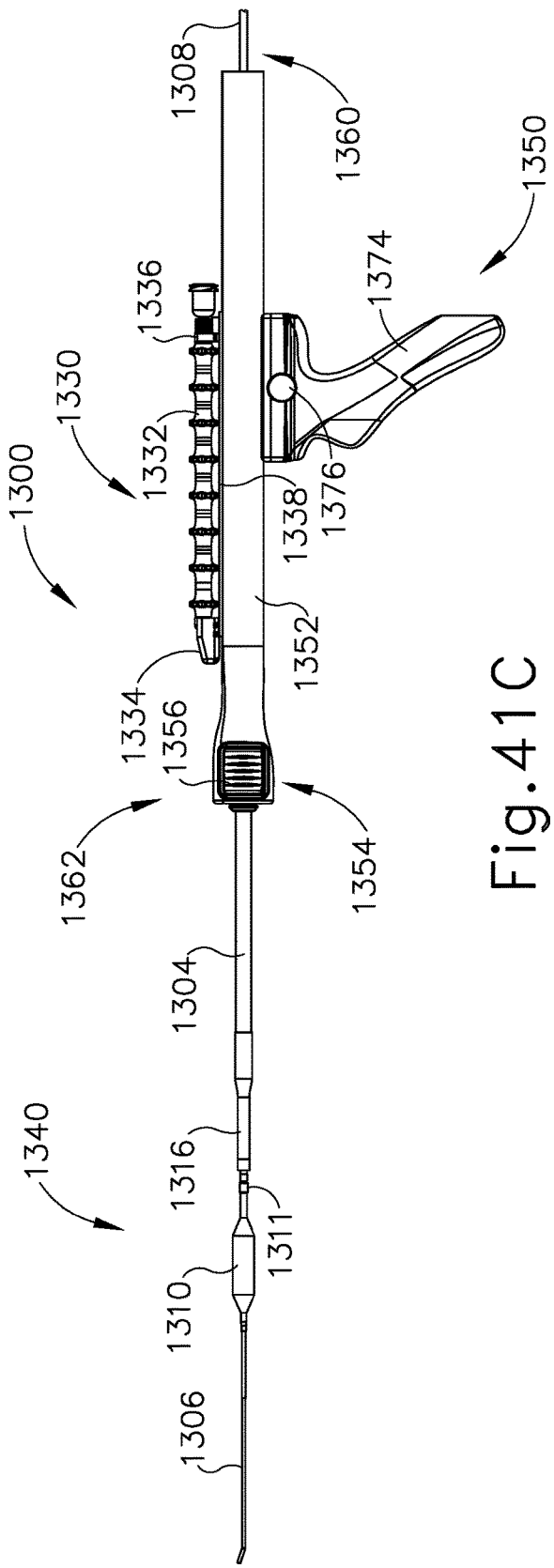
Fig.41B
Fig.41C

DILATION CATHETER ASSEMBLY WITH ADJUSTMENT FEATURES

PRIORITY

This application claims priority to U.S. Provisional Pat. App. No. 62/305,008, entitled "Dilation Catheter Assembly with Adjustment Features," filed Mar. 8, 2016, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Irvine, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. An example of such an illuminating guidewire is the Relieva Luma Sentry™ Sinus Illumination System by Acclarent, Inc. of Irvine, Calif.

It may be desirable to provide easily controlled inflation/deflation of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 3 depicts a side elevational view of the instrument of FIG. 2;

FIG. 4 depicts a side elevational view of the instrument of FIG. 3 with a guidewire of the instrument advanced distally;

FIG. 12A depicts a side elevational view of an exemplary balloon dilation catheter that may be used with the guide catheter of FIG. 1;

FIG. 12B depicts a cross-sectional view of the balloon dilation catheter shown in FIG. 12A, taken along line 12B-12B of FIG. 12C;

FIG. 12C depicts an enlarged side elevational view of the distal end of the balloon dilation catheter shown in FIG. 12A;

FIG. 13 depicts a side elevational view of an exemplary stabilizing tube assembly having an actuator coupled with a stabilizing tube and a locking mechanism;

FIG. 14 depicts a cross-sectional view of the stabilizing tube assembly of FIG. 13, taken along line 14-14 of FIG. 13;

FIG. 15 depicts a side elevational view of another exemplary stabilizing tube assembly having an actuator coupled with a stabilizing tube and a locking mechanism;

FIG. 29B depicts a side elevational view of the dilation catheter system of FIG. 24, where the actuation assembly, dilation catheter assembly, and guidewire of FIG. 29A are in an advanced position, and the dilator is deflated;

FIG. 29C depicts a side elevational view of the dilation catheter system of FIG. 24, where the actuation assembly, dilation catheter assembly, and guidewire of FIG. 29A are in the advanced position, and the dilator is inflated;

FIG. 35B depicts a side elevational view of the dilation catheter system of FIG. 30, where the actuation assembly, dilation catheter assembly, and guidewire of FIG. 35A are in an advanced position, and the dilator is deflated;

FIG. 35C depicts a side elevational view of the dilation catheter system of FIG. 30, where the actuation assembly, dilation catheter assembly, and guidewire of FIG. 35A are in the advanced position, and the dilator is inflated;

FIG. 41B depicts a side elevational view of the dilation catheter system of FIG. 36, where the actuation assembly, dilation catheter assembly, and guidewire of FIG. 41A are in an advanced position, and the dilator is deflated; and FIG. 41C depicts a side elevational view of the dilation catheter system of FIG. 36, where the actuation assembly, dilation catheter assembly, and guidewire of FIG. 41A are in the advanced position, and the dilator is inflated.

Figure 1:
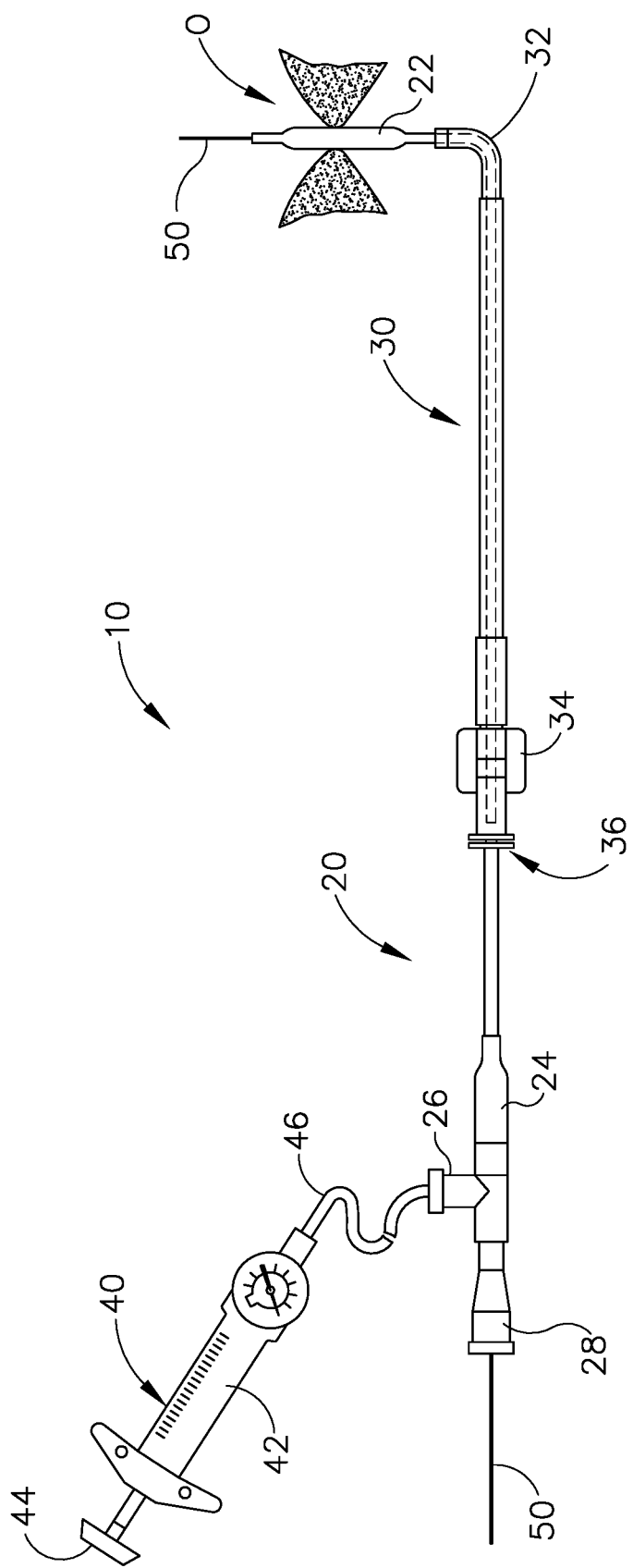
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; the Eustachian tube of the ear; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, now abandoned, the disclosure of which is incorporated by reference herein. In some versions, at least part of dilation catheter system (10) is configured similar to the Relieva® Spin Balloon Sinuplasty™ System by Acclarent, Inc. of Irvine, Calif.

The distal end of dilation catheter (20) includes an inflatable dilator (22). The proximal end of dilation catheter (20) includes a grip (24), which has a lateral port (26) and an open proximal end (28). Dilation catheter (20) includes a first lumen (not shown) that provides fluid communication between lateral port (26) and the interior of dilator (22). Dilator (22) may include any appropriate material, including a polyether block amide such as Pebax®. Dilator catheter (20) also includes a second lumen (not shown) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Irvine, Calif. In some other versions, dilator catheter (20) is configured similar to the Relieva Solo Pro™ Sinus Balloon Catheter by Acclarent, Inc. of Irvine, Calif. Other suitable forms that dilator catheter (20) may take will be apparent to those of ordinary skill in the art in view of the teachings herein.

Guide catheter (30) of the present example includes a bent distal end (32) and a grip (34) at its proximal end. Grip (34) has an open proximal end (36). Guide catheter (30) defines a lumen that is configured to slidably receive catheter (20), such that guide catheter (30) may guide dilator (22) out through bent distal end (32). In some versions, guide catheter (30) is configured similar to the Relieva Flex™ Sinus Guide Catheter by Acclarent, Inc. of Irvine, Calif. Other suitable forms that guide catheter (30) may take will be apparent to those of ordinary skill in the art in view of the teachings herein.

Inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26). In some versions, inflator (40) is constructed and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein.

In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, issued as U.S. Pat. No. 9,155,492 on Oct. 13, 2015, the disclosure of which is incorporated by reference herein. In some versions, guidewire (50) is configured similar to the Relieva Luma Sentry™ Sinus Illumination System by Acclarent, Inc. of Irvine, Calif. Other suitable forms that guidewire (50) may take will be apparent to those of ordinary skill in the art in view of the teachings herein.

In an exemplary dilation procedure, guide catheter (30) may first be positioned near the targeted anatomical passageway, such as a sinus ostium (O). Dilator (22) and the distal end of guidewire (50) may be positioned within or proximal to bent distal end (32) of guide catheter (30) at this stage. Guide catheter (30) is initially inserted into the nose of the patient and is advanced to a position that is within or near the ostium (O) to be dilated. This positioning of guide catheter (30) may be performed under visualization provided by an endoscope. After guide catheter (30) has been positioned, the operator may advance guidewire (50) distally through guide catheter (30) such that a distal portion of the guidewire (50) passes through the sinus ostium (O) and into the sinus cavity. The operator may illuminate illumination fiber (56) and lens (58), which may provide transcutaneous illumination through the patient's face to enable the operator to visually confirm positioning of the distal end of guidewire (50) with relative ease.

With guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the sinus ostium (O) (or some other targeted anatomical passageway). After dilator (22) has been positioned within the ostium (O), dilator (22) may be inflated, thereby dilating the ostium. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a pressure of about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient.

In some instances, it may be desirable to irrigate the paranasal sinus and/or the nasal cavity after dilation catheter (20) has been used to dilate an ostium (O). Such irrigation may be performed to flush out purulence, etc. that may be present after the dilation procedure. By way of example only, such irrigation may be carried out in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, now abandoned, the disclosure of which is incorporated by reference herein. An example of an irrigation catheter that may be fed through guide catheter (30) to reach the irrigation site after removal of dilation catheter (20) is the Relieva Vortex® Sinus Irrigation Catheter by Acclarent, Inc. of Irvine, Calif. Another example of an irrigation catheter that may be fed through guide catheter (30) to reach the irrigation site after removal of dilation catheter (20) is the Relieva Ultirra® Sinus Irrigation Catheter by Acclarent, Inc. of Irvine, Calif. Of course, irrigation may be provided in the absence of a dilation procedure; and a dilation procedure may be completed without also including irrigation.

II. Overview of Exemplary Dilation Catheter Instrument

Figure 2:
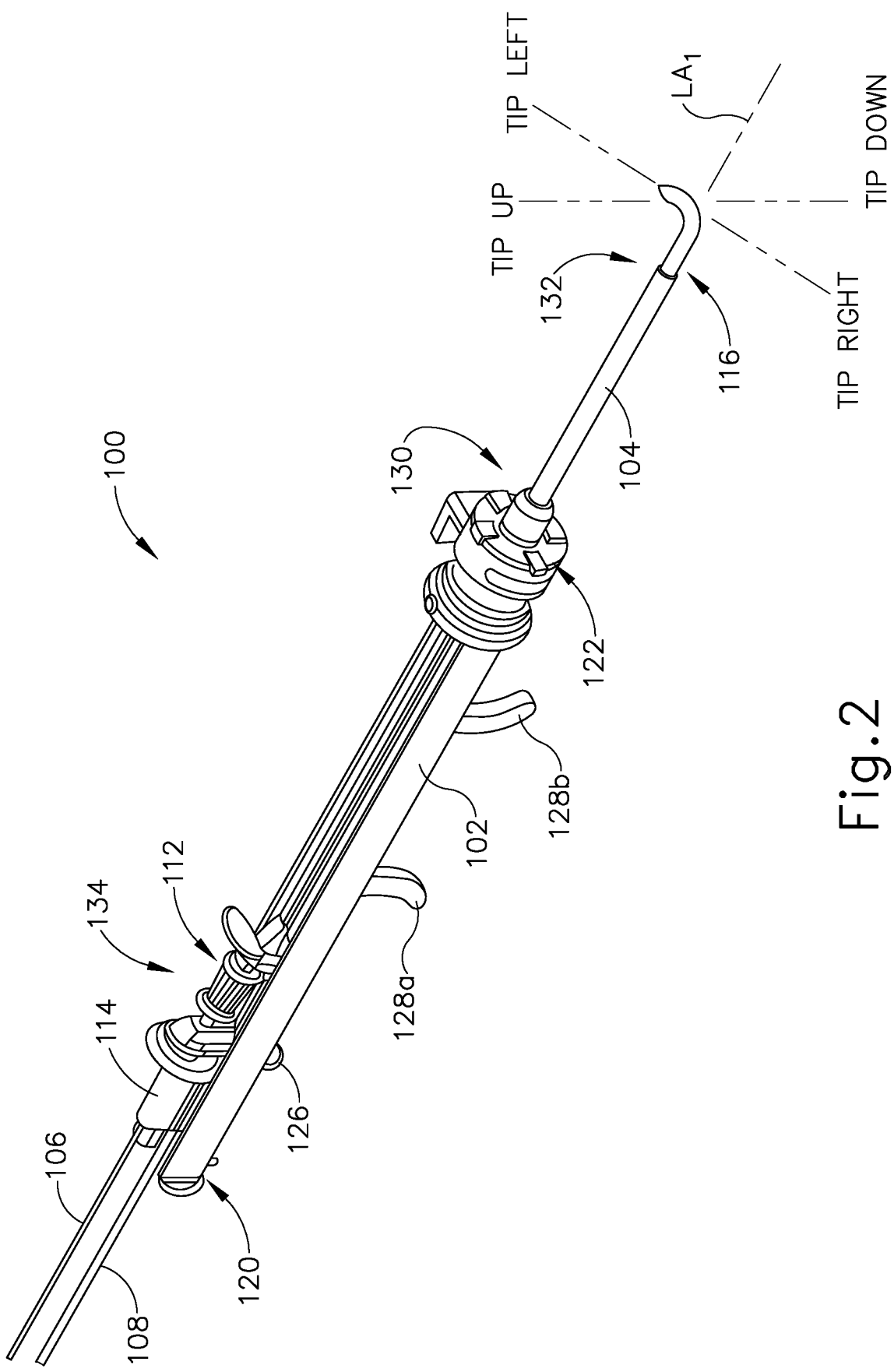
FIG. 2 depicts a perspective view of an instrument suitable for incorporation with the dilation catheter system of FIG. 1.

FIGS. 2-6 show an instrument (100) that may be used to treat a paranasal sinus drainage passageway (e.g., a frontal recess, a frontal sinus ostium, a maxillary sinus ostium, a sphenoid sinus ostium, etc.) or an Eustachian tube passageway. For instance, instrument (100) may be used to dilate a paranasal sinus drainage passageway. The various features of instrument (100) may be readily incorporated into dilation catheter system (10) discussed above. Instrument (100) of this example comprises a handle (102), a guide catheter (104), a guidewire (106), a dilation catheter (108), a guidewire movement mechanism (112), a dilation catheter movement actuator (114), a detachable guide tip (116) (shown with a curved (angled) tip in a "tip up" orientation), and a guidewire support (118). FIG. 2 includes a series of markers depicting alternative orientations of guide tip (116). In particular, a "tip up," a "tip left," a "tip down," and a "tip right" orientation of guide tip (116) are shown in FIG. 2.

As shown in FIGS. 2-4, handle (102) of the present example includes a proximal end (120) and a distal end (122); and defines a longitudinal axis (LA1) along the length of handle (102). Handle (102) further includes a fluid port (126) and finger anchoring pegs (128a) and (128b). In the present example, fluid port (126) is configured to couple with a source of suction to provide suction via guide catheter (104). In addition or in the alternative, fluid port (126) may be coupled with a fluid source to provide irrigation. Other suitable ways in which fluid port (126) may be made and used will be apparent to those of ordinary skill in the art in view of the teachings herein. Handle (102) is sized and shaped such that instrument (100) can be manipulated and operated by a user (such as a physician) in a convenient and efficient single-handed manner if so desired, with finger anchoring pegs (128a) and (128b) promoting gripping of handle (102) with a single hand. Handle (102) can be formed of any suitable material including, for example, polycarbonate and ABS (acetonitrile butadiene styrene) and can be manufactured using any suitable technique including, for example, injection molding of two clamshell handle halves. Various suitable materials and methods that may be used to manufacture handle (102) will be apparent to those of ordinary skill in the art in view of the teachings herein.

In the present example, guide catheter (104) serves as a substitute for guide catheter (30) described above and shown in FIG. 1. Guide catheter (104) of this example is attached to distal end (122) of handle (102) and defines an inner lumen (i.e., inner passage). Guide catheter (104) extends along longitudinal axis (LA1) and has a proximal end (130) and a distal end (132). Guide catheter (104) can be formed of any suitable materials including, for example, stainless steel, polymeric materials, and combinations thereof. By way of example only, the lumen of guide catheter (104) may have a diameter between about 0.070 and 0.150 inches. Alternatively, any other suitable dimensions may be used.

Detachable guide tip (116) is configured for removable attachment to, and detachment from, distal end (132) of guide catheter (104). However, detachable tips can be attached and detached from instrument (100) at any suitable location. For example, guide tip (116) can be attached anywhere along guide catheter (104) or at the distal end of handle (102). Guide tip (116) can be formed of any suitable material including, for example, stainless steel, polymeric materials and combinations thereof. It should also be understood that guide catheter (104) may have an integral tip that is pre-bent, malleable, or otherwise formed such that a separate, detachable guide tip (116) may be omitted from instrument (100). In other words, detachable guide tip (116) is merely optional.

Figure 5:
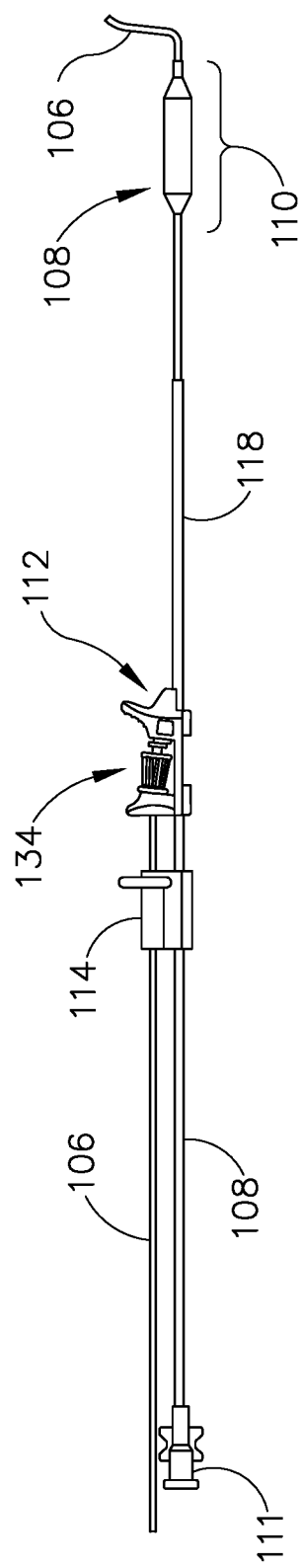
FIG. 5 depicts a side elevational view of the guidewire, a dilation catheter, a dilation catheter movement mechanism, a guidewire movement mechanism, and a guidewire support of the instrument of FIG. 2, with a working balloon segment of the dilation catheter shown in an inflated state.
Figure 6:
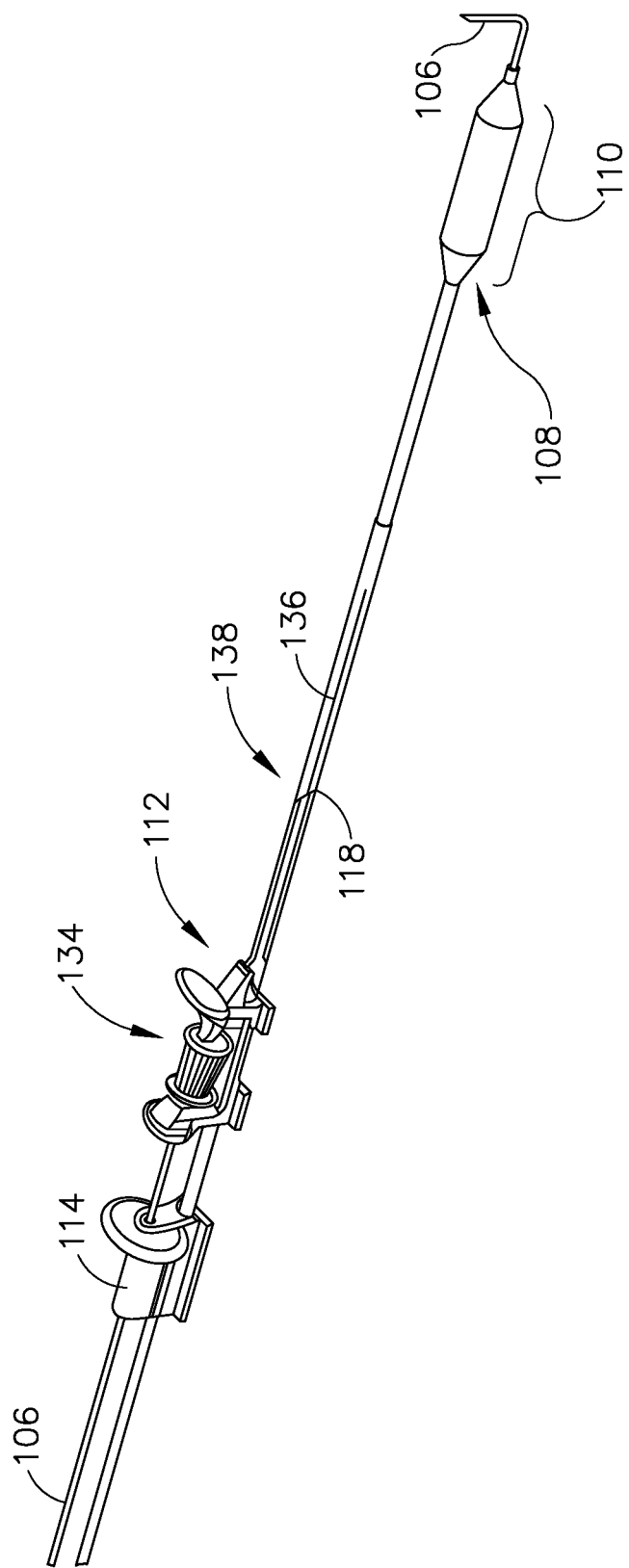
FIG. 6 depicts a perspective view of the guidewire, dilation catheter, dilation catheter movement mechanism, guidewire movement mechanism, and guidewire support of FIG. 5.

Dilation catheter (108) serves as a substitute for dilator catheter (20) described above. As best seen in FIGS. 5-6, dilation catheter (108) of the present example comprises an inflatable balloon (110) and an inflation port (111). Dilation catheter (108) further defines a first inner lumen and a second inner lumen. The first inner lumen of dilation catheter (108) distally terminates in balloon (110) and provides a path for fluid communication between inflation port (111) and balloon (110). Inflation port (111) may thus be coupled with a fluid source (e.g., inflator (40), etc.) to provide selective inflation of balloon (110) in accordance with the teachings herein. The second inner lumen of dilation catheter (108) extends all the way to the open distal end of dilation catheter (108) and provides a passageway to slidably receive guidewire (106) as described below. Dilation catheter (108) is slidably disposed at least partially in handle (102) and in the lumen of guide catheter (104). Dilation catheter (108) may be configured and operable in accordance with any suitable dilation catheters known to one skilled in the art.

During operation of instrument (100), dilation catheter (108) may be translated between a proximal position and a distal position. In particular, dilation catheter (108) may be longitudinally advanced and retracted relative to handle (102) and through the lumen of guide catheter (104). When dilation catheter (108) is in the proximal position, balloon (110) may be positioned within the lumen of guide catheter (104), proximal to the distal end (132) of guide catheter (104). When dilation catheter (108) is in the distal position, balloon (110) may be positioned distal to the distal end (132) of guide catheter (104). In versions where guide tip (116) is included, balloon (110) may also be positioned distal to the distal end of guide tip (116) when dilation catheter (108) is in the distal position.

Dilation catheter movement actuator (114) is operatively disposed on handle (102) and is operable to provide the above-described longitudinal advancement and retraction of dilation catheter (108) between the proximal and distal positions. In particular, dilation catheter movement actuator (114) provides such movement by longitudinally sliding along handle (102). Although dilation catheter movement actuator (114) of the present example is described as sliding along the length of handle (102), movement of dilation catheter (108) can be accomplished by any other suitable operation. In some variations, dilation catheter movement actuator (114) is rotatable relative to handle (102) to provide longitudinal advancement and retraction of dilation catheter (108). Various suitable ways in which dilation catheter (108) may be longitudinally advanced and retracted relative to handle (102) and through the lumen of guide catheter (104) will be apparent to those of ordinary skill in the art in view of the teachings herein.

In the present example, guidewire (106) serves as a substitute for guidewire (50) described above. Guidewire (106) of this example is slidably disposed in dilation catheter movement actuator (114), at least partially in handle (102), in guidewire support (118), and in the second inner lumen of dilation catheter (108). Guidewire (106) may be configured and operable in accordance with any suitable guidewire known to one skilled in the art including, for example, an illuminating guidewire that is configured to provide a user with confirmation of sinus access via transillumination (e.g., guidewire (50) described above, etc.). Guidewire support (118) of instrument (100) is operatively disposed within handle (102) and provides additional column strength to guidewire (106), such that guidewire support (118) prevents guidewire (106) from buckling within handle (102) during advancement of guidewire (106) relative to handle (102). As shown in FIG. 6, guidewire support (118) includes a slit-shaped opening (136) into which guidewire (106) is fed by guidewire movement mechanism (112). In some versions, guidewire support (118) comprises a hypotube. In addition or in the alternative, guidewire support (118) may be provided by dilation catheter (108).

Figure 7:
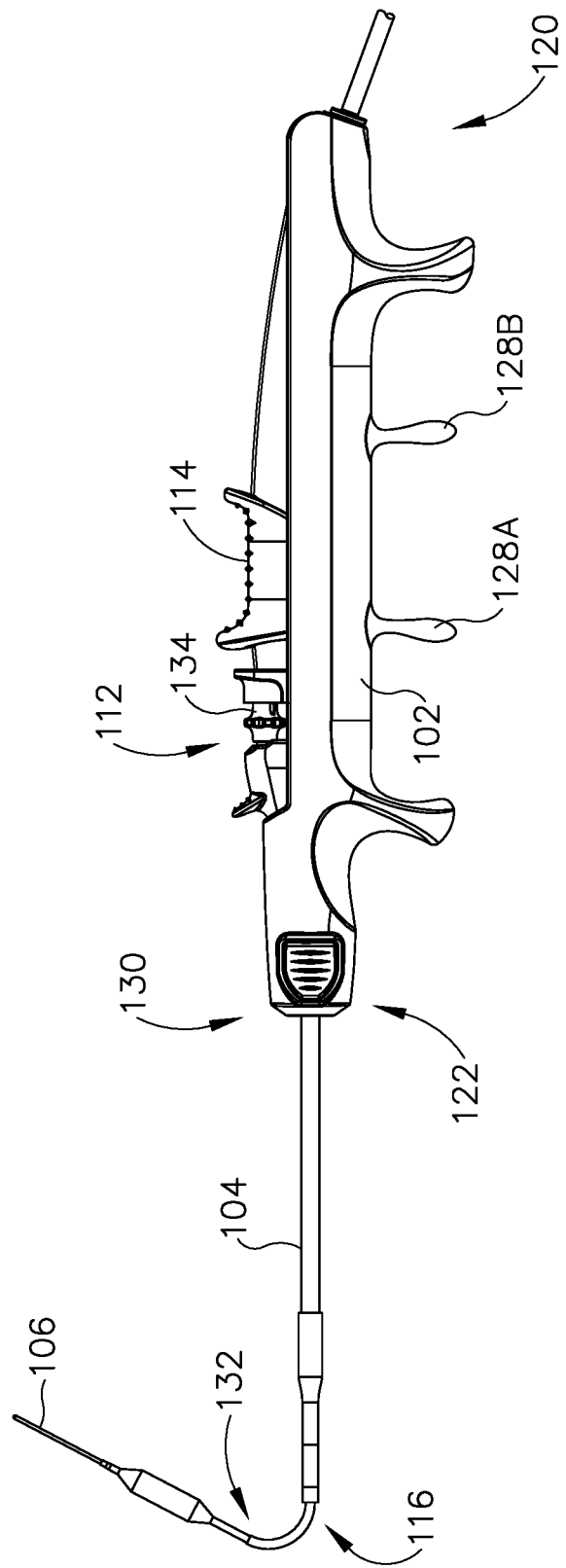
FIG. 7 depicts a perspective view of another exemplary instrument suitable for incorporation with the dilation catheter system of FIG. 1.

Guidewire movement mechanism (112) is operatively disposed on handle (102) and is operable to longitudinally advance and retract guidewire (106) relative to handle (102), through guidewire support (118), and through the lumen of guide catheter (104) by longitudinal sliding of guidewire movement mechanism (112) along the length of handle (102). FIGS. 2-6 show guidewire movement mechanism (112) and guidewire (106) in a proximal position, where the distal end of guidewire (106) is positioned proximal to the distal end of detachable guide tip (116). In some versions, the distal end of guidewire (106) is also positioned proximal to distal end (132) of guide catheter (104) when guidewire (106) is in a proximal position as shown in FIGS. 2-6. FIG. 7 shows guidewire movement mechanism (112) and guidewire (106) in a distal position, where the distal end of guidewire (106) is positioned distal to the distal end of detachable guide tip (116). It should be understood that guidewire movement mechanism (112) may be used to advance the distal end of guidewire (106) through an opening of a paranasal sinus (or some other passageway); and then dilation catheter movement actuator (114) may be used to advance dilation catheter (108) along guidewire (106) to position balloon (110) in the opening of the paranasal sinus as described above. Balloon (110) may then be inflated to dilate the opening of the paranasal sinus.

In the present example, guidewire movement mechanism (112) further includes an integrated guidewire locking and rotation knob (134) that is operable to rotate guidewire (106) about the longitudinal axis of guidewire (106). Knob (134) is secured to guidewire (106) such that knob (134) and guidewire (106) rotate unitarily with each other about the longitudinal axis of guidewire (106). Knob (134) is also configured for securely locking and unlocking guidewire (106) to guidewire movement mechanism (112). Although guidewire movement mechanism (112) of the present example is described as sliding along the length of handle (102), movement of guidewire (106) can be accomplished by any other suitable operation. In some variations, guidewire movement mechanism (112) is rotatable relative to handle (102) to provide longitudinal advancement and retraction of guidewire (106). Various suitable ways in which guidewire (106) may be longitudinally advanced and retracted relative to handle (102) and through the second lumen of dilation catheter (108) will be apparent to those of ordinary skill in the art in view of the teachings herein.

In addition to or as an alternative to being constructed and operable in accordance with the above teachings, instrument (100) may be constructed and operable in accordance with at least some of the teachings of U.S. Pub. No. 2012/0071856, entitled "Medical Device and Method for Treatment of a Sinus Opening," published Mar. 22, 2012, issued as U.S. Pat. No. 9,554,,817 on Jan. 31, 2017, the disclosure of which is incorporated by reference herein. By way of example only, instrument (100) may include a "clicker" and/or other feature that provides audible and/or tactile feedback as knob (134) is rotated to rotate guidewire (106), as described in U.S. Pub. No. 2012/0071856, issued as U.S. Pat. No. 9,554,817 on Jan. 31, 2017. Of course, various other teachings of U.S. Pub. No. 2012/0071856, issued as U.S. Pat. No. 9,554,817 on Jan. 31, 2017, may also be readily incorporated into instrument (100). In addition or in the alternative, instrument (100) may be modified in accordance with the various teachings below.

III. Exemplary Elongated Dilation Catheter Instrument With Finger Ring

Figure 8A:
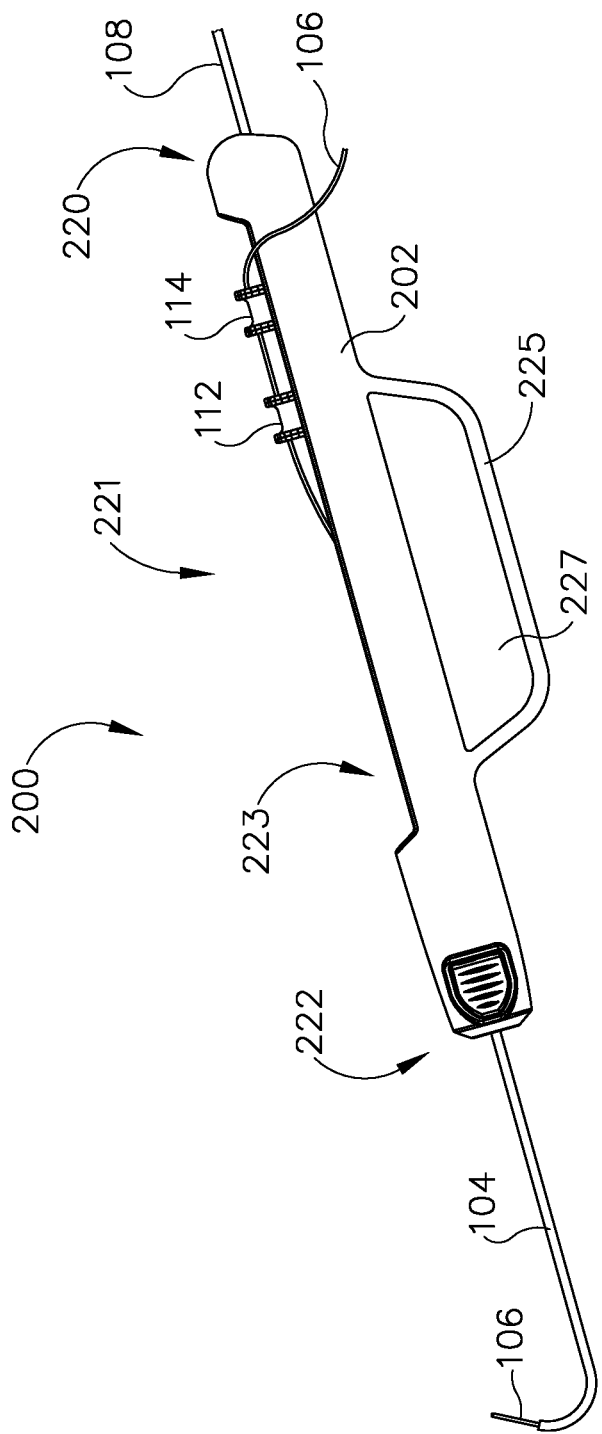
FIG. 8A depicts a side view of another exemplary instrument suitable for incorporation with the dilation catheter system of FIG. 1, with a guidewire in a proximal position and with a dilation catheter in a proximal position.
Figure 8B:
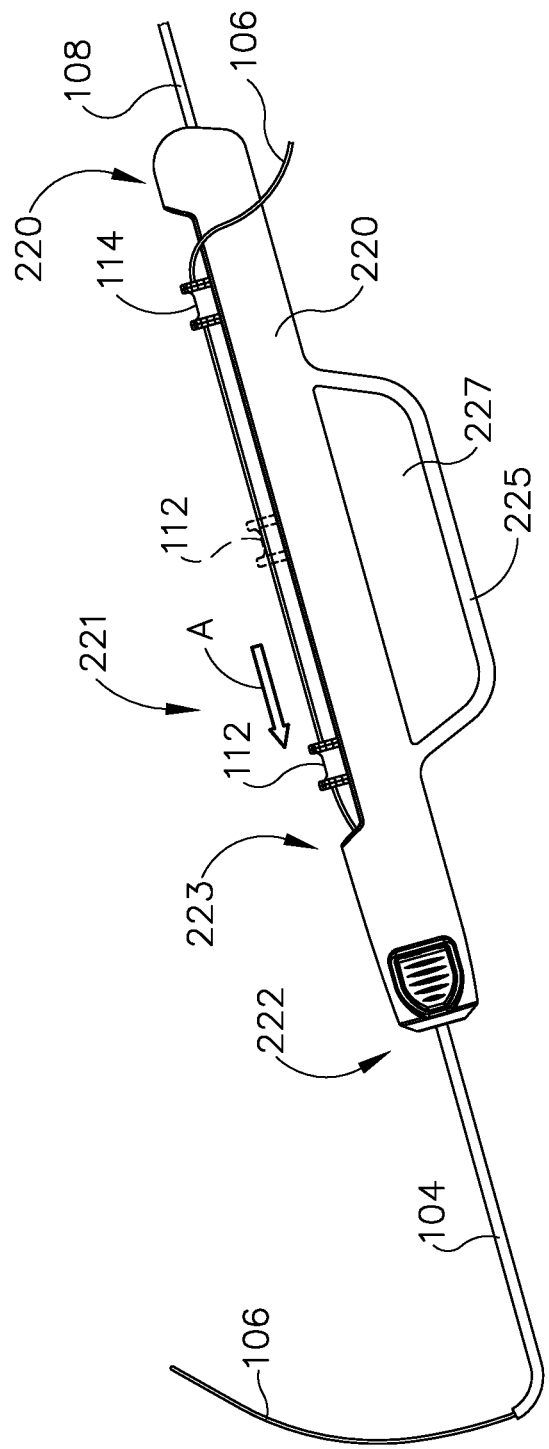
FIG. 8B depicts a side view of the instrument of FIG. 8A with a first actuator advanced distally to advance the guidewire distally.
Figure 8C:
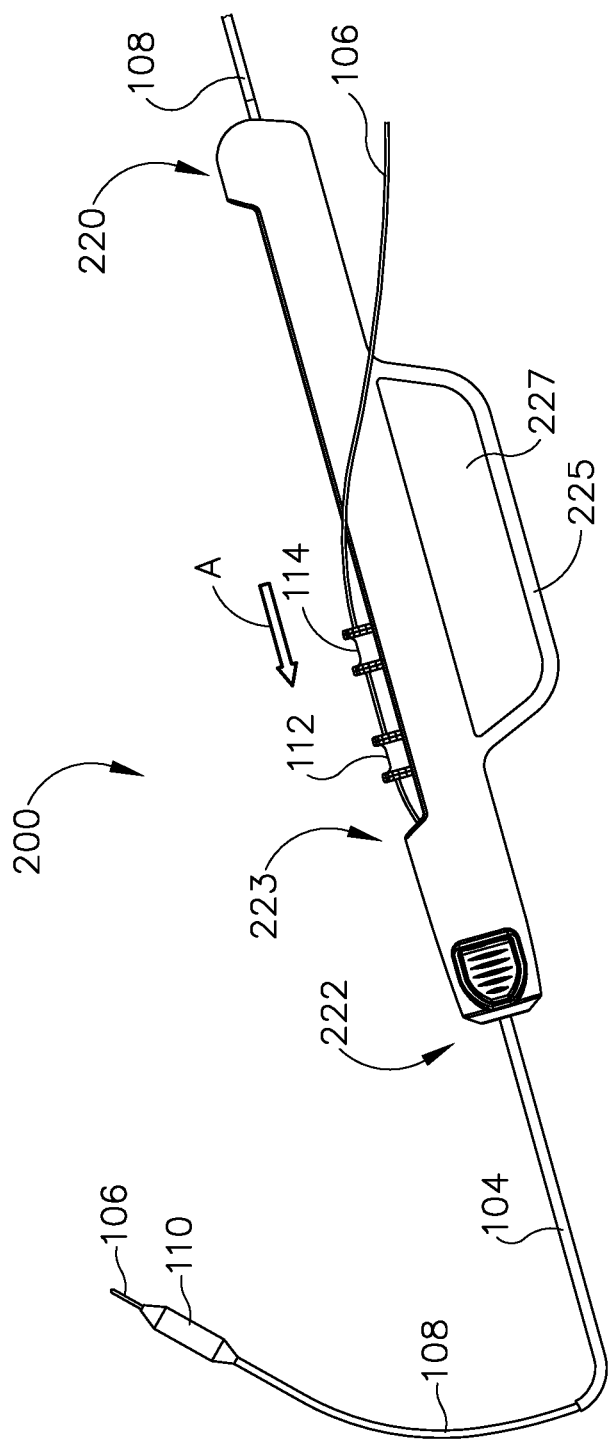
FIG. 8C depicts a side view of the instrument of FIG. 8A with a second actuator advanced distally to advance the dilation catheter distally.

As noted above, it may be desirable in some instances to provide an instrument similar to instrument (100) with an elongated handle (102) or overall frame. By reconfiguring handle (102), a modified version of instrument (100) may be held and manipulated in a different fashion, such as with a pencil grip instead of a power grip. FIGS. 8A-8C show an exemplary variation of instrument (100) in the form of a dilation catheter instrument (200). Instrument (200) of this example has an elongated handle (202) and a guidewire (106) that is secured to a guidewire movement mechanism (112).

Instrument (200) is similar in many respects to instrument (100), with like elements having like numbering, and may be readily incorporated into dilation catheter system (10). Elongated handle (202) extends from a proximal end (220) to a distal end (222), with an intermediate area (221) therebetween at the general mid-point between proximal end (220) and distal end (222). Elongated handle (202) includes a smaller cross-sectional profile when compared to handle (102). In some versions, handle (202) has a diameter of approximately 0.25 inches to allow the user to grasp handle (202) similar to the grasping of a pen or pencil. Handle (202) may be formed to include a circular, triangular, or any other cross-sectional profile. In the present example, handle (202) has a length of approximately 8 to 12 inches.

Instrument (200) further includes a channel (223) defined by handle (202) and extending generally from proximal end (220) to distal end (222). Channel (223) allows guidewire movement mechanism (112) and dilation catheter movement actuator (114) to slide therein from proximal end (220) to distal end (222) of handle (202). Instrument (200) further includes a grip ring (225) extending from handle (202), generally disposed proximate intermediate area (221) of handle (202). Ring (225) defines an opening (227) sized to receive a user's thumb, finger, or fingers to allow the user to grip instrument (200).

As noted above, a user may generally advance guidewire (106) and dilation catheter (108) the length of a single stroke of a user's hand using instrument (100). Conversely, instrument (200) includes elongated handle (202) to enable the user to advance guidewire (106) and dilation catheter (108) more than one stroke. In some versions of instrument (200), handle (202) is sized to allow for approximately two strokes of guidewire (106) and dilation catheter (108) by a user. Inasmuch as guidewire (106) is fixed to guidewire movement mechanism (112) and dilation catheter (108) is fixed to dilation catheter movement actuator (114), the elongated nature of handle (202) allows for an increased length of guidewire (106) and dilation catheter (108) projecting outwardly away from guide catheter (104). The increased in available length of guidewire (106) and dilation catheter (108) provides increased control to the user in fine tuning and configuring the ultimate placement of inflatable balloon (110) within the patient. Thus, the stroke or actuation distance to advance inflatable balloon (110) can be longer than the distance a user's finger or thumb can travel with one stroke. Elongated handle (202) allows the user to adjust the user's hand to hold more distally and allow the user to advance dilation catheter (108) a longer distance than a single stroke of a finger or thumb.

Instrument (200) as shown in FIGS. 8A-8C is sized to provide the full range of travel of guidewire movement mechanism (112) in response to two full actuation strokes by a user's finger. Similarly, instrument (200) is sized to provide the full range of travel of dilation catheter movement actuator (114) in response to two full actuation strokes by a user's finger. As shown in FIG. 8A, guidewire movement mechanism (112) is originally disposed at proximal end (220) of handle (202). As shown in FIG. 8B, the user grips ring (225) and manually moves guidewire movement mechanism (112) along channel (223) in the direction of Arrow A. Guidewire movement mechanism (112) is moved approximately one stroke until guidewire movement mechanism (112) rests at intermediate area (221) (shown in phantom). The user then repositions the user's hand to grip more distally on handle (202) and to allow the user to apply an additional stroke to guidewire movement mechanism (112), moving guidewire movement mechanism (112) from intermediate area (221) to distal end (222) of handle (202) in accordance with the second stroke. This two stoke configuration of handle (202) increases the length of guidewire (106) available beyond distal end (132) of guide catheter (104). It should be understood that some versions of guidewire movement mechanism (112) may provide rotation of guidewire (106) in addition to providing longitudinal translation of guidewire (106).

As shown in FIG. 8C, dilation catheter movement actuator (114) may also be moved approximately two strokes along the elongated length of handle (202) to increase the length of dilation catheter (108) available beyond distal end (132) of guide catheter (104). Thus, the user may enjoy finer control over the position of both guidewire (106) and dilation catheter (108).

In some versions of instrument (200), guidewire (106) is fixedly secured to dilation catheter (104) (e.g., as will be described in greater detail below), such that guidewire (106) and dilation catheter (104) may share a single actuator instead of having two different actuators. In such versions, the single actuator translates and rotates dilation catheter (108) and guidewire (106) together unitarily as a single unit. In some other version, the single actuator translates the dilation catheter (108) and guidewire (106) together unitarily as a single unit; yet also provides independent rotation of guidewire (106) relative to the dilation catheter (108). Examples of such an assembly are shown and described in U.S. patent application Ser. No. 62/305,083, entitled "Dilation Catheter Assembly with Rapid Change Components," filed on Mar. 8, 2016, the disclosure of which is incorporated by reference herein.

IV. Exemplary Unitary Actuator for Spinning, Advancing, and Retracting Guidewire and Dilation Catheter and Corresponding Handle It may be desirable in some instances to spin, advance, and retract the guidewire and the dilation catheter as a unit, with one rotation input feature, without an additional separate movement actuator (e.g., dilation catheter movement actuator (114)) for the dilation catheter. It may be additionally desirable in some instances to provide a handle corresponding to the unitary guidewire and dilation catheter actuator.

Figure 9:
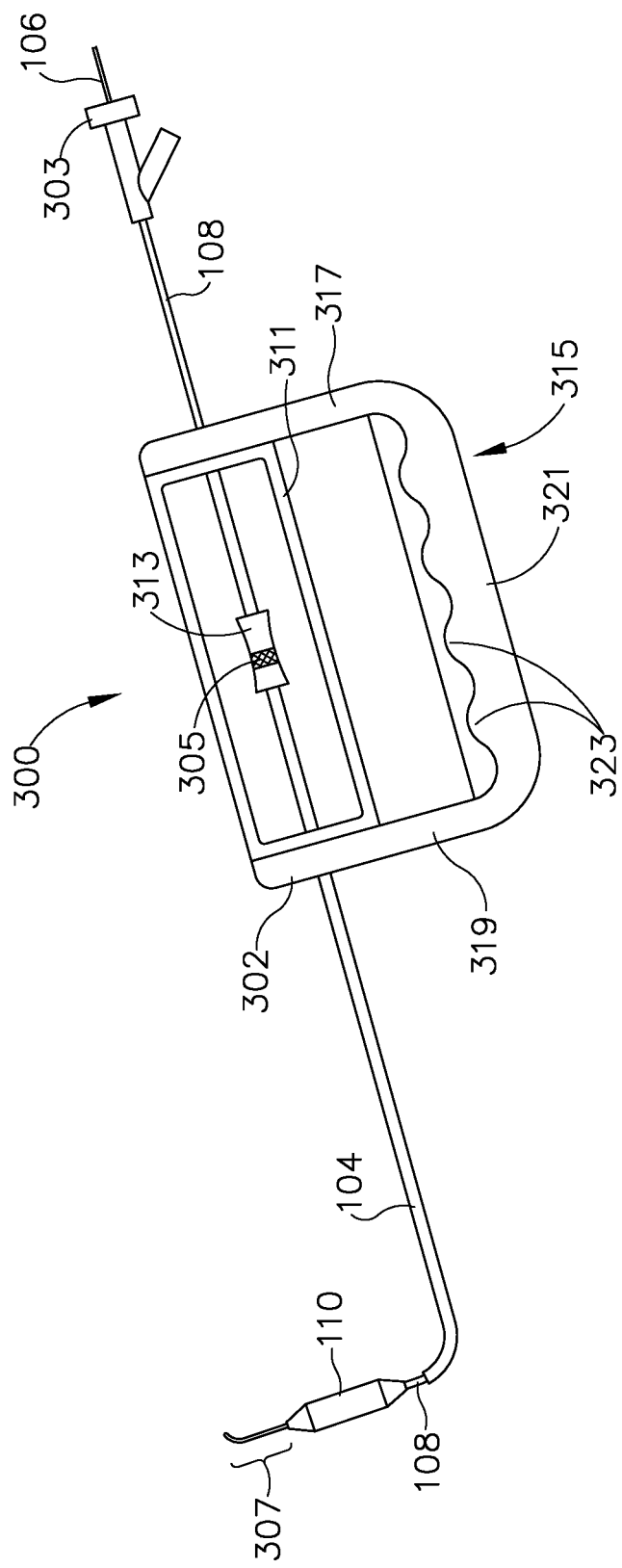
FIG. 9 depicts a side view of another exemplary instrument suitable for incorporation with the dilation catheter system of FIG. 1, with a dilation catheter and guidewire advanced to a distal position.
Figure 10:
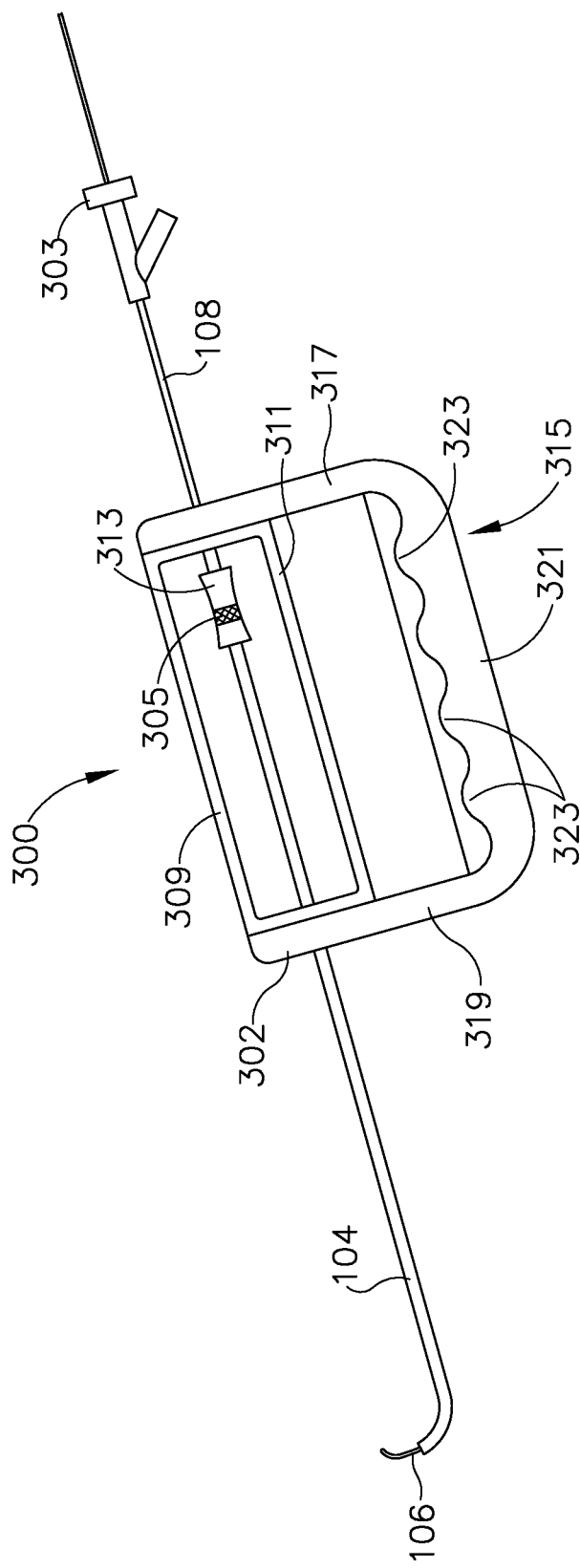
FIG. 10 depicts another side view of the instrument of FIG. 9, with the dilation catheter and guidewire retracted to a proximal position.
Figure 11:
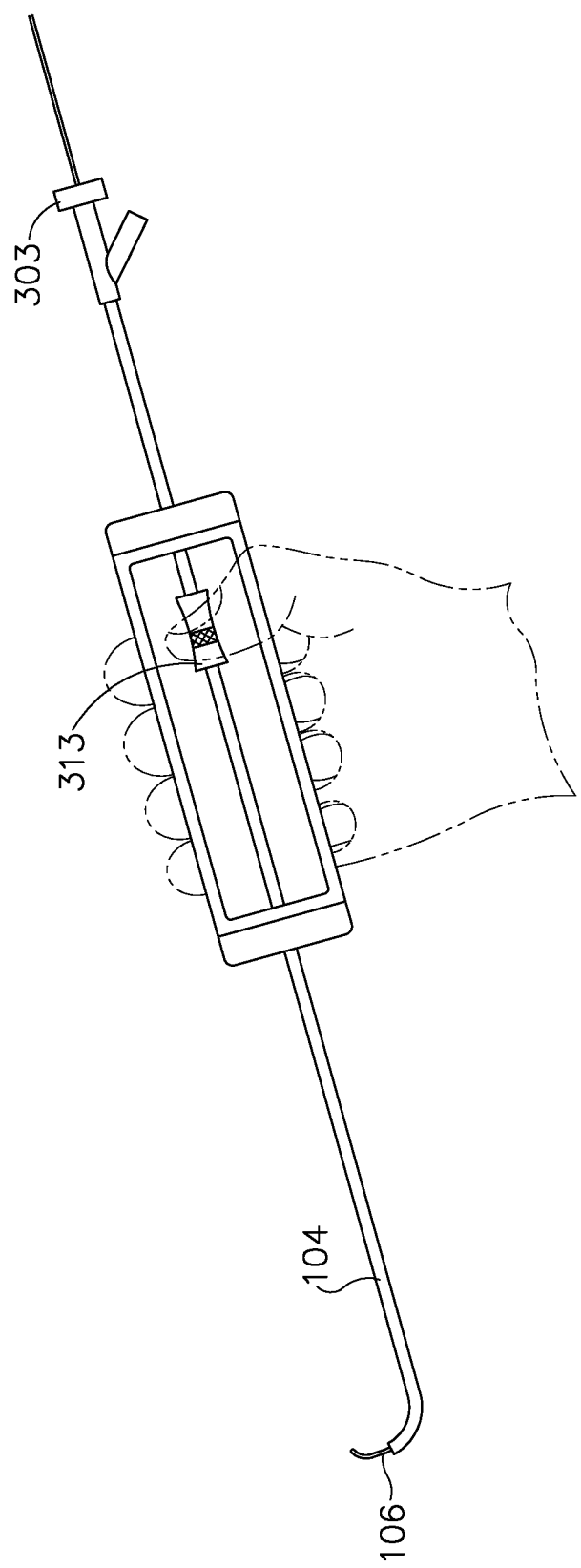
FIG. 11 depicts another side view of the instrument of FIG. 9 with a user's hand manipulating an actuator of the instrument.

FIGS. 9-11 show an exemplary instrument (300) that provides both unitary rotation and unitary longitudinal translation of guidewire (106) and dilation catheter (108). Instrument (300) is similar in many respects to instrument (100), with like elements having like numbering, and may be readily incorporated into dilation catheter system (10). Instrument (300) is provided with a unitary actuator (313) and a handle (302) that is configured to complement unitary actuator (313).

As shown in FIG. 9, instrument (300) may include a locking mechanism positioned anywhere on instrument (300) for selectively locking guidewire (106) with dilation catheter (108). In the example shown, the locking mechanism comprises a lock (303) in the form of a collet, luer lock, or other feature that is positioned at the proximal end of dilation catheter (108). In addition or in the alternative, a lock (305) may be integrated or adjacent to handle (302) and configured to fix guidewire (106) within dilation catheter (108). Lock (303, 305) may comprise any suitable kind of feature that secures guidewire (106) with dilation catheter (108). In some versions, lock (303, 305) provides unitary translation of guidewire (106) with dilation catheter (108);

while permitting guidewire (106) to rotate relative to dilation catheter (108). In some other versions, lock (303, 305) provides unitary translation and rotation of guidewire (106) with dilation catheter (108). Various suitable forms that lock (303, 305) may take, as well as various suitable positions where lock (303, 305) may be located, will be apparent to those of ordinary skill in the art in view of the teachings herein.

The length of guidewire (106) relative to distal end of instrument (300) and relative to inflatable balloon (110) may be set or configured as a distally extending portion (307) of guidewire (106). Extending portion (307) may be set by the user before fixing guidewire (106) to dilation catheter (108) to allow the user to fine tune instrument (300) to the particular treatment and the targeted anatomical structure. For example, for the frontal sinuses, extending portion (307) of guidewire (106) may be fixed at a longer length; and for the maxillary sinuses, extending portion (307) of guidewire (106) may be fixed at a shorter length. Conversely, the user may unlock lock (303, 305) to allow guidewire (106) to slide proximally out of instrument (300). Thereafter, guidewire (106) may be replaced with a different guidewire (106) with more desirable features. For example, the user may insert a guidewire (106) having an illumination element or a less expensive guidewire (106). Alternatively, the user may elect to not use a guidewire (106) at all. For example, if the user is treating a Eustachian tube, extending portion (307) of guidewire (106) may not be necessary or may be undesirable.

Due to the absence of separate guidewire movement mechanism (112) and dilation catheter movement actuator (114), handle (302) may be formed to complement unitary actuator (313). As shown in FIG. 10, handle (302) includes a first frame member (309) and an opposed second frame member (311). Handle (302) further includes a generally U-shaped grip element (315) extending outwardly away first frame member (309) and second frame member (311) by way of a proximal neck (317) and a distal neck (319). Grip element (315) includes a grip portion (321) having a plurality of grip features (323) disposed thereon. Grip features (323) present an undulating surface and are generally sized and positioned to interlace with a user's fingers to allow for a tight ergonomic grip between the user's hand and instrument (300).

As shown in FIG. 11, as a user grasps grip portion (321) of grip element (315), the user's thumb is well positioned to manipulate unitary actuator (313) and thereby spin, advance, and retract the guidewire (106) and dilation catheter (108) as a unit and as desired. Grip element (315) allows for a tight and stable grasping of instrument (300) by four fingers, while the thumb is free to actuate the fixed guidewire (106) and dilation catheter (108). In some instances, the user may use the user's thumb to advance unitary actuator (313) through a first range of distal motion; and then use the user's index finger to advance unitary actuator (313) through a second range of distal motion. Other suitable ways in which instrument (300) may be grasped and manipulated will be apparent to those of ordinary skill in the art in view of the teachings herein.

In some variations of instrument (300), grip element (315) is integrated into either first frame member (309) or second frame member (311), such that necks (317, 319) are omitted. In such versions, grip features (323) may be defined by either first frame member (309) or second frame member (311). Such versions of instrument (300) may still be grasped with a power grip, with the user manipulating unitary actuator (313) with the user's thumb and/or index finger.

Figure 20:
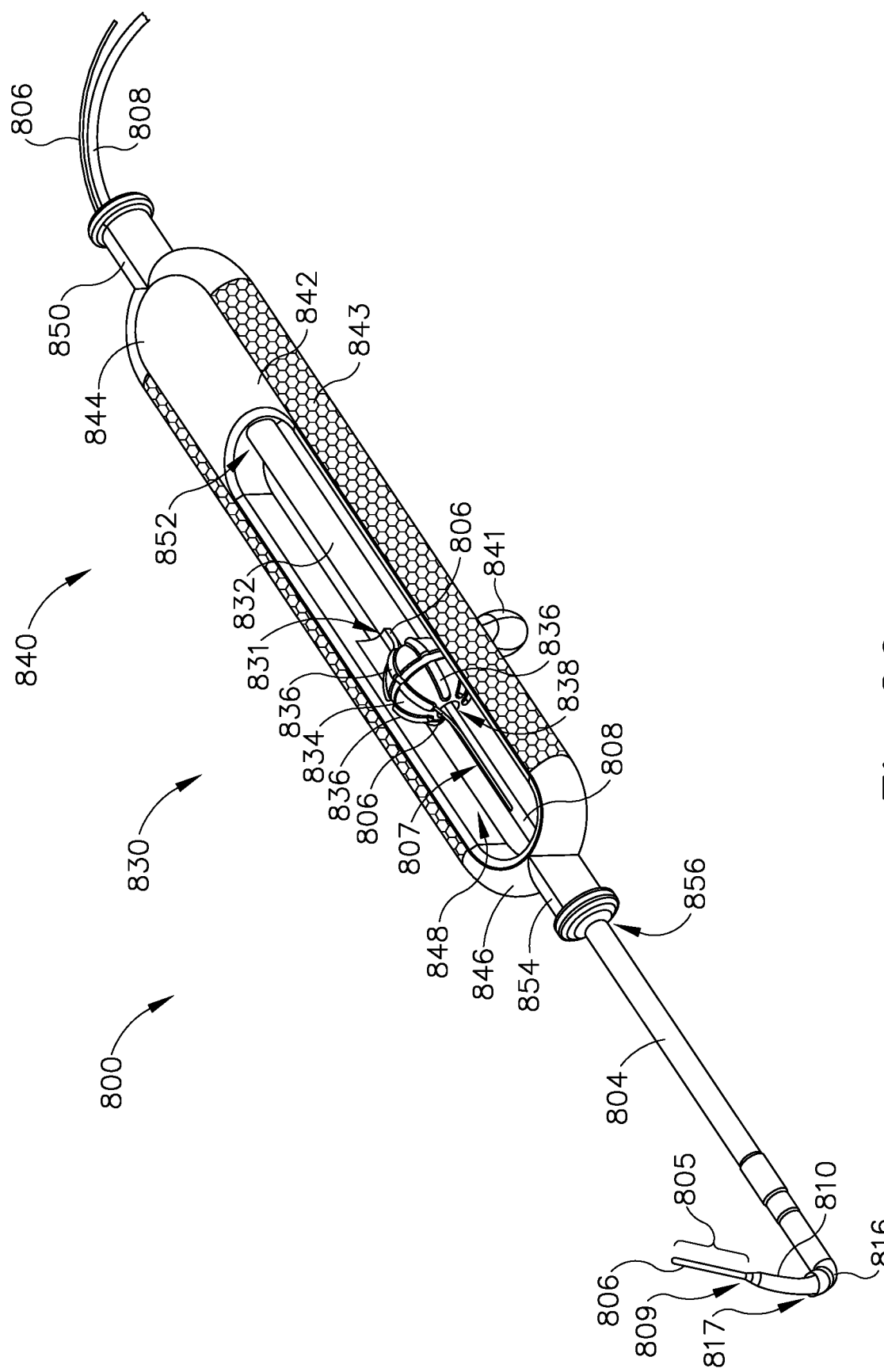
FIG. 20 depicts a perspective view of another exemplary instrument suitable for incorporation with the dilation catheter system of FIG. 1, with the dilation catheter and the guidewire at an intermediate position.
Figure 21:
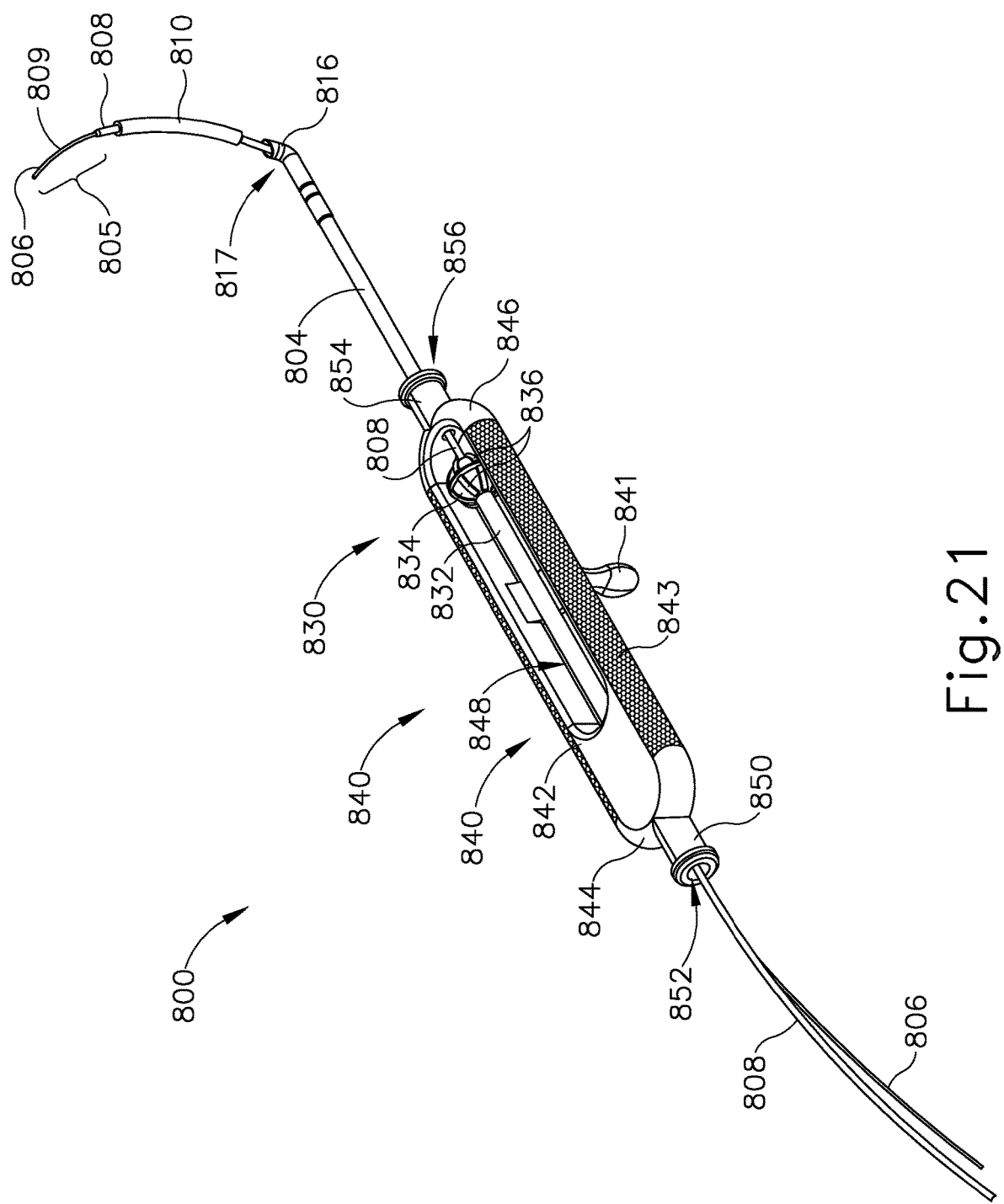
FIG. 21 depicts a perspective view of the instrument of FIG. 20, with the dilation catheter and guidewire advanced to a distal position.
Figure 22:
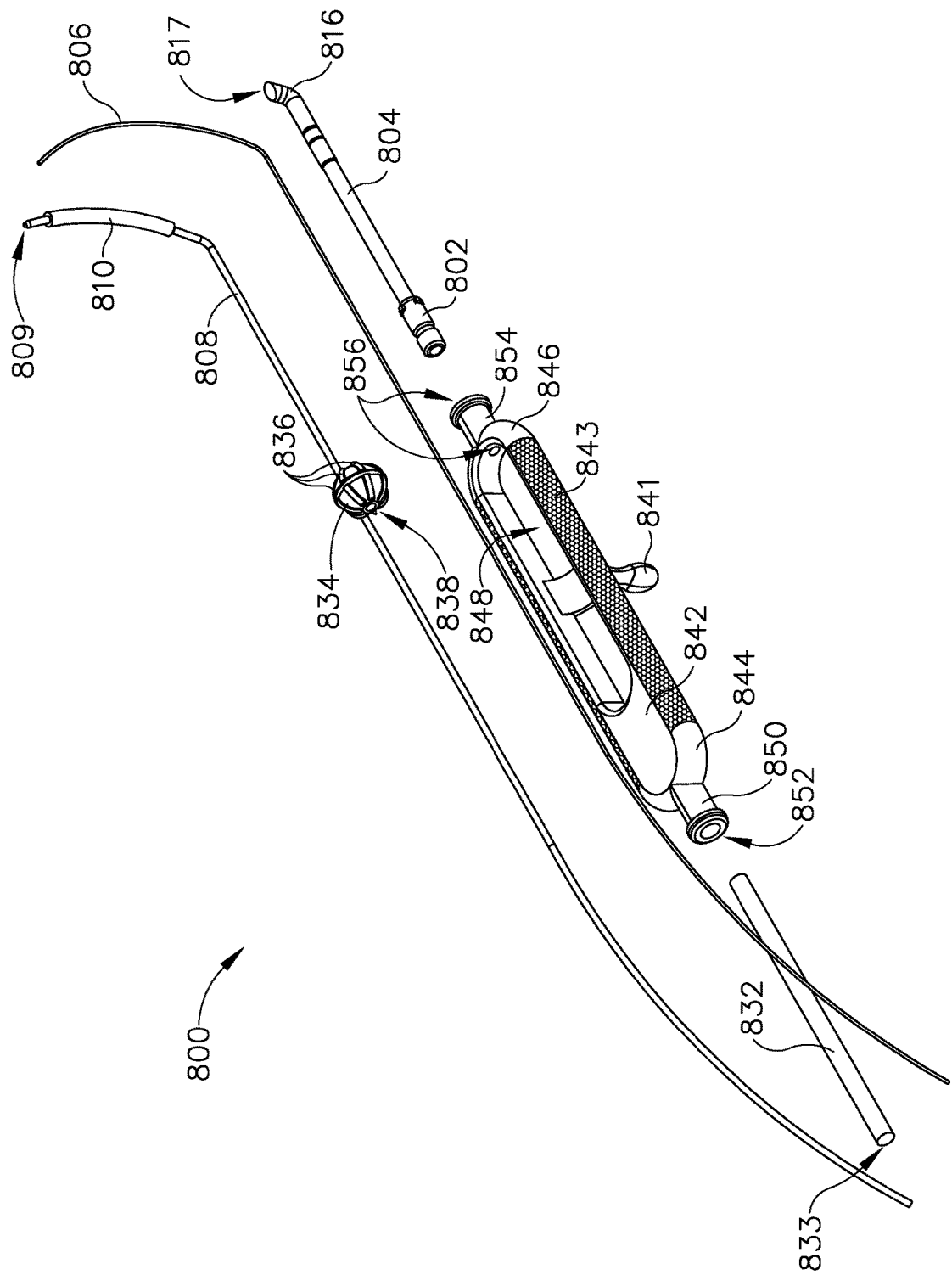
FIG. 22 depicts an exploded perspective view of the instrument of FIG. 20.

FIGS. 20-22 show an exemplary alternative instrument (800) that may also provide both unitary rotation and unitary longitudinal translation of a guidewire and a dilation catheter. Instrument (800) of this example includes a unitary actuation assembly (830), a handle assembly (840), a guidewire (806), and a dilation catheter (808). As will be described in greater detail below, unitary actuation assembly (830) is capable of fixing to guidewire (806) and dilation catheter (808) together. Additionally, unitary actuation assembly (830) is capable of unitarily rotating and unitarily translating guidewire (806) and dilation catheter (808) relative to handle assembly (840). Guidewire (806) may be substantially similar to guidewire (50, 106) described above, with differences described below. Similarly, dilation catheter (830) may be substantially similar to dilation catheter (20, 108) described above, with differences described below.

Dilation catheter (830) includes an inflatable balloon (810), which may be substantially similar to inflatable balloon (110) described above. Dilation catheter (808) defines a first inner lumen and a second inner lumen, which are fluidly isolated from one another. First inner lumen of dilation catheter (808) distally terminates in balloon (810). Proximal end of dilation catheter (808) may include an inflation port in fluid communication with first inner lumen, similar to inflation port (111) described above. Therefore, inflation port may be coupled with a fluid source to provide selective inflation of balloon (810) in accordance with the teachings herein. The second inner lumen of dilation catheter (808) extends all the way to open distal end (809) of dilation catheter (808) and provides a passageway to slidable receive guidewire (806) as further described below.

Handle assembly (840) includes a body (842), a guide catheter (804), and a detachable guide tip (816). Body (842) has a proximal portion (844), a distal portion (846), a proximally extending neck (850), a distally extending neck (854), a finger anchoring peg (841), and a textured gripping portion (843). Body (842) is sized and shaped such that instrument (800) can be manipulated and operated by a user in a convenient and efficient single-handed manner if so desired, with finger anchoring peg (841) promoting gripping of handle assembly (840) with a single hand. While the current example shows one finger anchoring peg (841), any suitable number of finger anchoring pegs (841) may be used as would be apparent to one having ordinary skill in the art in view of the teachings herein. Of course, finger anchoring pegs (841) are entirely optional.

Textured gripping portion (843) is placed to provide increased friction between the hand of a user and body (842). Therefore, a user may possess greater control of instrument (800) without having to worry about instrument (800) slipping from the hand of a user. Any suitably textured pattern or material may be used for textured gripping portion (843) as would be apparent to one having ordinary skill in the art in view of the teachings herein. Of course, textured gripping portion (843) is entirely optional.

Body (842) defines a slot (848) between proximal portion (844) and distal portion (846). Slot (848) is dimensioned to house a portion of unitary actuation assembly (830). Body (842) also defines a proximal channel (852) and a distal channel (856). Proximal channel (852) extends through proximally extending neck (850) and proximal portion (844), thereby providing a pathway between the proximal end of proximally extending neck (850) and slot (848). Similarly, distal channel (856) extends through distally extending neck (854) and distal portion (846), thereby providing a pathway between the distal end of distally extending neck (854) and slot (848). As will be described in greater detail below, proximal channel (852) and slot (848) are configured to slidably house portions of unitary actuation assembly (830) while proximal channel (852), slot (848) and distal channel (856) are configured to slidably house portions of guidewire (806) and guide catheter (804).

In the present example, guide catheter (804) may be substantially similar to guide catheter (104) described above, with differences described below. Therefore, guide catheter (804) defines an inner lumen (i.e., inner passage). Guide catheter (804) includes a proximal coupling portion (802), which may selectively attach to distal neck portion (854) via distal channel (856) such that guide catheter (804) is fixed relative to body (842). Proximal coupling portion (802) may attach with distal neck portion (854) such that a user may rotate guide catheter (804) relative to handle assembly (840) about the longitudinal axis defined by guide catheter (804) before fixing guide catheter (804) relative to body (842). Guide catheter (804) may attach to body (842) in any suitable manner as would be apparent to one having ordinary skill in the art in view of the teaching herein.

Detachable guide tip (816) may be substantially similar to detachable guide tip (116) described above. Detachable guide tip (816) includes an open distal end (817) dimensioned to allow inflatable balloon (810), guidewire (806), and dilation catheter (808) to exit. Detachable guide tip (816) may be removably attached to, and detached from, the distal end of guide catheter (804). Detachable tips (816) can be attached and detached from instrument (800) at any suitable location. An array of detachable tips (816) may be available for selection by the user, with different detachable tips (816) having different bend angles and/or other different configurations to promote access to different anatomical structures. It should be understood that guide catheter (804) may have an integral tip that is pre-bent, malleable, or otherwise formed such that a separate, detachable guide tip (816) may be omitted from instrument (800). In other words, detachable guide tip (816) is merely optional.

Unitary actuation assembly (830) includes a unitary control knob (834) and a sliding connector shaft (832) fixed to unitary control knob (834). Sliding connector shaft (832) defines a lumen (833) extending through shaft (832). The end of sliding connector shaft (832) fixed to unitary control knob (834) defines a distal slit shaped opening (831). Lumen (833) is dimensioned to house a portion of guidewire (806) and dilation catheter (808). Distal slit shaped opening (831) is dimensioned to provide a path for guidewire (806) to exit lumen (833) transversely, as will be described in greater detail below.

Sliding connector shaft (832) is slidably and rotatably housed within proximal channel (852) of body (842). Sliding connector shaft (832) is dimensioned to fit within proximal channel (852) in order to promote rigid stability of unitary control knob (834) in lateral and vertical directions. In other words, sliding connector shaft (832) is dimensioned small enough such that shaft (832) may translate within channel (852), yet shaft (832) is dimensioned large enough such that when a user pushes knob (834) and/or shaft (832) in a lateral or vertical direction, unitary actuation assembly (830) remains substantially stable in the lateral and vertical directions relative to handle assembly (840).

Unitary control knob (834) defines a channel (838) that is configured to receive dilation catheter (808) and sliding connector shaft (832). Sliding connector shaft (832) may be unitarily fixed to control knob (834) by an interference fit between shaft (832) and channel (838), with use of adhesives, or any other suitable manner as would be apparent to one having ordinary skill in the art in view of the teachings herein. In part because unitary control knob (834) is fixed to sliding connector shaft (832), unitary control knob (834) is capable of rotating about the longitudinal axis defined by sliding connector shaft (832) and longitudinally translating within slot (848) defined by body (842).

Additionally, unitary control knob (834) includes a plurality of longitudinal tracks (836) that travel along the surface of control knob (834) from a first opening of channel (838) to a second opening of channel (838).

As seen in FIGS. 20-21, guidewire (806) and dilation catheter (808) enter proximal channel (852) separately through proximally extending neck (850). Guidewire (806) and dilation catheter (808) also enter lumen (833) of sliding connector shaft (832) separately. While dilation catheter (808) travels through channel (838) of unitary control knob (834), guidewire (806) exits lumen (833) via distal slit shaped opening (831) and travels along longitudinal track (836). Guidewire (806) is confined to the pathway provided by longitudinal track (836) and eventually enters slit shaped opening (807) defined by dilation catheter (808). Slit shaped opening (807) is connected to second lumen on dilation catheter (808). Therefore, as guidewire (806) enters second lumen of dilation catheter (808) through slit shaped opening (807), guidewire (806) may also travel through second lumen to exit open distal end (809) of dilation catheter (808).

Dilation catheter (808) may be selectively fixed to unitary actuation assembly (830) through an interference fit between channel (838) of unitary control knob (834) and the outer diameter of dilation catheter (808). A user may feed one end of dilation catheter (808) through channel (838) of control knob (834) and overcome the frictional braking force caused by the interference fit of channel (838) and dilation catheter (808) by pulling dilation catheter (808) while holding control knob (834). However, the frictional braking force caused by the interference fit of channel (838) and dilation catheter (808) may be strong enough such that control knob (834) and dilation catheter (808) unitarily rotate and translate when a user manipulates control knob (834) relative to handle assembly (840). Because control knob (834) is capable of rotating and translating relative to handle assembly (840), dilation catheter (808) is also capable of rotating and translating relative to handle assembly (840). Of course, dilation catheter (808) may be permanently or selectively fixed to unitary actuation assembly (830) through any other suitable means apparent to one having ordinary skill in the art in view of the teachings herein, such as through use of adhesives.

Guidewire (806) may be selectively fixed to unitary actuation assembly (830) through a snap fitting connection between guidewire (806) and longitudinal track (836) of unitary control knob (834). For example, a user may feed guidewire (806) through distal slit shaped opening (831), longitudinal track (836), slit shaped opening (807), and out distal open end (809) to a desired distance defining extending portion (805). Extending portion may be substantially similar to extending portion (307) mentioned above. A user may then grasp guidewire (806) on opposite ends of unitary control knob (834) and press down on guidewire (806) until guidewire (806) snaps into longitudinal track (836). The snap fitting between guidewire (806) and longitudinal track (836) may provide a sufficient frictional breaking force such that guidewire (806) is effectively fixed relative to unitary control knob (834).

If a user then decides to either remove guidewire (806) from the rest of instrument (800) or adjust the length of extending portion (805), a user may grasp guidewire (806) on opposite ends of unitary control knob (834) and pull guidewire (806) away from knob (834). Guidewire (806) may then snap out of longitudinal track (836) such that guidewire (806) is not longer fixed relative to unitary control knob (834). Guidewire (806) may then be adjusted or a removed. Of course, guidewire (806) may be selectively fixed to unitary actuation assembly (830) in any other suitable manner as would be apparent to one having ordinary skill in the art in view of the teachings herein. It should be understood from the foregoing that the user may selectively adjust and selectively secure the longitudinal position of guidewire (806) relative to unitary control knob (834) to thereby selectively adjust and selectively fix the length of extending portion (805). The user may select the length of extending portion (805) based on the targeted anatomical structure and/or based on other considerations as will be apparent to those of ordinary skill in the art in view of the teachings herein.

In the present example, unitary control knob (834) includes a plurality of longitudinal tracks (836). However, unitary control knob (834) may have a single longitudinal track (836). Alternatively, each longitudinal track (836) in the plurality of longitudinal tracks (836) may be dimensioned to snap fit with a different diameter of guidewire (806). Therefore, unitary actuation assembly (830) may be able to selectively couple with a plurality of different guidewires (806) having different diameters.

Because guidewire (806) and dilation catheter (808) may be fixed to control knob (834), guidewire (806) and dilation catheter (808) may unitarily rotate and translate relative to handle assembly (840) in response to a user manipulating unitary actuation assembly (830). In particular a user may translate unitary actuation assembly (830) relative to handle assembly (840) such that the distal end of guidewire (806) and open distal (809) of dilation catheter (808) are housed within either guide tip (816) or guide catheter (804). A user may then translate unitary actuation assembly (830) in the distal direction until dilation balloon (810) exits open distal end (817) of guide tip (816). Additionally, a user may rotate unitary control knob (834) about the longitudinal axis defined by sliding connector shaft (832) in order to unitarily rotate dilation catheter (808) and guidewire (806) by their respective longitudinal axes.

The foregoing discussion provides various examples of how a guidewire (106, 806) and a dilation catheter (108, 808) may be fixedly secured together to provide unitary rotation and translation of the guidewire (106, 806) with the dilation catheter (108, 808). Similarly, the foregoing discussion provides various examples of how a guidewire (106, 806) and a dilation catheter (108, 400, 808) may be fixedly secured together such that a distal portion of guidewire (106, 806) fixedly protrudes distally from the distal end of dilation catheter (108, 808). While these examples are provided in the specific context of instruments (300, 800), it should be understood that the same teachings may be applied to a variety of other instruments. By way of example only, the same teachings may be readily incorporated into a Relieva® Spin Balloon Sinuplasty™ System by Acclarent, Inc. of Irvine, Calif. As another merely illustrative example, the same teachings may be readily incorporated into a Relieva® Scout Sinus Dilation System by Acclarent, Inc. of Irvine, Calif. Other suitable instruments into which these teachings may be incorporated will be apparent to those of ordinary skill in the art.

V. Exemplary Locking Mechanism for Fixing Guidewire to Dilation Catheter

As noted above, it may be desirable in some instances to utilize a guidewire that is fixedly secured to a dilation catheter. It may be desirable in some instances to spin, advance, and retract the guidewire and the dilation catheter as a unit, with one rotation knob and without an additional separate movement actuator (e.g., dilation catheter movement actuator (114)) for the dilation catheter. FIGS. 12A-12C show a dilation catheter (400) that provides a fixedly integrated guidewire (106). Dilation catheter (400) of this example is substantially similar to dilation catheter (108) described above, though dilation catheter (400) of this example is particularly configured for dilation of a Eustachian tube. By way of example only, in some versions dilation catheter (400) is constructed and operable in accordance with at least some of the teachings of U.S. Pub. No. 2013/0274715, entitled "Method and System for Eustachian Tube Dilation," published on Oct. 17, 2013, now abandoned, the disclosure of which is incorporated by reference herein; and/or U.S. Pub. No. 2015/0374963, entitled "Vent Cap for a Eustachian Tube Dilation System," published Dec. 31, 2015, issued as U.S. Pat. No. 10,350,396 on Jul. 16, 2019, the disclosure of which is incorporated by reference herein. It should therefore be understood that dilation catheter (400) may be used in combination with the guide catheters described in U.S. Pub. No. 2013/0274715, now abandoned and U.S. Pub. No. 2015/0374963, issued as U.S. Pat. No. 10,350,396 on Jul. 16, 2019 to dilate a Eustachian tube as described in U.S. Pub. No. 2013/0274715, now abandoned and U.S. Pub. No. 2015/0374963, issued as U.S. Pat. No. 10,350,396 on Jul. 16, 2019.

Dilation catheter (400) of the present example generally includes an elongate shaft (402) having a proximal end (414) and a distal end (418). Dilation catheter (400) further includes a proximal connector (406) on proximal end (414); and a balloon (404) on distal end (418) of elongate shaft (402). Balloon (404) may be a polymer balloon (compliant, semi-compliant, or non-compliant). In some versions, balloon (404) comprises a suitable non-compliant material such as but not limited to polyethylene terephthalate (PET), PEBAX® (polyether block amide), nylon or the like. Dilation catheter (400) may include any size of balloon including, but not limited to, balloons of 2 mm to 8 mm in diameter or of between about 5 mm and 6 mm (when inflated) and 12 mm to 24 mm in working length (for example 2 mm×12 mm, 3.5 mm×12 mm, 5 mm×16 mm, 5 mm×24 mm, 6 mm×16 mm, 6 mm×20 mm, 6 mm×24 mm, 7 mm×16 mm and 7 mm×24 mm). Dilation catheter (400) generally includes a proximally located connection (430) for inflating/activating balloon (404) by communicating a pressurized medium (e.g., saline) to balloon (404).

Balloon (404) may be expanded to dilate the Eustachian tube of a person undergoing treatment after balloon (404) is placed in a desirable location in the Eustachian tube. For example, the opening area of the Eustachian tube includes a pharyngeal ostium, and dilation catheter (400) may be advanced through a guide catheter (not shown) to position balloon (404) in the pharyngeal ostium. An endoscope may be used to assist in positioning dilation catheter (400). The endoscope may be advanced through the nasal passage to view dilation catheter (400). A marker (408) on shaft (402) can be viewed from the endoscope to approximate a location of balloon (404) relative to the opening of the Eustachian tube (e.g., pharyngeal ostium) based on a distance of marker (408) from a proximal end of balloon (404). Accordingly, dilation catheter (400) can be moved to place marker (408) in a desirable location before expansion of balloon (404) in the Eustachian tube.

Dilation catheter (400) further includes an actuator (410). Actuator (410) has a proximal side (420) and a distal side (422). In the example shown in FIG. 12A, actuator (410) is secured by an adhesive to elongate shaft (402). The portion (440) of elongate shaft (402) that is distal of actuator (410) is sufficiently stiff to be guided through the nasal cavity and into the Eustachian tube and is constructed of stainless steel and preferably includes a stainless steel hypotube. The portion (438) of elongate shaft (402) that is proximal of actuator (410) and the portion (450) that is distal to portion (440) is more flexible than the portion (440) and is constructed of a polymeric material including but not limited to PEBAX® (polyether block amide). In this way, proximal portion (438) of elongate shaft (402) will not interfere with the endoscope described above as it is advanced through the nasal passage, such that dilation catheter (400) can be easily viewed. Actuator (410) allows for easy, ergonomic one-handed advancement of dilation catheter (400) through a guide catheter (not shown) and into the Eustachian tube. Actuator (410) may be used to advance or retract in alternative ways including but not limited to use of the thumb, the index finger, or a combination of fingers (e.g., the index and middle fingers) or the thumb and the index or middle finger.

The distal end (418) of balloon catheter (400) further includes a tip (412) and a flexible shaft portion (450) that is constructed of a polymeric material including but not limited to PEBAX® (polyether block amide) that extends from the distal end of elongate shaft (402) to the proximal end of balloon (404). In the example shown in FIG. 12A, tip (412) is a bulbous polymeric blueberry shaped, atraumatic tip and is about 1.5 mm to about 2 mm in length, with an outer diameter of between about 2 mm and about 3 mm. The smoothness and roundness of tip (412) facilitates advancement of the balloon catheter (400) by helping it glide smoothly through the Eustachian tube. Tip (412) further acts as a safety stop. The isthmus of the Eustachian tube is approximately 1 mm in diameter. Tip (412) diameter is larger than the outer diameter (433) of the elongate shaft (402) shown in cross-section in FIG. 12B such that tip (412) size will prevent balloon catheter (400) from passing through the isthmus into the middle ear Elongate shaft (402) contains adjacent dual lumen (432, 434) tubing (see FIG. 12B). By adjacent dual lumen tubing, it is intended that the lumens (432, 434) are next to each other but are spaced apart, one from the other. Inflation lumen (432) is used for inflation of balloon (404) with water, contrast medium, or saline through inflation port (430) to a pressure of between about 3 and about 15 atmospheres, or of between about 6 and about 12 atmospheres. Injection lumen (434) permits the optional injection of water, medicament, or the introduction of a guidewire (e.g. guidewire (106)) through injection port (436) at proximal end (416) of proximal connector (406). In order to ensure that inflation port (430) is used for balloon (404) inflation only, inflation port (430) and injection port (436) may optionally have different type connectors. For example, inflation port (430) may be a female connector whereas injection port (436) is a male connector or vice versa. Alternatively, injection port (436) may have a right-handed thread connector and inflation port (430) may have a left-handed thread connector or vice versa.

As shown in FIGS. 12A-12C, dilation catheter (400) may receive guidewire (106) therethrough by inserting guidewire (106) through port (436) of elongate shaft (402) and advancing guidewire (106) until a portion (431) extends from tip (412) of balloon (404). A locking mechanism (409) disposed at proximal end (414) of elongate shaft (402) is configured to lock and hold guidewire (106) at the desired length and affix guidewire (106) to dilation catheter (400). Thus, dilation catheter (400) and guidewire (106) become a fixed unit and may be manipulated as a unit through actuator (410). The user may manipulate actuator (410) to spin, advance, and retract the fixed unit of dilation catheter (400) and guidewire (106) unitarily through a guide catheter (not shown).

Locking mechanism (409) is sized and configured to fit or connect with proximal end (416) of proximal connector (406). Specifically, locking mechanism (409) is configured to mate with injection port (436) of proximal connector (406). This allows guidewire (106) to pass through injection lumen (434) and extend past distal end (418) of dilation catheter (400) for use in guiding guide catheter (104) into the desired position within the anatomy of a person undergoing treatment. Alternatively, locking mechanism (409) may be configured to simply abut proximal connector (406) and not mate in a fixed manner. In addition to mating or abutting with proximal connector (406), locking mechanism (409) is configured to selectively lock onto guidewire (106) at the user's discretion. Locking mechanism (409) may comprise a luer lock, a collet style lock, or any other suitable feature to firmly secure locking mechanism (409) with guidewire (106) to form a fixed unit.

The user may configure the length of portion (431) as desired and as appropriate for the underlying treatment or procedure. For example, for the frontal sinuses, portion (431) of guidewire (106) may be fixed at a longer length, and for the maxillary sinuses, portion (431) of guidewire (106) may be fixed at a shorter length. Inasmuch as guidewire (106) and dilation catheter (400) are fixed and move as a unit, the user may use an index, middle finger, or thumb to press actuator (410) to advance or retract the unit and manipulate the positioning of portion (431). The rotation or spin of the fixed wire unit may be done by rolling the finger alongside of the shaft of dilation catheter (400) or actuator (410).

Some anatomy systems may benefit greatly from the use of guidewire (106) for properly positioning dilation catheter (400) in the underlying anatomy. For example, certain sinus procedures may benefit from distal portion (431) of guidewire (106) protruding from the distal end of dilation catheter (400). Conversely, other anatomy systems may not benefit from the user of guidewire (106). For example, certain Eustachian tube procedures may be better suited for the absence of guidewire (106) at the outermost end of dilation catheter (400). Locking mechanism (409) empowers the user with the ability and discretion to either apply or remove guidewire (106) from dilation catheter (400) and customize the overall treatment accordingly.

It should be understood from the foregoing that the combination of dilation catheter (400) and guidewire (106) may be selectively adjusted for use in Eustachian tube dilation procedures and sinus dilation procedures. In some versions, to further accommodate use in such different anatomical structures, dilation catheter (400) may include features that enable the operator to selectively expand (for Eustachian tube dilation procedures) and contract (for sinus dilation procedures) tip (412). By way of example only, tip (412) may be selectively expanded and contracted in accordance with at least some of the teachings of U.S. patent application Ser. No. 14/834,968, entitled "Dilation Catheter with Expandable Stop Element," filed Aug. 25, 2015, issued as U.S. Pat. No. 10,512,763 on Dec. 24, 2019, the disclosure of which is incorporated by reference herein.

VI. Exemplary Dilation Catheter With Locking Mechanism and Stabilizing Tube

As shown in FIGS. 13-15, a stabilizing tube assembly (500) includes a stabilizing tube (501), a locking mechanism (503), and an actuator (505). Stabilizing assembly (500) is configured to be selectively and fixedly secured to a guidewire (106) to provide rigidity to guidewire (106) and allow the user to actuate or advance guidewire (106) through a guide element such as guide catheter (104) or dilation catheter (400). Stabilizing tube (501) of the present example comprises a rigid tubular member such as a hypotube or equivalent with actuator (505) mounted on the proximal end thereof. As shown in FIG. 13, actuator (505) is coupled with a locking mechanism (503) to allow the user to lock stabilizing tube assembly (500) to guidewire (106) to form a fixed guidewire unit, whereby the guidewire (106) may be rotated and translated by manipulating actuator (505). The user may engage locking mechanism (503) by pressing or otherwise manually manipulating locking mechanism (503) to squeeze down or clamp guidewire (106) to hold stabilizing tube assembly (500) firmly to guidewire (106).

As shown in FIG. 14, stabilizing tube (501) is configured to receive guidewire (106) therethrough and sized to provide a small tolerance with respect to the inner diameter of stabilizing tube (501) and the outer diameter of guidewire (106). The small tolerance allows guidewire (106) to spin and move distally and proximally within stabilizing tube (501) and, if need be, dilation catheter (400) or guide catheter (104), while simultaneously preventing guidewire (106) from binding or storing twist or spin energy. Stabilizing tube (501) also thus provides rigidity to the length of guidewire (106) extending through stabilizing tube (501).

Locking mechanism (503) may comprise a luer lock, a collet style lock, or any other suitable kind of mechanism to firmly secure guidewire (106) with stabilizing assembly (500) to form a fixed wire unit. Stabilizing tube (501) provides rigidity to guidewire (106) while actuator (505) and locking mechanism (503) allows the user to spin, advance, or retract guidewire (106) with a finger of the same hand that is holding guide catheter (104) or dilation catheter (400). The user may select the length of guidewire (106) extending distally from stabilizing tube (501) to fine tune the treatment. The selection of the length of guidewire (106) that protrudes distally from the distal end of stabilizing tube (501) may be based on the targeted anatomical structure and/or other considerations. It should be understood that the selection of the distally protruding length of guidewire (106), and the longitudinal fixation of guidewire (106) relative to stabilizing tube (501), may be performed before the medical procedure begins. It should also be understood that, in some versions, the length of guidewire (106) that protrudes distally from the distal end of stabilizing tube (501) may be adjusted during a medical procedure (e.g., when the procedure moves from one anatomical structure to another anatomical structure).

In some versions of stabilizing assembly (500), locking member (503) is provided in a generally centralized portion of actuator (505). As shown in FIG. 15, in some other versions, referred to as stabilizing assembly (500A), a locking member (507) is disposed on the outer surface of actuator (505) and may comprise a luer lock, a collet style lock, or any other suitable kind of mechanism to firmly secure guidewire (106) with stabilizing assembly (500A) to form a fixed wire unit. Other suitable forms that locking members (503, 507) may take, and other suitable positions where locking members (503, 507) may be located, will be apparent to those of ordinary skill in the art in view of the teachings herein.

VII. Exemplary Instrument With Rotatable Guide Catheter

Figure 16:
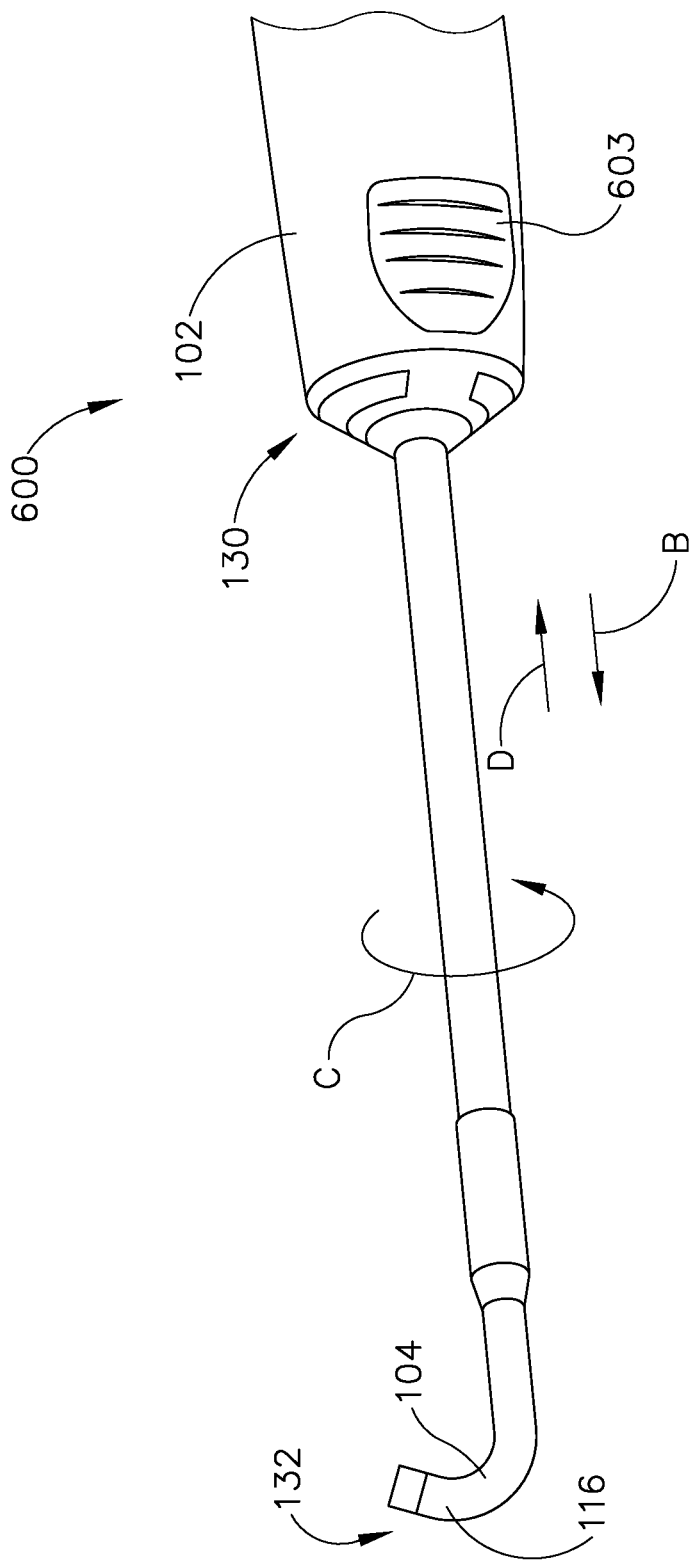
FIG. 16 depicts a perspective view of an exemplary guide instrument that may be used with the dilation catheter system of FIG. 1.

As noted above, it may be desirable in some instances to rotate guide catheter (104) relative to handle (102) for better placement within a particular anatomy. FIG. 16 shows an exemplary instrument (600) that is similar to instrument (100) of FIG. 2, with like elements having like numbering. It should be understood that instrument (600) may be readily incorporated into dilation catheter system (10). Guide catheter (104) of instrument (600) extends from proximal end (130) to distal end (132) and may be rotated about longitudinal axis (LA1) to configure guide tip (116) in a particular orientation. For example, as shown in FIG. 2, guide tip (116) may be oriented in a "tip up" position and rotated to a "tip down" position. In instrument (600), rotation of guide catheter (104) is accomplished by depressing a button (603) to unlock proximal end (130) of guide catheter (104) from handle (102); advancing guide catheter (104) from handle (102) in the direction of Arrow B; rotating guide catheter (104) in the direction of Arrow C to the desired orientation of guide catheter (104); and thereafter retracting guide catheter (104) in the direction of Arrow D back into handle (102).

In some versions of instrument (600), guide catheter (104) may be rotated relative to a handle (102) among various discrete, predetermined angular orientations about the longitudinal axis of guide catheter (104). The features (130, 603) that selectively lock the selected angular orientation of the guide catheter (104) may determine the number of discrete angular orientations that the guide catheter (104) may achieve. In some instances, this limited number of angular orientations may be insufficient or otherwise less than ideal to reach a targeted anatomical structure with guide catheter (104). It may therefore be desirable in some instances to provide an instrument similar to instrument (600) with an alternative structure for rotating guide catheter (104) in order to re-orient guide catheter (104) among a virtually infinite number of angular orientations, such that the available number of angular orientations is not some limited, predetermined number.

FIGS. 17A-19 show an exemplary dilation catheter instrument (700) that is capable of providing a virtually infinite number of guide catheter orientations, rather than a discrete, limited number of guide catheter orientations. Instrument (700) of this example comprises a handle (702), a guide catheter (704), and a cap (705). Cap (705) is fixedly secured to the proximal end of guide catheter (704). Guide catheter (704) extends along longitudinal axis (LA2) and has a proximal end (730) and a distal end (732). Handle (702) includes a first shoulder (707) and a spaced apart second shoulder (709) and defines a pocket (711) therebetween. Cap (705) includes a cap shoulder (713) that is sized to be slidably or movably received in pocket (711) and selectively advanced and retracted within pocket (711). Cap (705) defines a chamber (715) therein. Instrument (700) includes a coil spring (717) disposed in chamber (715). Coil spring (717) is configured to bear upon second shoulder (709) and cap (705) to resiliently bias cap (705) in the distal direction. The bias from spring (717) provides frictional engagement between cap shoulder (713) and second shoulder (709) to firmly hold guide catheter (704) in a particular angular orientation.

Locking teeth (not shown) may be provided on the abutting surfaces of cap shoulder (713) and second shoulder (709) to further lock the angular orientation of cap (705) (and, hence, guide catheter (704)) relative to handle (702). Locking teeth are merely optional, however, as the abutting surfaces of cap shoulder (713) and second shoulder (709) may press together to provide a frictionally secured interaction. Further, bias from spring (717) may not necessarily require the user to completely overcome the abutting contact between cap shoulder (713) and second shoulder (709).

Figure 17A:
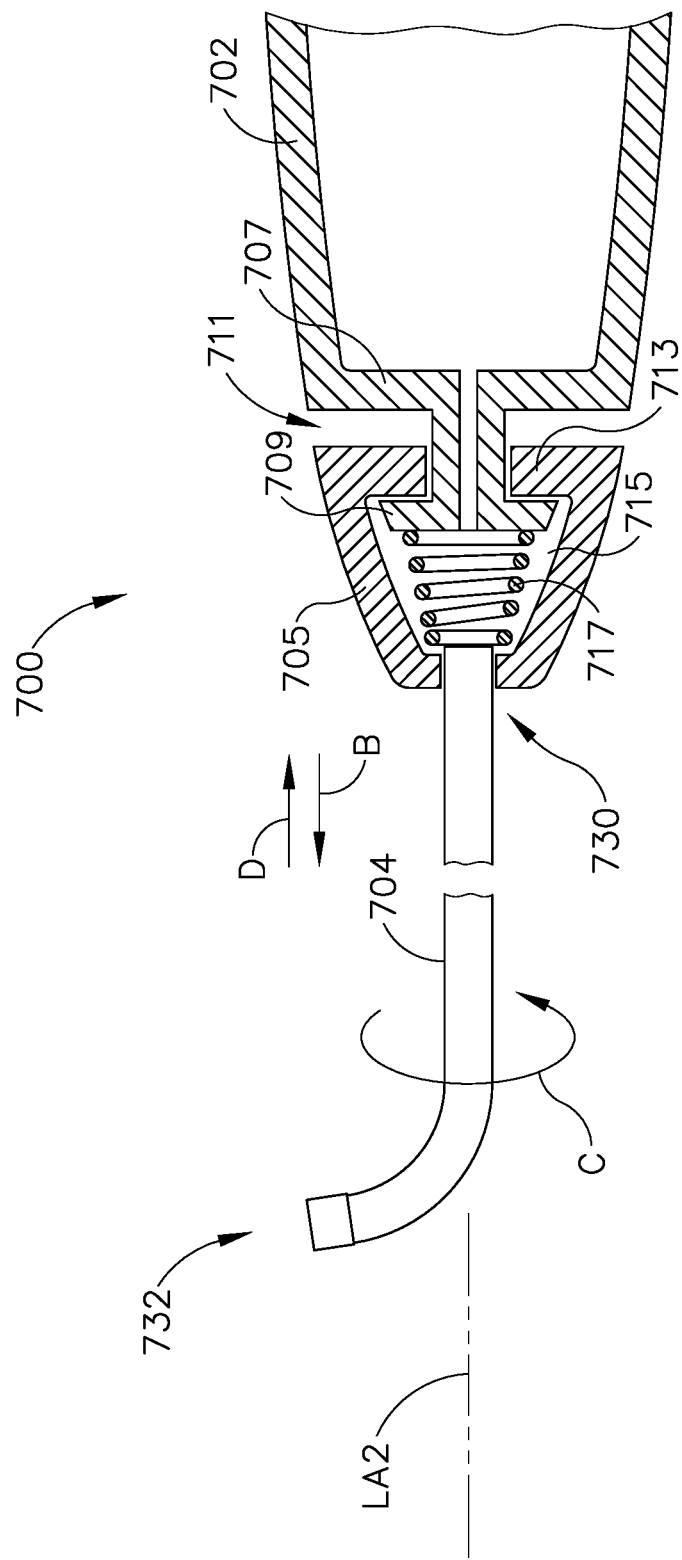
FIG. 17A depicts a cross-sectional side view of another exemplary guide instrument that may be used with the dilation catheter system of FIG. 1, with a coil spring and a cap in a first position and a guide catheter in a first orientation.
Figure 17B:
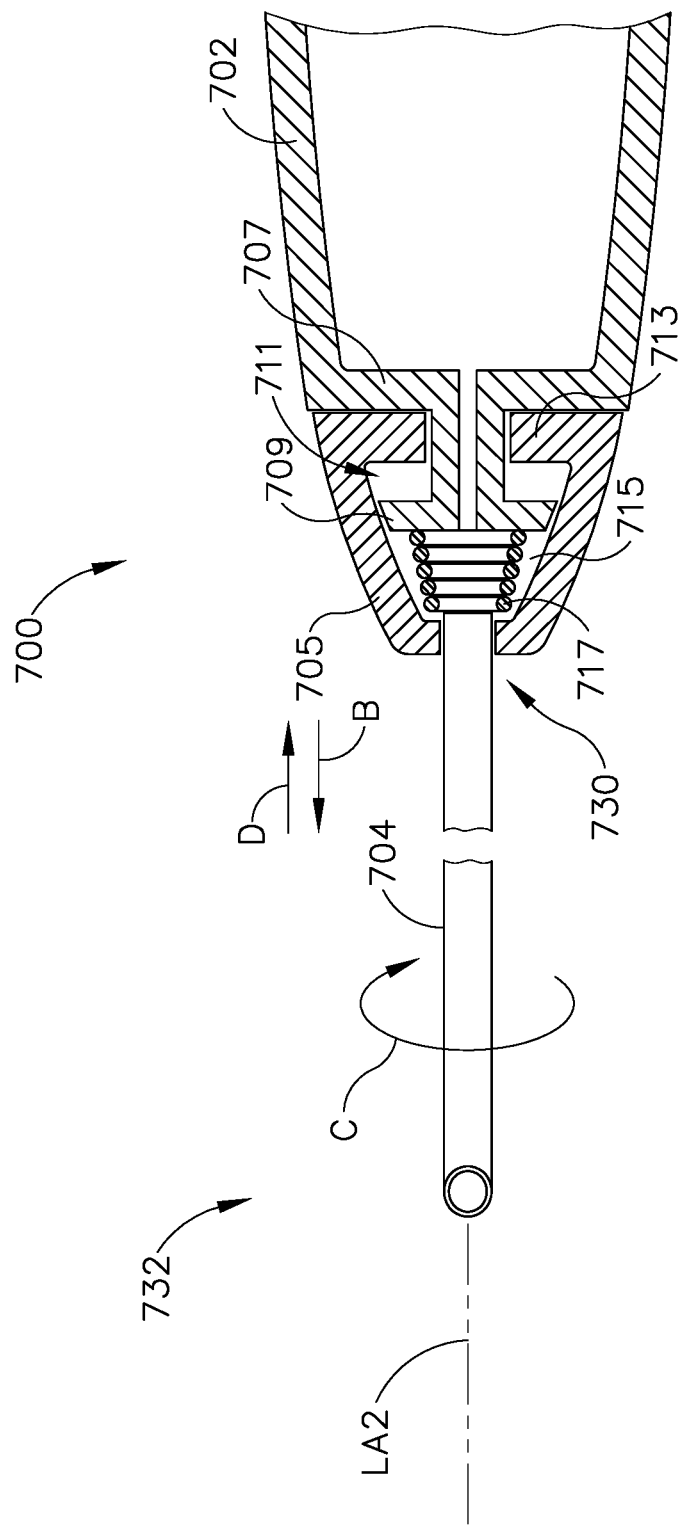
FIG. 17B depicts a cross-sectional side view of the instrument of FIG. 17A, with the cap moved to a second position and the guide catheter rotated to a second orientation.
Figure 17C:
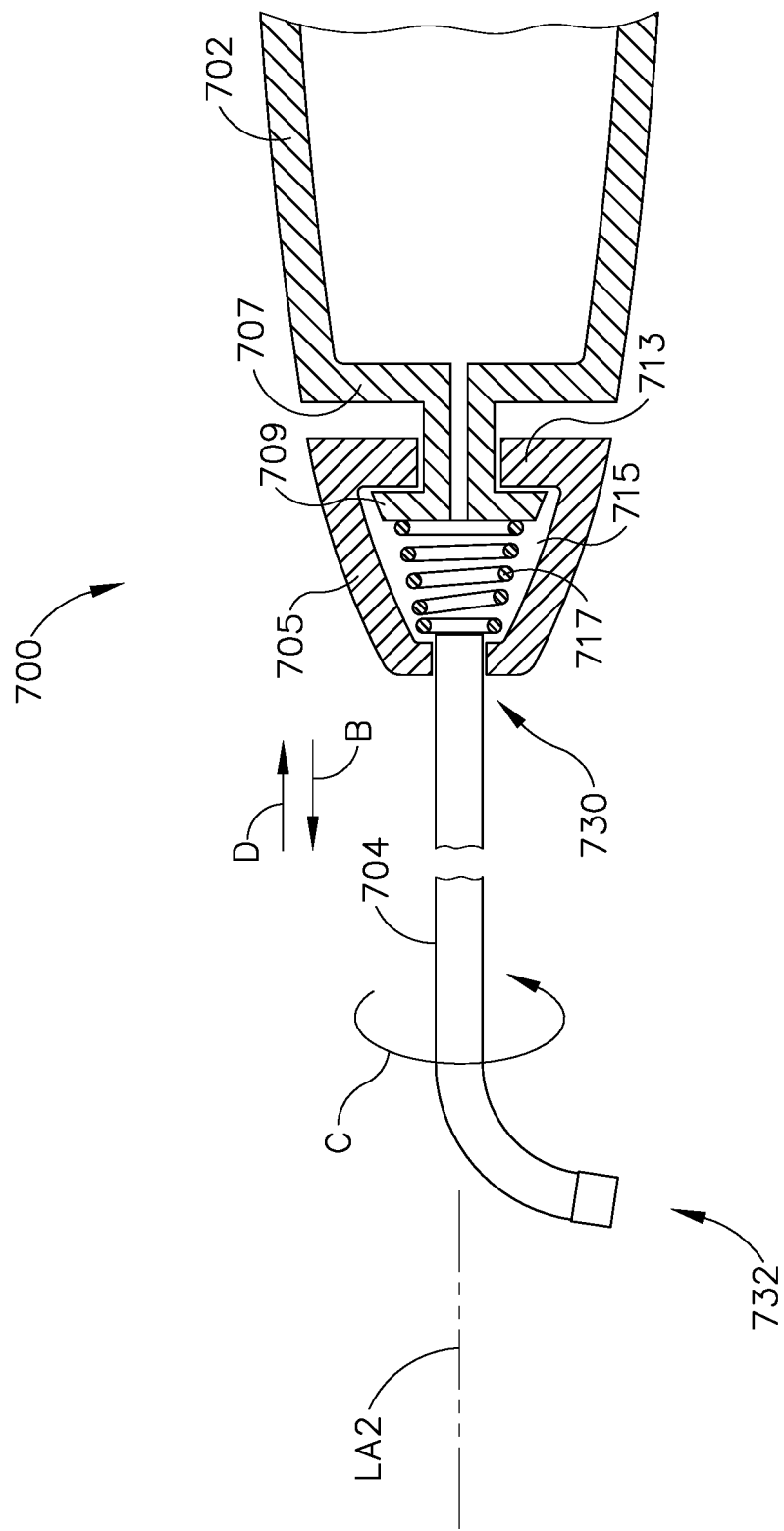
FIG. 17C depicts a cross-sectional view of the instrument of FIG. 17A, with the cap moved back to the first position and the guide catheter rotated to a third orientation.

As shown in FIGS. 17A-17C, to change the angular orientation of guide catheter (704), a user retracts guide catheter (704) and cap (705) in the proximal direction of Arrow D to overcome the bias from spring (717) in the distal direction of Arrow B. The movement of cap (705) in the direction of Arrow D disengages the frictional engagement (and/or meshing teeth engagement) between cap shoulder (713) and second shoulder (709) as cap (705) moves within pocket (711) in the proximal direction of Arrow D. As shown in FIG. 17B, cap shoulder (713) is moved proximally in the proximal direction of Arrow D within pocket (711), which compresses spring (717) and disengages cap shoulder (713) from second shoulder (709). With cap shoulder (713) disengaged from second shoulder (709), the user is free to rotate guide catheter (704) relative to handle (702) in the angular direction of Arrow C, or in the opposite angular direction, about the longitudinal axis (LA2). As shown in FIG. 17C, once guide catheter (704) is oriented to the user's preference, the user then releases cap (705) to allow cap (705) to move distally in the direction of Arrow B in accordance with the bias of spring (717). This reengages the frictional engagement (and/or meshing teeth engagement) between cap shoulder (713) and second shoulder (709) and firmly holds guide catheter (704) in the new angular orientation.

In some versions of instrument (700), cap shoulder (713) may abuttingly slide against second shoulder (709) and maintain constant contact therewith when manipulated by the user to allow the angular orientation of guide catheter (704) to change. Thus, the user need not necessarily retract guide catheter (704) and cap (705) in the proximal direction in order to re-orient guide catheter (704). In other words, the user may need to simply overcome the friction between cap shoulder (713) and second shoulder (709) in order to reposition the angular orientation of guide catheter (704). After the user completes the re-orientation of guide catheter (704), the friction between cap shoulder (713) and second shoulder (709) may maintain the adjusted orientation of guide catheter (704) during use of instrument (700) in a medical procedure.

Figure 18:
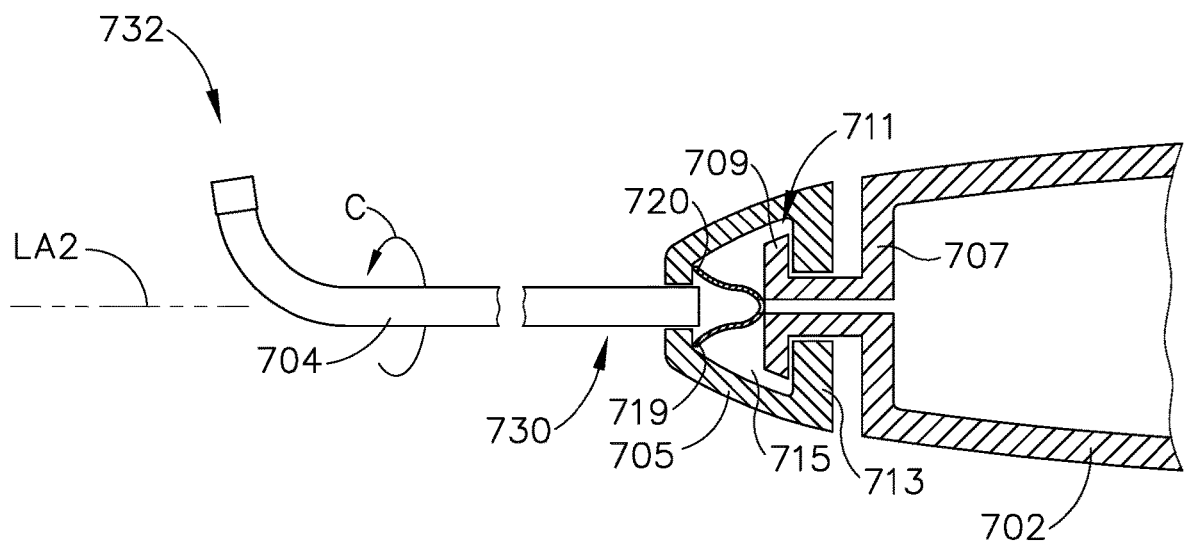
FIG. 18 depicts a cross-sectional view of the instrument of FIG. 17A with a wave spring in place of the spring.
Figure 19:
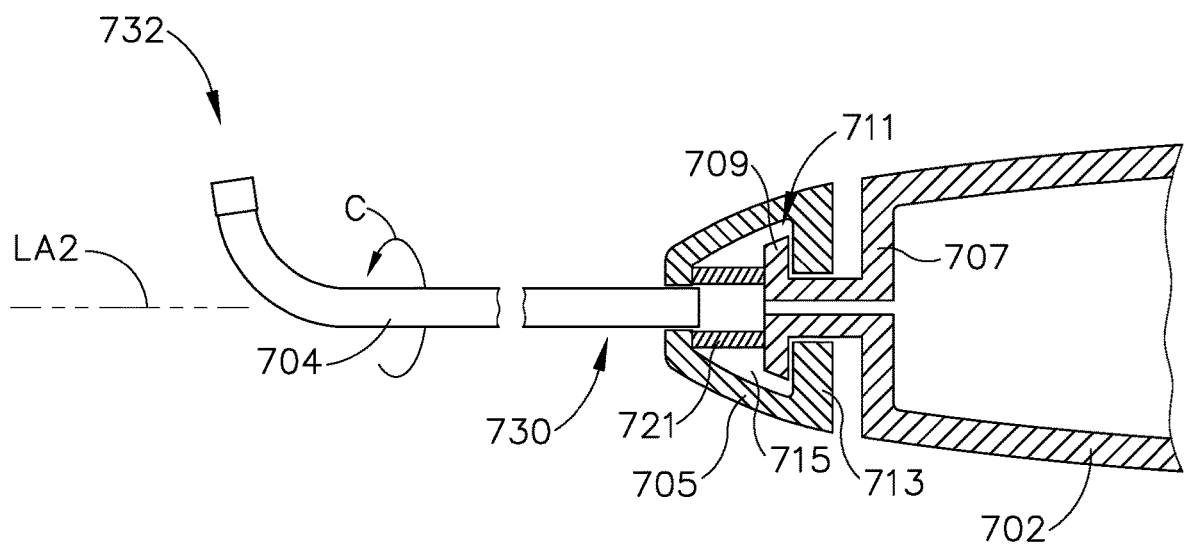
FIG. 19 depicts a cross-sectional view of the instrument of FIG. 17A with a rubber bushing in place of the spring.

As shown in FIGS. 18 and 19, the biasing member of instrument (700), embodied in FIGS. 17A-17C as coil spring (717), may be embodied in any other form of biasing member or biasing element. For example, as shown in FIG. 18, biasing member may comprise a spring washer or wave spring (719) that is configured to reside in chamber (715) and resiliently bias cap (705) in the distal direction. As a user presses cap (705) in the proximal direction, a portion (720) of spring washer or wave spring (719) deforms to allow the user to overcome the bias. As shown in FIG. 19, the biasing member may comprise a rubber bushing (721) that is configured to reside in chamber (715) and bias cap (705) in the distal direction. Rubber bushing (721) may be deformably compressed to enable a user to re-orient guide catheter (704) relative to handle (702), then resiliently urge cap (705) distally to re-engage shoulders (709, 713) to thereby lock the angular orientation of guide catheter (704) relative to handle (702). Other suitable components and features that may be used to provide a biasing element will be apparent to those of ordinary skill in the art in view of the teachings herein.

VIII. Exemplary Dilation Catheter System with Control Console

In system (10) described above, dilation catheter (20) is coupled with an inflator (40), while guidewire (50) is separately coupled with a light source (not shown), which is completely separate from inflator (40). In order to promote ease of use, it may be desirable to integrate the functionality of inflator (40) and the light source into a single base unit. In some versions, the base unit may be provided as a piece of capital equipment. One merely illustrative example of how this may be carried out is described in greater detail below.

Figure 23:
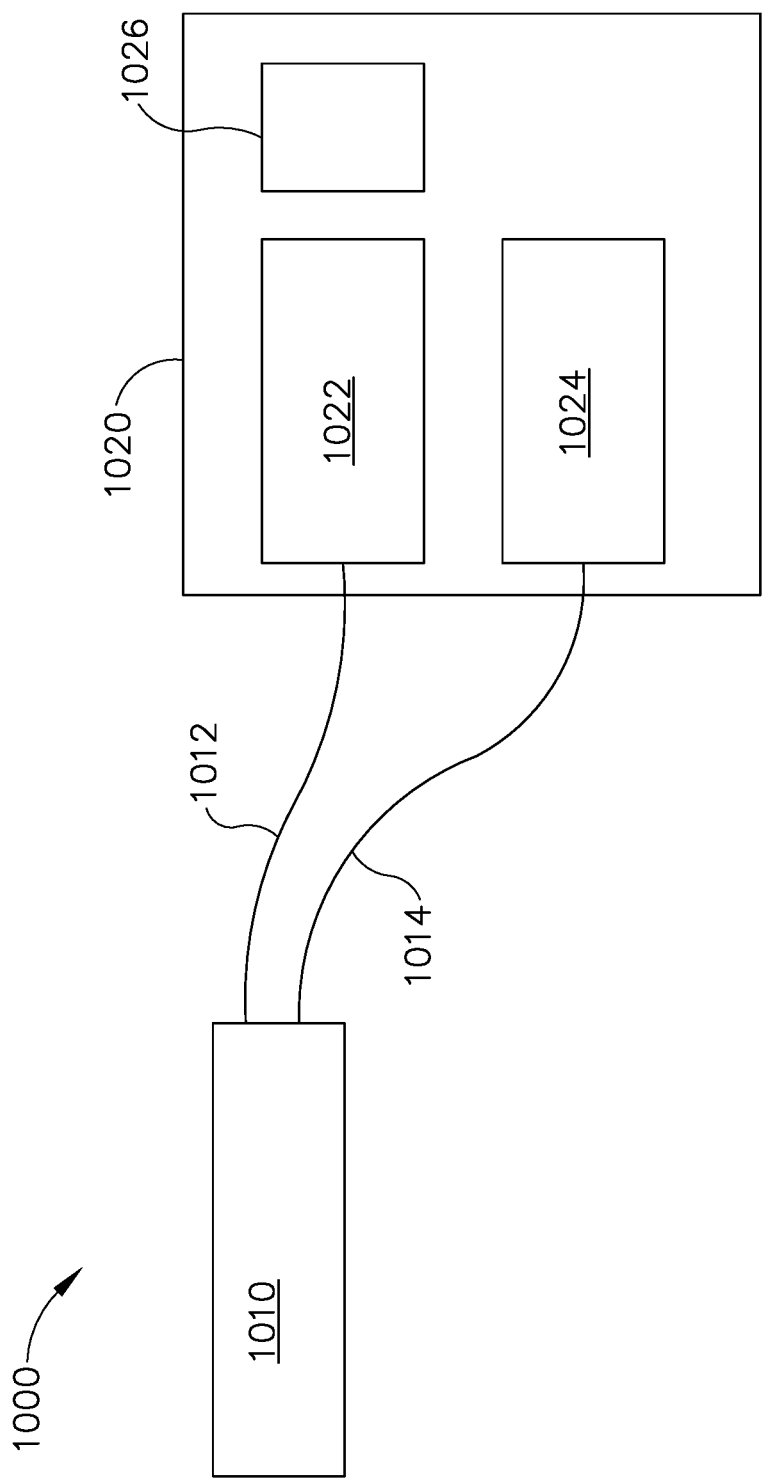
FIG. 23 depicts a schematic view of an exemplary alternative dilation catheter system.
Figure 24:
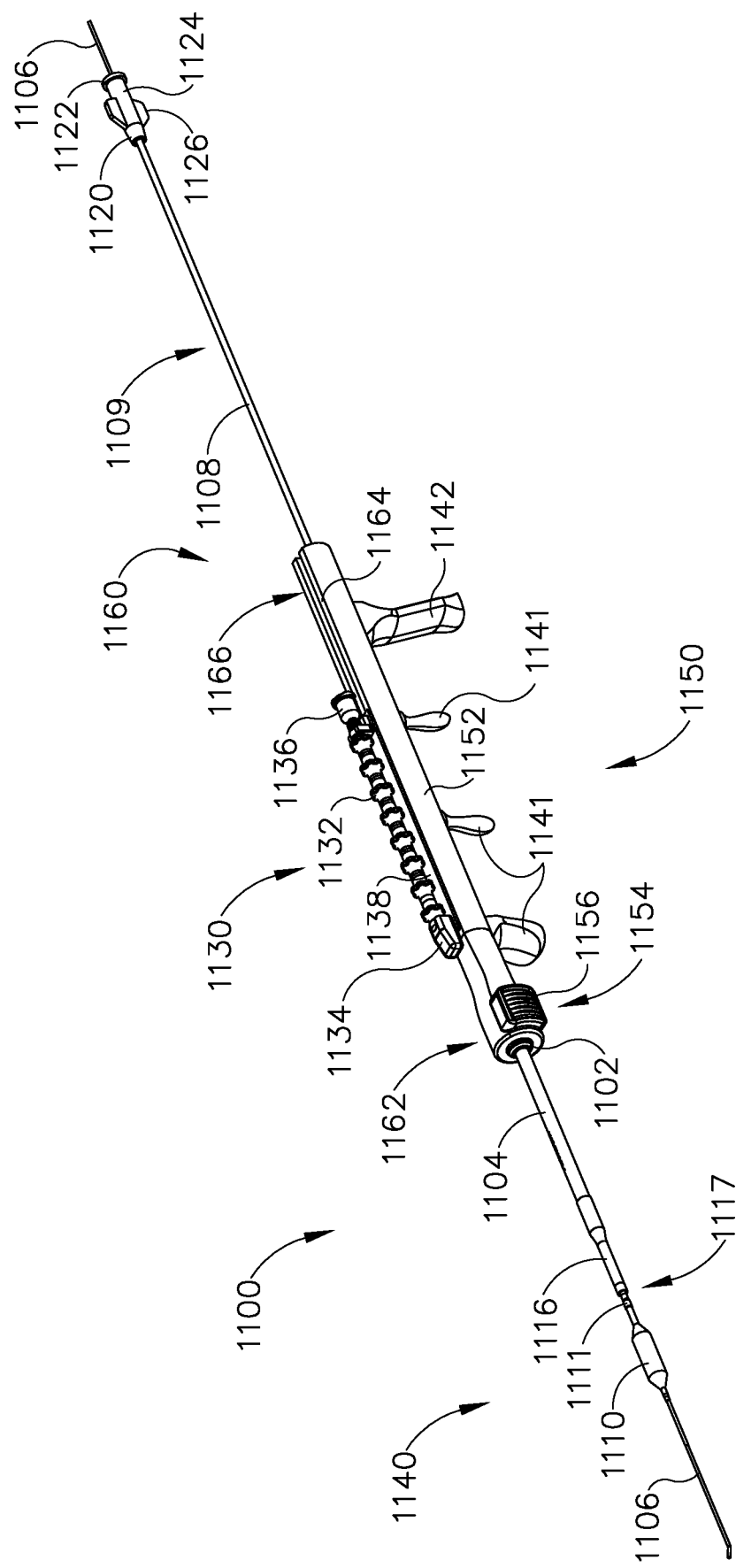
FIG. 24 depicts a perspective view of another exemplary alternative dilation catheter system.
Figure 25:
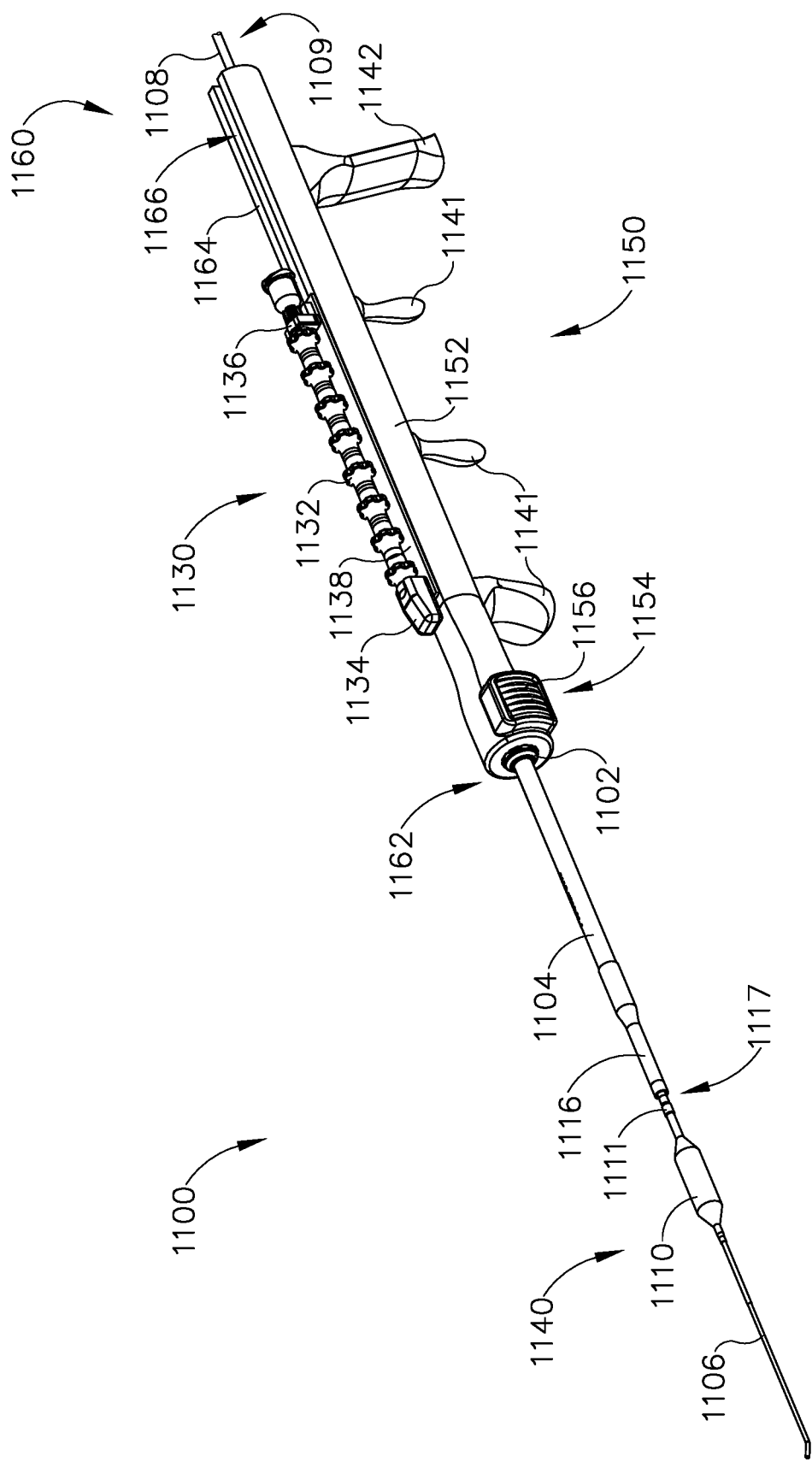
FIG. 25 depicts an enlarged perspective view of the dilation catheter system of FIG. 24.
Figure 26:
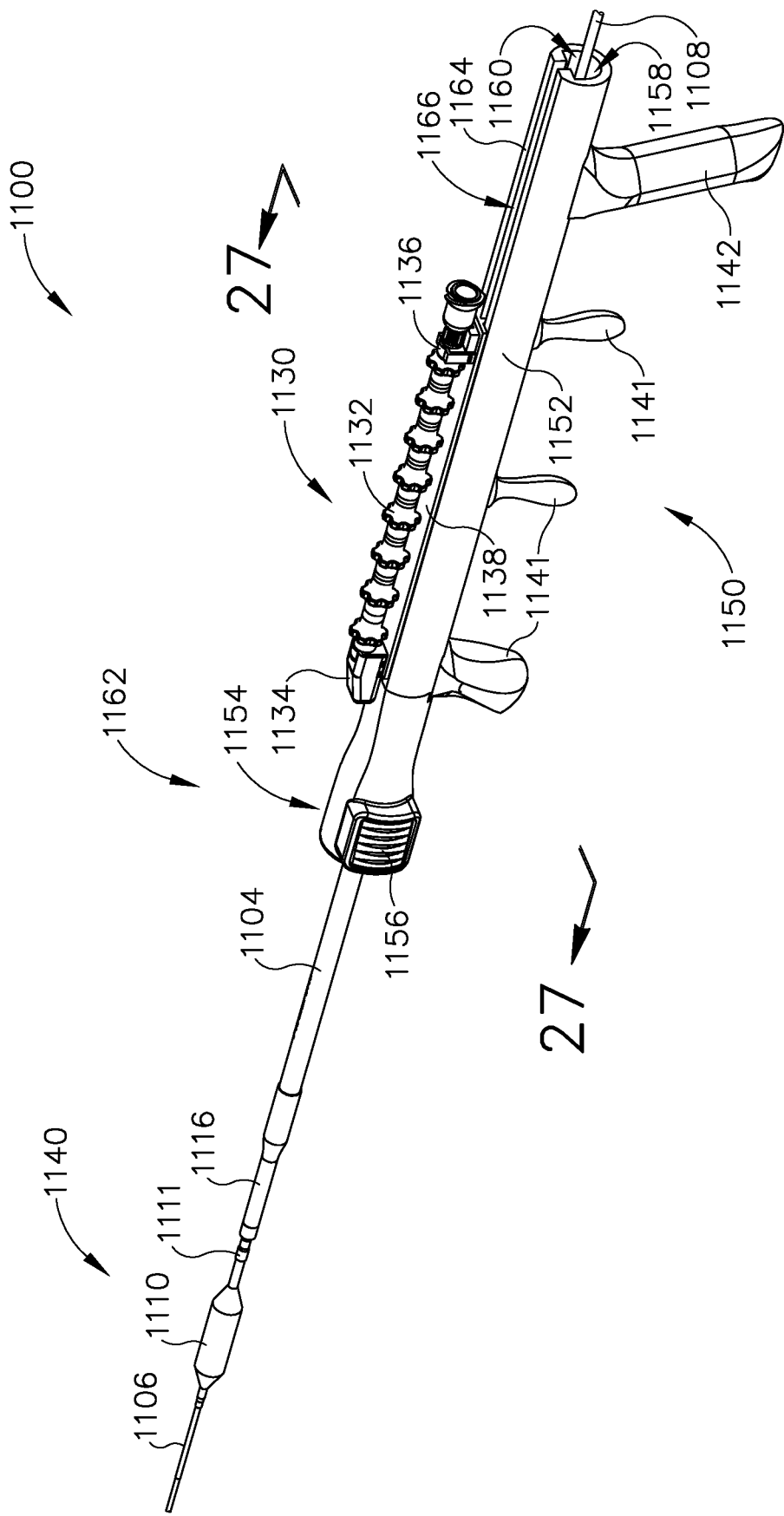
FIG. 26 depicts another perspective view of the dilation catheter system of FIG. 24.
Figure 27:
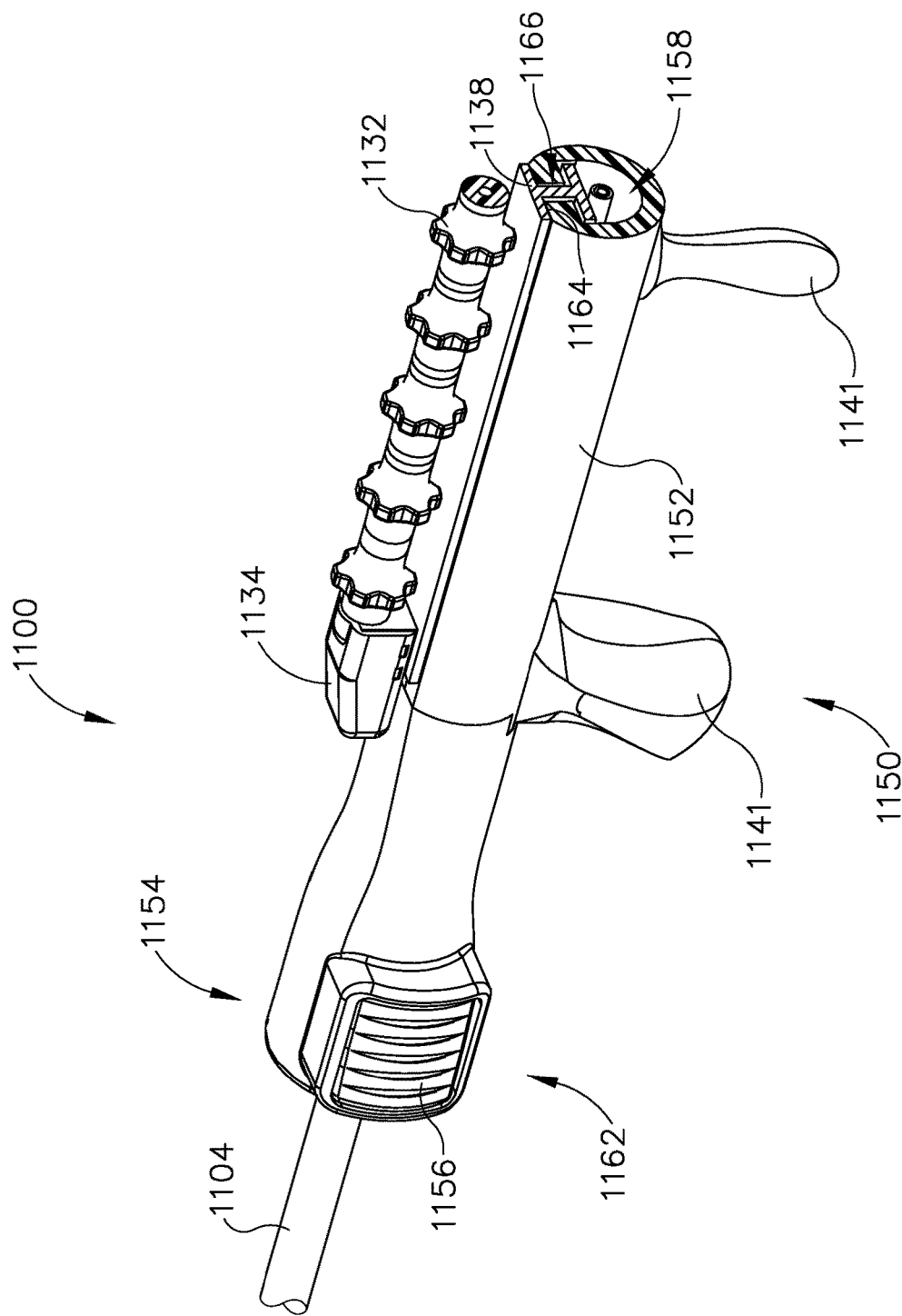
FIG. 27 depicts a cross sectional perspective view of the dilation catheter system of FIG. 24, taken along line 27-27 of FIG. 26.

FIG. 23 depicts an exemplary dilation catheter system (1000) that includes a catheter assembly (1010) and a control console (1020). Catheter assembly (1010) may include a guide catheter, a dilation catheter, and a guidewire (1014) as described herein. In other words, catheter assembly (1010) may include any of the guide catheters described herein (and/or as described in any references cited herein), any of the dilation catheters described herein (and/or as described in any references cited herein), and any of the guidewires described herein (and/or as described in any references cited herein). An inflation conduit (1012) extends proximally from catheter assembly (1010) and is operable to convey inflation fluid to the dilation catheter of catheter assembly (1010). Guidewire (1014) also extends proximally from catheter assembly (1010). In the present example, guidewire (1014) includes one or more optical fibers that are operable to convey light to the distal end of guidewire (1014), thereby enabling the distal end of guidewire (1014) to emit light to provide transillumination as described above and as described in at least one reference cited herein.

Control console (1020) of the present example includes an automated inflation module (1022), a light source (1024), and a user interface (1026). Inflation conduit (1012) is coupled with automated inflation module (1022) such that automated inflation module (1022) is operable to drive inflation fluid through inflation conduit (1012). Automated inflation module (1022) may include a reservoir containing inflation fluid, a fluid pump, one or more sensors that are operable to sense the pressure of the inflation fluid, and a control logic that is operable to activate the fluid pump in response to user input and in response to feedback from the one or more sensors. By way of example only, automated inflation module (1022) may be constructed and operable in accordance with at least some of the teachings of U.S. Pub. No. 2016/0058985, entitled "Automated Inflator for Balloon Dilator," published Mar. 3, 2016, now abandoned, the disclosure of which is incorporated by reference herein. Alternatively, automated inflation module (1022) may be constructed and operable in any other suitable fashion. It should also be understood that inflation conduit (1012) may be coupled with automated inflation module (1022) using various structures, including but not limited to luer lock features, etc.

Guidewire (1014) is configured to couple with light source (1024). Light source (1024) is configured to generate light, which may be communicated to and along the one or more optical fibers contained in guidewire (1014). Various suitable forms that light source (1024) may take will be apparent to those of ordinary skill in the art in view of the teachings herein. Similarly, various suitable ways in which guidewire (1014) may be coupled with light source (1024) will be apparent to those of ordinary skill in the art in view of the teachings herein.

User interface (1026) is operable to receive user input and thereby activate automated inflation module (1022) and/or light source (1024) in response to user input. In addition or in the alternative, user interface (1026) may provide the user with feedback regarding operational parameters of system (1000). By way of example only, user interface (1026) may indicate the operational state of system (1000) (e.g., "ready" or "dilation in process,"), the pressure level of the inflation fluid, instructions on what to do next in the medical procedure, one or more fault conditions, etc. User interface (1026) may take a variety of forms, including but not limited to switches, buttons, a touchscreen, etc. In some versions, user interface (1026) comprises a combination of a display screen that presents information to the user and a footswitch that receives operational input from the user. Various suitable forms that user interface (1026) may take will be apparent to those of ordinary skill in the art in view of the teachings herein.

IX. Exemplary Dilation Catheter Systems

Figure 28:
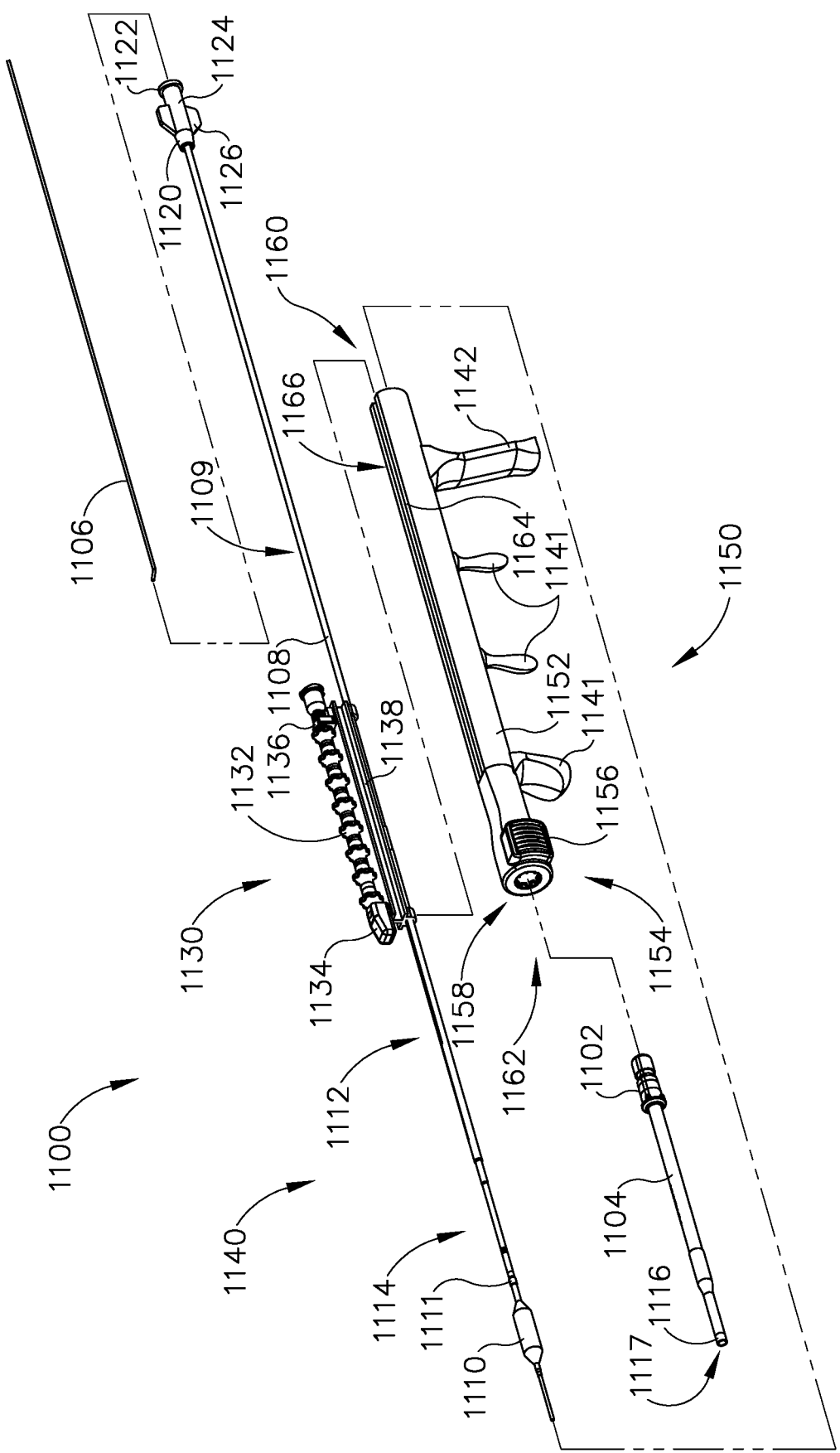
FIG. 28 depicts an exploded perspective view of the dilation catheter system of FIG. 24.

FIGS. 24-29C show an exemplary instrument (1100) that may be used to treat a paranasal sinus drainage passageway (e.g., a frontal recess, a frontal sinus ostium, a maxillary sinus ostium, a sphenoid sinus ostium, etc.) or a Eustachian tube passageway. Instrument (1100) may incorporate any suitable combination of features described above. As best seen in FIG. 28, dilation catheter system (1100) includes a handle assembly (1150), a guide catheter (1104), a dilation catheter assembly (1140), and a guidewire (1106). As will be described in greater detail below, dilation catheter assembly (1140) and guidewire (1106) may actuate relative to handle assembly (1150) and guide catheter (1104) in order to position a distal end of guidewire (1106) and dilation catheter assembly (1140) in a desired position to treat a patient.

Handle assembly (1150) includes a body (1152) extending from an open proximal end (1160) to an open distal end (1162), a distal coupling assembly (1154), a plurality of finger pegs (1141), and a fixed pistol grip (1142). Body (1152) defines a longitudinal channel (1158) extending from open proximal end (1160) to open distal end (1162). Additionally, body (1152) has a slide deck (1164) defining a slide channel (1166) extending from open proximal end (1160) toward open distal end (1162). Slide Channel (1166) extends into adjacent portions of longitudinal channel (1158). Longitudinal channel (1158) is dimensioned to slidably house selected portions of dilation catheter assembly (1140) while slide deck (1164) and slide channel (1166) are dimensioned to slidably couple with an actuation assembly (1130) of dilation catheter assembly (1140).

Distal coupling assembly (1154) includes a button (1156) that may be pressed such that handle assembly (1150) may selectively couple with a proximal coupling portion (1102) of guide catheter (1104). Distal coupling assembly (1154) may include any suitable coupling features used to selectively attach with guide catheter (104, 704) in instruments (600, 700) described above. Therefore, it should be understood that distal coupling assembly (1154) may selectively couple with guide catheter (1104) such that an operator may selectively rotate guide catheter (1104) to any desired rotational position around its own longitudinal axis relative to handle assembly (1150) and lock the selected rotational position.

Finger pegs (1141) and pistol grip (1142) allow an operator to grasp instrument (1100) in numerous different ways. For instance, an operator may simply grasp pistol grip (1142) and thereby support instrument (1100) with a single hand. Alternatively, an operator may wrap the fingers of a single hand around body (1152), with at least one of finger pegs (1141) being positioned between fingers of the grasping hand, to thereby support instrument (1100) with a single hand. In some such grasping scenarios, the operator's hand might not even contact pistol grip (1142). Alternatively, some operators may prefer to contact pistol grip (1142) and at least one finger peg (1141) simultaneously. Various other suitable ways in which instrument (1100) may be grasped will be apparent to those of ordinary skill in the art in view of the teachings herein.

Guide catheter (1104) includes proximal coupling portion (1102) and a removable distal tip (1116). Guide catheter (1104) may be substantially similar to guide catheter (104, 704) described above. Guide catheter (1104) defines an open distal end (1117) that extends all the way to proximal coupling portion (1102). Open distal end (1117) is dimensioned to slidably receive selective portions of dilation catheter assembly (1140).

In the current example, removable distal tip (1116) is rigid and straight. However, it should be understood that removable distal tip (1116) may have any suitable rigid bend that would be apparent to one having ordinary skill in the art in view of the teachings herein. For example, removable distal tip (1116) may have a bend similar to guide tip (116) described above. In some versions, an operator may be presented with a kit having various distal tips (1116) that are each configured to facilitate access to a drainage passageway associated with different sinuses. For instance, one distal tip (1116) may be configured to facilitate access to a frontal recess; with another distal tip (1116) being configured to facilitate access to a maxillary sinus ostium; and with another distal tip (1116) being configured to facilitate access to a sphenoid sinus ostium. The operator may thus select and secure a particular distal tip (1116) based on the targeted anatomical structure. As yet another merely illustrative example, distal tip (1116) may be malleable rather than being rigid, such that the operator may selectively bend distal tip (1116) to a bend angle that facilitates access to a targeted anatomical structure.

The distal end of dilation catheter assembly (1140) includes an inflatable dilator (1110) that may be substantially similar to dilator (22) described above. The proximal end of dilation catheter assembly (1140) includes a proximal connector (1120) having a locking mechanism (1122), an injection port (1124), and an inflation port (1126). Shaft (1108) of dilation catheter assembly includes a first lumen (not shown) that provides fluid communication between inflation port (1126) and the interior of dilator (1110). An operator may inflate/deflate dilator (1110) similar to inflation of dilator (22) described above. Shaft (1108) also defines a second lumen (not shown) that extends from an open distal end of shaft (1108) to injection port (1124). This second lumen is configured to slidably receive guidewire (1106). The first and second lumens of shaft (1108) are fluidly isolated from each other. Thus, dilator (1110) may be selectively inflated and deflated by communicating fluid along the first lumen via inflation port (1126) while guidewire (1106) is positioned within the second lumen. Injection port (1124) and inflation port (1126) may be substantially similar to injection port (436) and inflation port (430) described above, respectively.

Locking mechanism (1122) may selectively lock guidewire (1106) within second lumen of shaft (1108) such that guidewire (1106) is selectively fixed to dilation catheter assembly (1140). Therefore guidewire (1106) may be inserted through injection port (1124) such a distal end of guidewire (1106) is positioned distally to open distal tip of shaft (1108), then guidewire (1106) may be locked into position utilizing locking mechanism (1122). Locking mechanism (1122) may have any suitable features of locking mechanism of instrument (300) described above. In some variations, locking mechanism (1122) is omitted, such that guidewire (1106) remains slidable relative to dilation catheter assembly (1140).

Dilation catheter assembly (1140) also includes actuation assembly (1130). As will be described in greater detail below, actuation assembly (1130) may selectively rotate, retract, and advance guide catheter assembly (1140) and guidewire (1106) relative to handle assembly (1150) and guide catheter (1104). Actuation assembly (1130) includes a rotating finger grip (1132), a distal rotary coupling (1134), a proximal rotary coupling (1136), and a slide body (1138). Slide body (1138) may slidably couple with body (1152) of handle assembly (1150) via slide deck (1164), slide channel (1166), and longitudinal channel (1158). An operator may insert slide body (1138) through slide channel (116) and longitudinal channel (1158) via open proximal end (1160). Therefore, slide body (1138) may be supported by slide deck (1164), but configured to slide relative handle assembly (1150).

Rotating finger grip (1132) is rotatably coupled to rotary couplings (1134, 1136) such that finger grip (1132) may rotate about its own longitudinal axis relative to slide body (1138). Slide body (1138) is coupled with shaft (1108) such that translation of slide body (1138) leads to translation of dilation catheter assembly (1140). Slide body (1138) is also coupled with shaft (1108) such that shaft (1108) may rotate about its own longitudinal axis relative to slide body (1138). Rotating finger grip (1132) is coupled with shaft (1108) such that rotation of finger grip (1132) about its own longitudinal axis leads to rotation of shaft (1108) about its own longitudinal axis. Rotating finger grip (1132) may be coupled with shaft (1108) through any suitable means as would be apparent to one having ordinary skill in the art in view of the teachings herein. By way of example only, rotating finger grip (1132) may be coupled with shaft (1108) in accordance with at least some of the teachings of U.S. patent application Ser. No. 15/278,588, entitled "Dilation Catheter Assembly with Rapid Change Components," filed Sep. 28, 2016, issued as U.S. Pat. No. 10,625,062 on Apr. 21, 2020, the disclosure of which is incorporated by reference herein.

It should be understood that an operator may actuate or rotate finger grip (1132) in order to actuate or rotate dilation catheter assembly (1140) relative to handle assembly (1150). In the present example, rotating finger grip (1132) is offset from shaft (1108) such their respective longitudinal axes are spaced apart from each other. It should also be understood that an operator may actuate (i.e., longitudinally translate) finger grip (1132) and/or rotate finger grip (1132) using the same hand that grasps body (1152) and/or pistol grip (1142).

The portion (1112) of shaft (1108) that is distal of actuation assembly (1130) may be sufficiently stiff to be guided through the nasal cavity and into a Eustachian tube or into a drainage passageway associated with a paranasal sinus. In some versions, portion (1112) is formed of stainless steel, similar to portion (440) described above. The portion (1109) that is proximal of actuation assembly (1130) and the portion (1114) that is distal to portion (1112) may be more flexible than portion (1112). Therefore, portions (1114, 1109) may be substantially similar to portions (450, 438), respectively. Of course, any other suitable stiffness of portions (1112, 1114, 1109) may be used as would be apparent to one having ordinary skill in the art in view of the teachings herein.

Figure 29A:
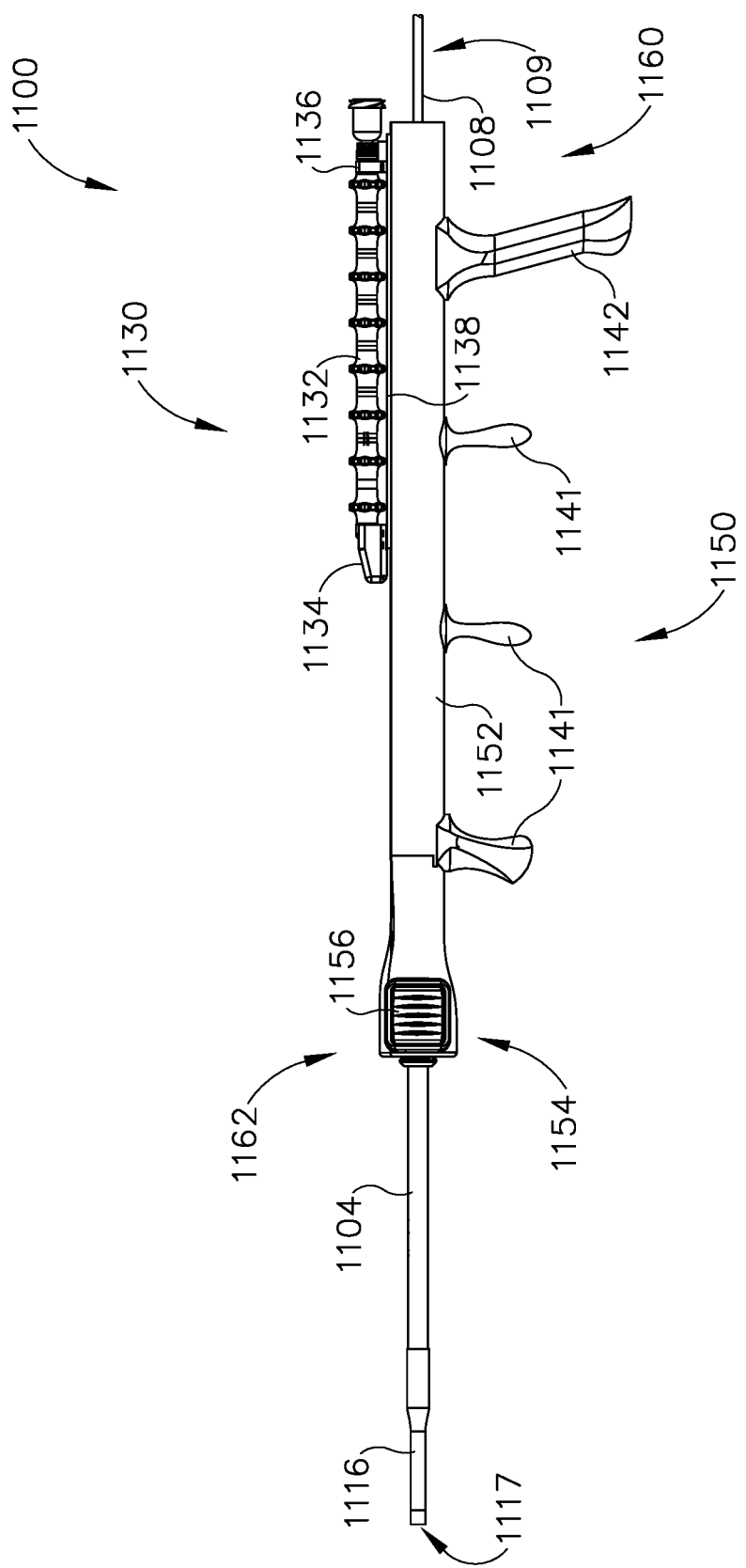
FIG. 29A depicts a side elevational view of the dilation catheter system of FIG. 24, where the actuation assembly, dilation catheter assembly, and guidewire are in a retracted position.
Figure 30:
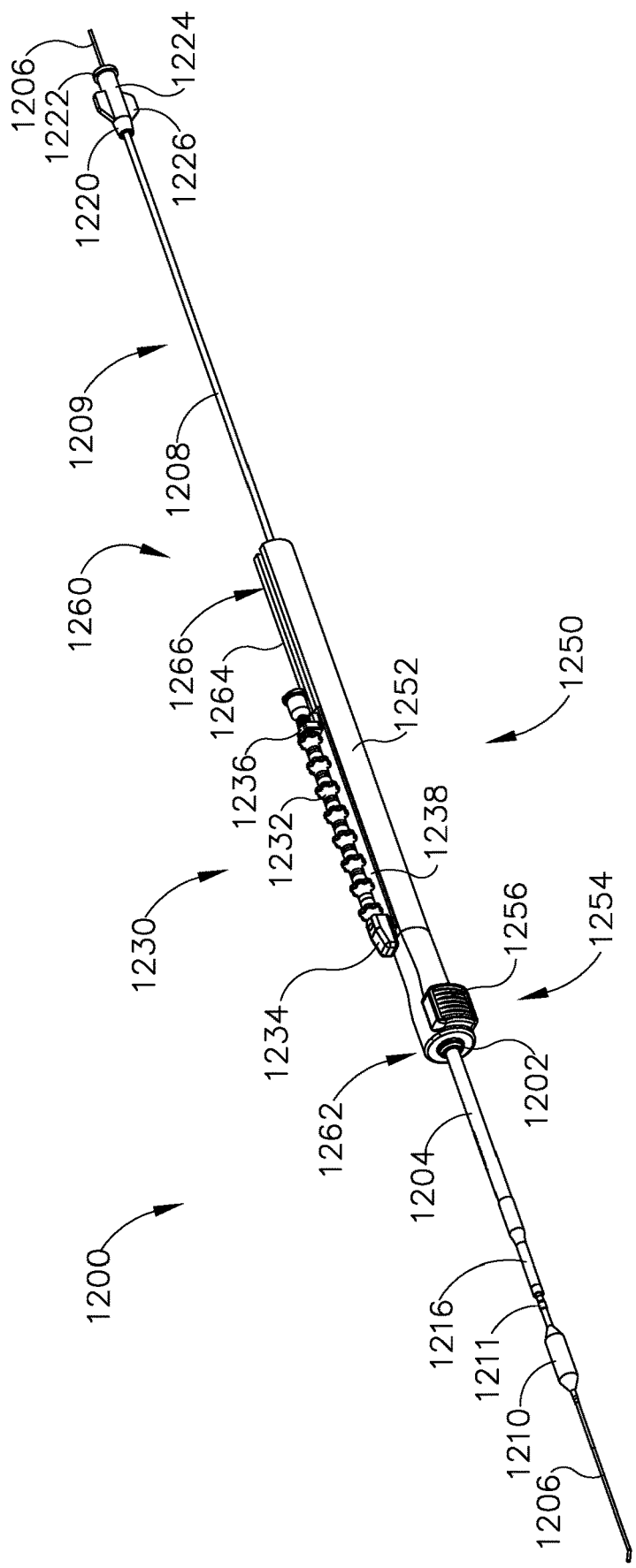
FIG. 30 depicts a perspective view of another exemplary alternative dilation catheter system.
Figure 31:
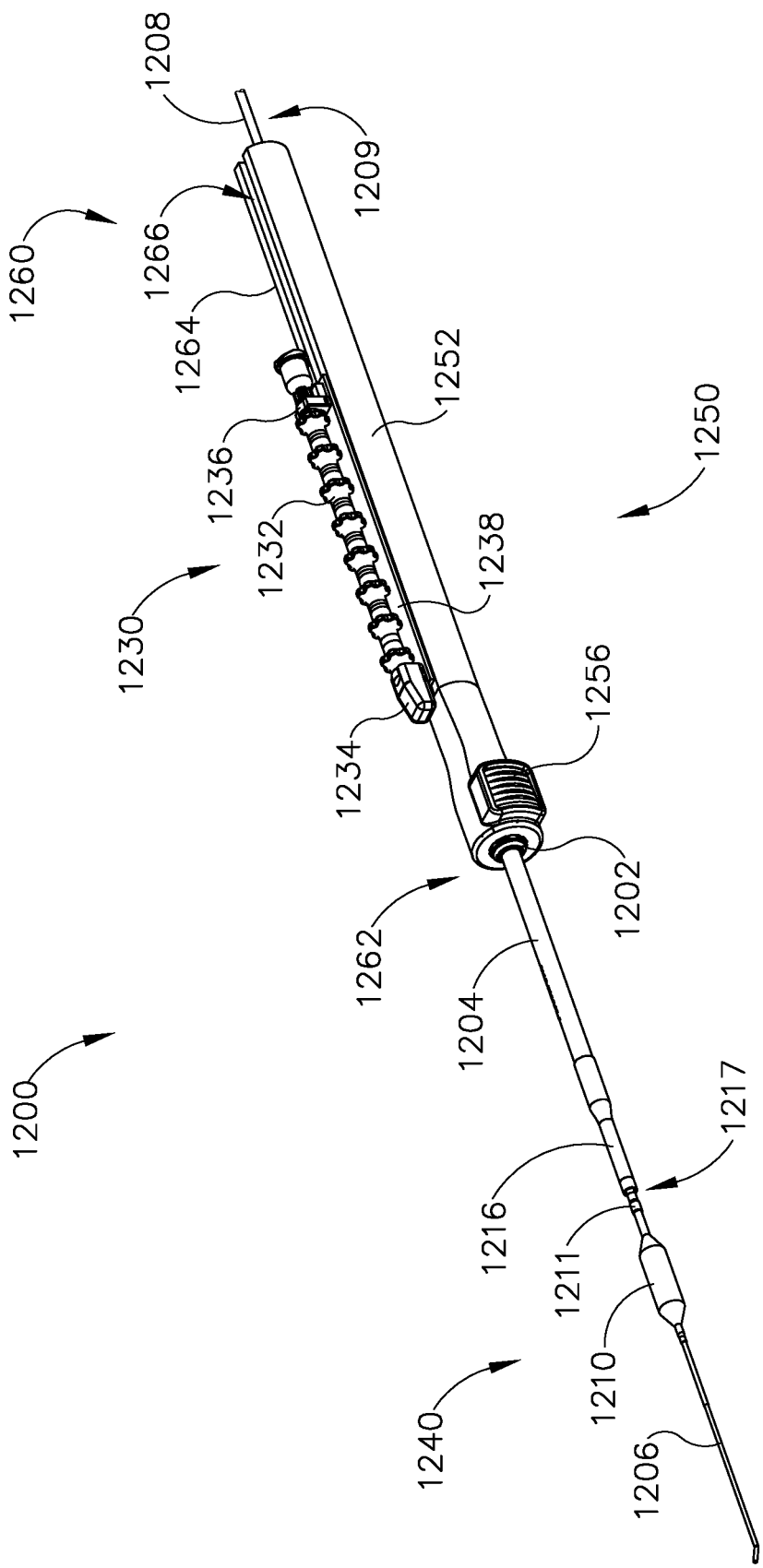
FIG. 31 depicts an enlarged perspective view of the dilation catheter system of FIG. 30.
Figure 32:
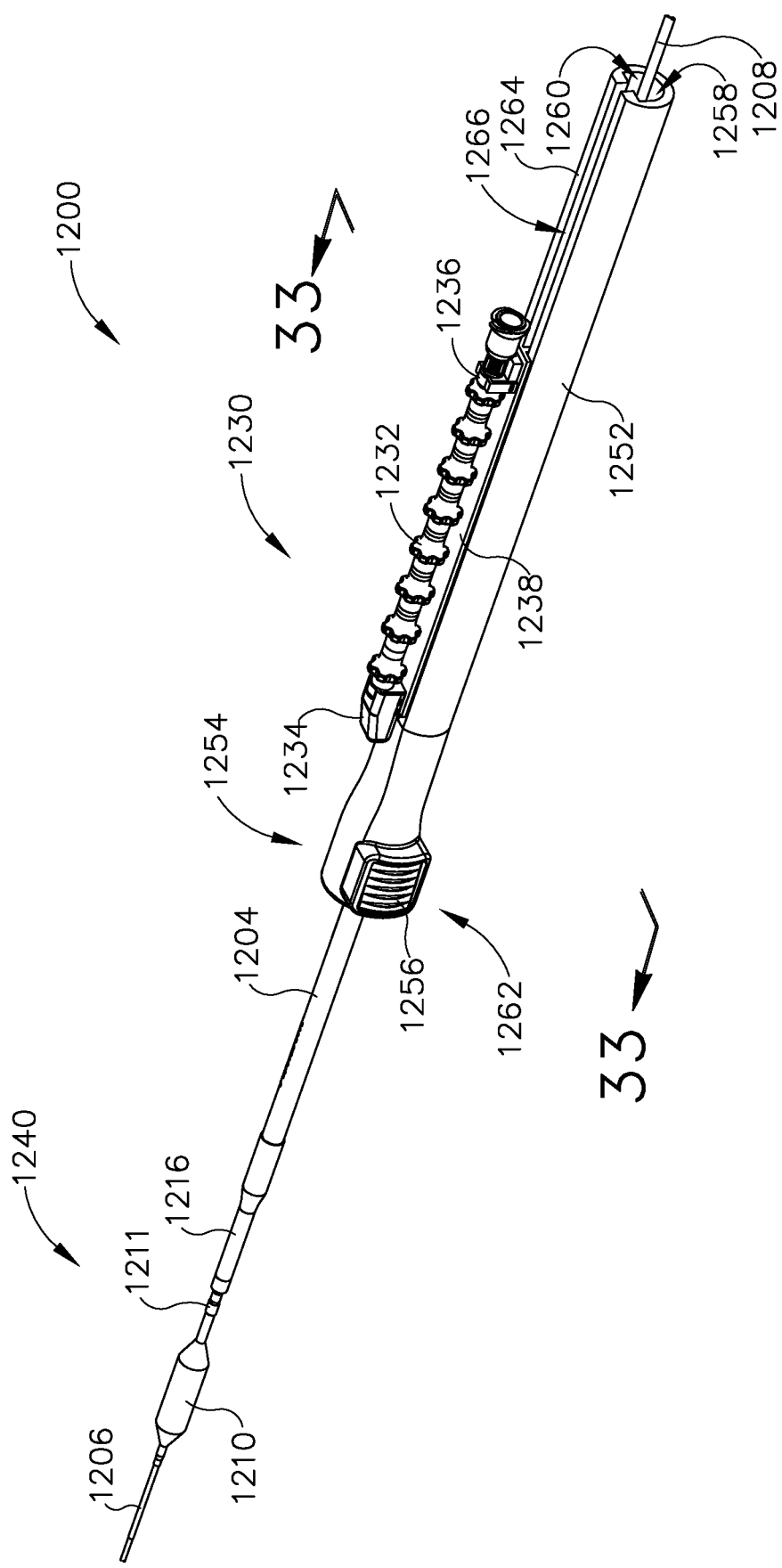
FIG. 32 depicts another perspective view of the dilation catheter system of FIG. 30.
Figure 33:
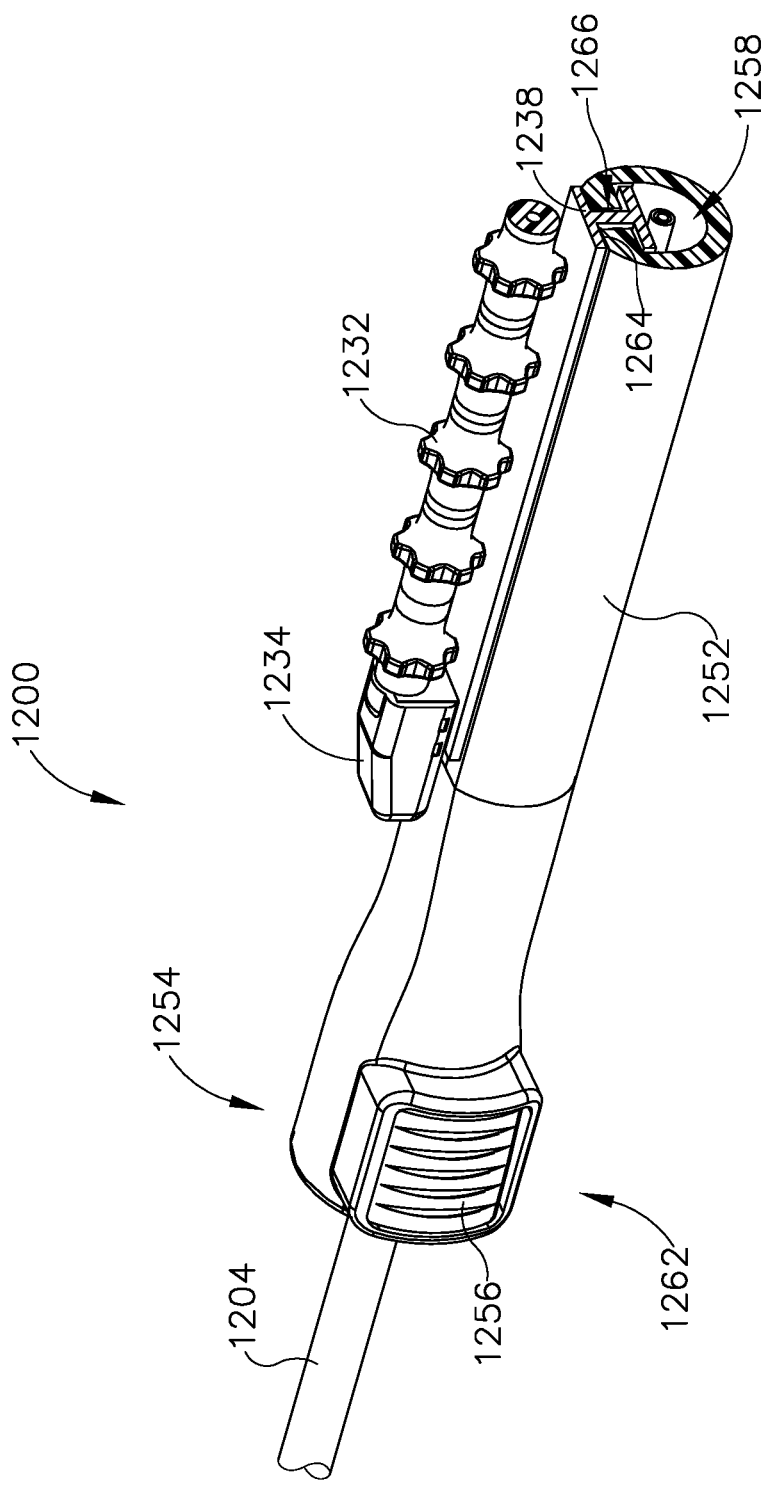
FIG. 33 depicts a cross sectional perspective view of the dilation catheter system of FIG. 30, taken along line 33-33 of FIG. 32.

FIGS. 29A-29C show an exemplary use of instrument (1100). First, an operator may insert the distal end of guidewire (1106) through injection port (1124) and through second lumen of shaft (1108) until the distal end of guidewire (1106) extends through the open distal end of shaft (1108) a desired distance. The operator may then utilize locking mechanism (1122) in order to fix guidewire (1106) to shaft (1108). With guidewire (1106) coupled, the operator may place actuation assembly (1130) is in a retracted position, as shown in FIG. 29A, such that the distal end of guidewire (1106) is within guide catheter (1104). The operator may advance instrument (1100) such that detachable tip (1116) and a distal portion of guide catheter (1104) are within a desired location in a patient.

In the present example, at the stage shown in FIG. 29A, dilation catheter assembly (1140) is in a proximal position during the positioning of detachable tip (1116) and a distal portion of guide catheter (1104) within a desired location in a patient, such that the distal portion of dilator catheter assembly (1140) is retracted within detachable tip (1116) and/or further proximally within guide catheter (1104). In addition, the distal end of guidewire (1106) is contained within guide catheter (1104) at the stage shown in FIG. 29A. In some other variations, the distal end of guidewire (1106) protrudes distally from the distal end of guide catheter (1104) during the positioning of detachable tip (1116) and a distal portion of guide catheter (1104) within a desired location in a patient, while the distal portion of dilator catheter assembly (1140) remains retracted within detachable tip (1116) and/or further proximally within guide catheter (1104).

Next, the operator may advance actuation assembly (1130) via finger grip (1132) such that guidewire (1106) and dilation catheter assembly (1140) distally pass detachable tip (1116) and dilator (1110) is in the desired location within a patient, as shown in FIG. 29B. Before and/or during advancement of instrument (1100), the operator may rotate guidewire (1106) and dilation catheter assembly (1140) via manipulation of finger grip (1132) as described above. This may promote entry of the distal end of guidewire (1106) into the targeted anatomical structure (e.g., sinus ostium, Eustachian tube, etc.). It should be understood that dilator (1110) is deflated at this point. Next, the operator may inflate dilator (1110) in order to dilate the targeted anatomical structure in the patient, as shown in FIG. 29C. When finished, the operator may deflate dilator (1110), as shown in FIG. 29B, then retract dilator (1110) and guidewire (1106) to the position shown in FIG. 29A, and finally remove guide catheter (1104) from the patient.

Figure 34:
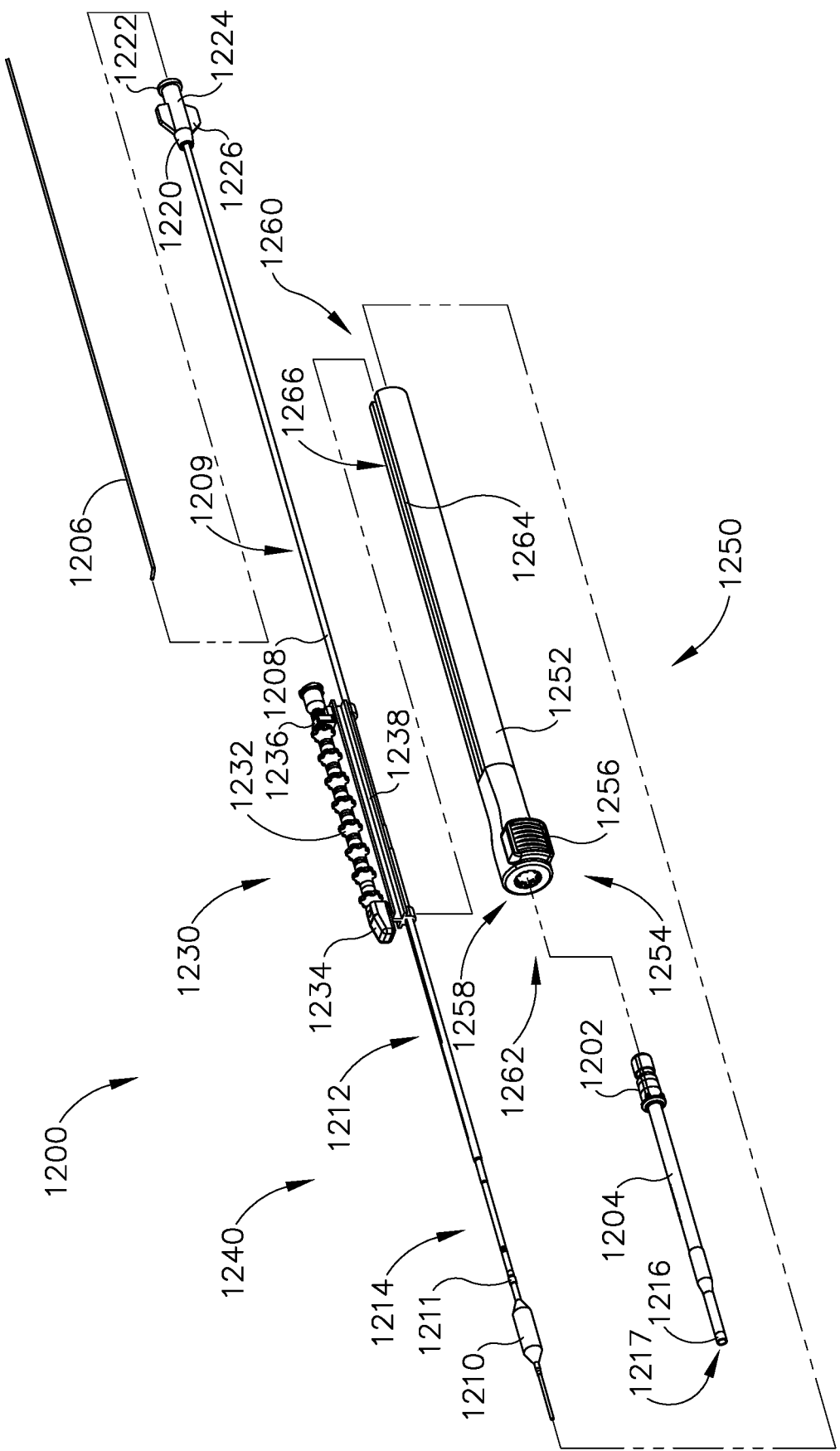
FIG. 34 depicts an exploded perspective view of the dilation catheter system of FIG. 30.

FIGS. 30-35C show another exemplary instrument (1200) that may be used to treat a paranasal sinus drainage passageway (e.g., a frontal recess, a frontal sinus ostium, a maxillary sinus ostium, a sphenoid sinus ostium, etc.) or a Eustachian tube passageway. Instrument (1200) may incorporate any suitable combination of features described above. As best seen in FIG. 34, dilation catheter system (1200) includes a handle assembly (1250), a guide catheter (1204), a dilation catheter assembly (1240), and a guidewire (1206). As will be described in greater detail below, dilation catheter assembly (1240) and guidewire (1206) may actuate relative to handle assembly (1250) and guide catheter (1204) in order to position a distal end of guidewire (1206) and dilation catheter assembly (1240) in a desired position to treat a patient.

Handle assembly (1250) includes a body (1252) extending from an open proximal end (1260) to an open distal end (1262), a distal coupling assembly (1254). Body (1252)

defines a longitudinal channel (1258) extending from open proximal end (1260) to open distal end (1262). Additionally, body (1252) has a slide deck (1264) defining a slide channel (1266) extending from open proximal end (1260) toward open distal end (1262). Slide Channel (1266) extends into adjacent portions of longitudinal channel (1258). Longitudinal channel (1258) is dimensioned to slidably house selected portions of dilation catheter assembly (1240) while slide deck (1264) and slide channel (1266) are dimensioned to slidably couple with an actuation assembly (1230) of dilation catheter assembly (1240).

Distal coupling assembly (1254) includes a button (1256) that may be pressed such that handle assembly (1250) may selectively couple with a proximal coupling portion (1202) of guide catheter (1204). Distal coupling assembly (1254) may include any suitable coupling features used to selectively attach with guide catheter (104) in instruments (600, 700) described above. Therefore, it should be understood that distal coupling assembly (1254) may couple with guide catheter (1204) such that an operator may selective rotate guide catheter (1204) to any desired rotational position around its own longitudinal axis relative to handle assembly (1250).

Body (1252) of handle assembly (1250) may be grasped like a pencil such that an operator may grasp instrument (1200) with a single hand. Other suitable ways in which body (1252) may be grasped will be apparent to those of ordinary skill in the art in view of the teachings herein. Body (1252) may include a textured gripping surface and/or other features in order to provide a sturdier grip.

Guide catheter (1204) includes proximal coupling portion (1202) and a removable distal tip (1216). Guide catheter (1204) may be substantially similar to guide catheter (104, 704, 1100) described above. Guide catheter (1204) defines an open distal end (1217) that extends all the way to proximal coupling portion (1202). Open distal end (1217) is dimensioned to slidably receive selective portions of dilation catheter assembly (1240).

In the current example, removable distal tip (1216) is rigid and straight. However, it should be understood that removable distal tip (1216) may have any suitable rigid bend that would be apparent to one having ordinary skill in the art in view of the teachings herein. For example, removable distal tip (1216) may have a bend similar to guide tip (116) described above. In some versions, an operator may be presented with a kit having various distal tips (1216) that are each configured to facilitate access to a drainage passageway associated with different sinuses. For instance, one distal tip (1216) may be configured to facilitate access to a frontal recess; with another distal tip (1216) being configured to facilitate access to a maxillary sinus ostium; and with another distal tip (1216) being configured to facilitate access to a sphenoid sinus ostium. The operator may thus select and secure a particular distal tip (1216) based on the targeted anatomical structure. As yet another merely illustrative example, distal tip (1216) may be malleable rather than being rigid, such that the operator may selectively bend distal tip (1216) to a bend angle that facilitates access to a targeted anatomical structure.

The distal end of dilation catheter assembly (1240) includes an inflatable dilator (1210) that may be substantially similar to dilator (22) described above. The proximal end of dilation catheter assembly (1240) includes a proximal connector (1220) having a locking mechanism (1222), an injection port (1224), and an inflation port (1226). Shaft (1208) of dilation catheter assembly includes a first lumen (not shown) that provides fluid communication between inflation port (1226) and the interior of dilator (1210). An operator may inflate/deflate dilator (1210) similar to inflation of dilator (22) described above. Shaft (1208) also defines a second lumen (not shown) that extends from an open distal end of shaft (1208) to injection port (1224). This second lumen is configured to slidably receive guidewire (1206). The first and second lumens of shaft (1208) are fluidly isolated from each other. Thus, dilator (1210) may be selectively inflated and deflated by communicating fluid along the first lumen via inflation port (1226) while guidewire (1206) is positioned within the second lumen. Injection port (1224) and inflation port (1226) may be substantially similar to injection port (436) and inflation port (430) described above, respectively.

Locking mechanism (1222) may selectively lock guidewire (1206) within second lumen of shaft (1208) such that guidewire (1206) is selectively fixed to dilation catheter assembly (1240). Therefore guidewire (1206) may be inserted through injection port (1224) such a distal end of guidewire (1206) is positioned distally to open distal tip of shaft (1208), then guidewire (1206) may be locked into position utilizing locking mechanism (1222). Locking mechanism (1222) may have any suitable features of locking mechanism of instrument (300) described above. In some variations, locking mechanism (1222) is omitted, such that guidewire (1206) remains slidable relative to dilation catheter assembly (1240).

Dilation catheter assembly (1240) also includes actuation assembly (1230). As will be described in greater detail below, actuation assembly (1230) may selectively rotate, retract, and advance guide catheter assembly (1240) and guidewire (1206) relative to handle assembly (1250) and guide catheter (1204). Actuation assembly (1230) includes a rotating finger grip (1232), a distal rotary coupling (1234), a proximal rotary coupling (1236), and a slide body (1238). Slide body (1238) may slidably couple with body (1252) of handle assembly (1250) via slide deck (1264), slide channel (1266) and longitudinal channel (1258). An operator may insert slide body (1238) through slide channel (126) and longitudinal channel (1258) via open proximal end (1260). Therefore, slide body (1238) may be supported by slide deck (1264), but configured to slide relative handle assembly (1250).

Rotating finger grip (1232) is rotatably coupled to rotary couplings (1234, 1136) such that finger grip (1232) may rotate about its own longitudinal axis relative to slide body (1238). Slide body (1238) is coupled with shaft (1208) such that translation of slide body (1238) leads to translation of dilation catheter assembly (1240). Slide body (1238) is also coupled with shaft (1208) such that shaft (1208) may rotate about its own longitudinal axis relative to slide body (1238). Rotating finger grip (1232) is coupled with shaft (1208) such that rotation of finger grip (1232) about its own longitudinal axis leads to rotation of shaft (1208) about its own longitudinal axis. Rotating finger grip (1232) may be coupled with shaft (1208) through any suitable means as would be apparent to one having ordinary skill in the art in view of the teachings herein. By way of example only, rotating finger grip (1232) may be coupled with shaft (1208) in accordance with at least some of the teachings of U.S. patent application Ser. No. 15/278,588, entitled "Dilation Catheter Assembly with Rapid Change Components," filed Sep. 28, 2016, issued as U.S. Pat. No. 10,625,062 on Apr. 21, 2020, the disclosure of which is incorporated by reference herein.

It should be understood that an operator may actuate or rotate finger grip (1232) in order to actuate or rotate dilation catheter assembly (1240) relative to handle assembly (1250). In the present example, rotating finger grip (1232) is offset from shaft (1208) such their respective longitudinal axis spaced apart from each other. It should also be understood that an operator may actuate (i.e., longitudinally translate) finger grip (1132) and/or rotate finger grip (1132) using the same hand that grasps body (1152) and/or pistol grip (1142).

The portion (1212) of shaft (1208) that is distal of actuation assembly (1230) may be sufficiently stiff to be guided through the nasal cavity and into a Eustachian tube or into a drainage passageway associated with a paranasal sinus. In some versions, portion (1212) is formed of stainless steel, similar to portion (440) described above. The portion (1209) that is proximal of actuation assembly (1230) and the portion (1214) that is distal to portion (1212) may be more flexible than portion (1212). Therefore, portions (1214, 1109) may be substantially similar to portions (450, 438), respectively. Of course, any other suitable stiffness of portions (1212, 1114, 1109) may be used as would be apparent to one having ordinary skill in the art in view of the teachings herein.

Figure 35A:
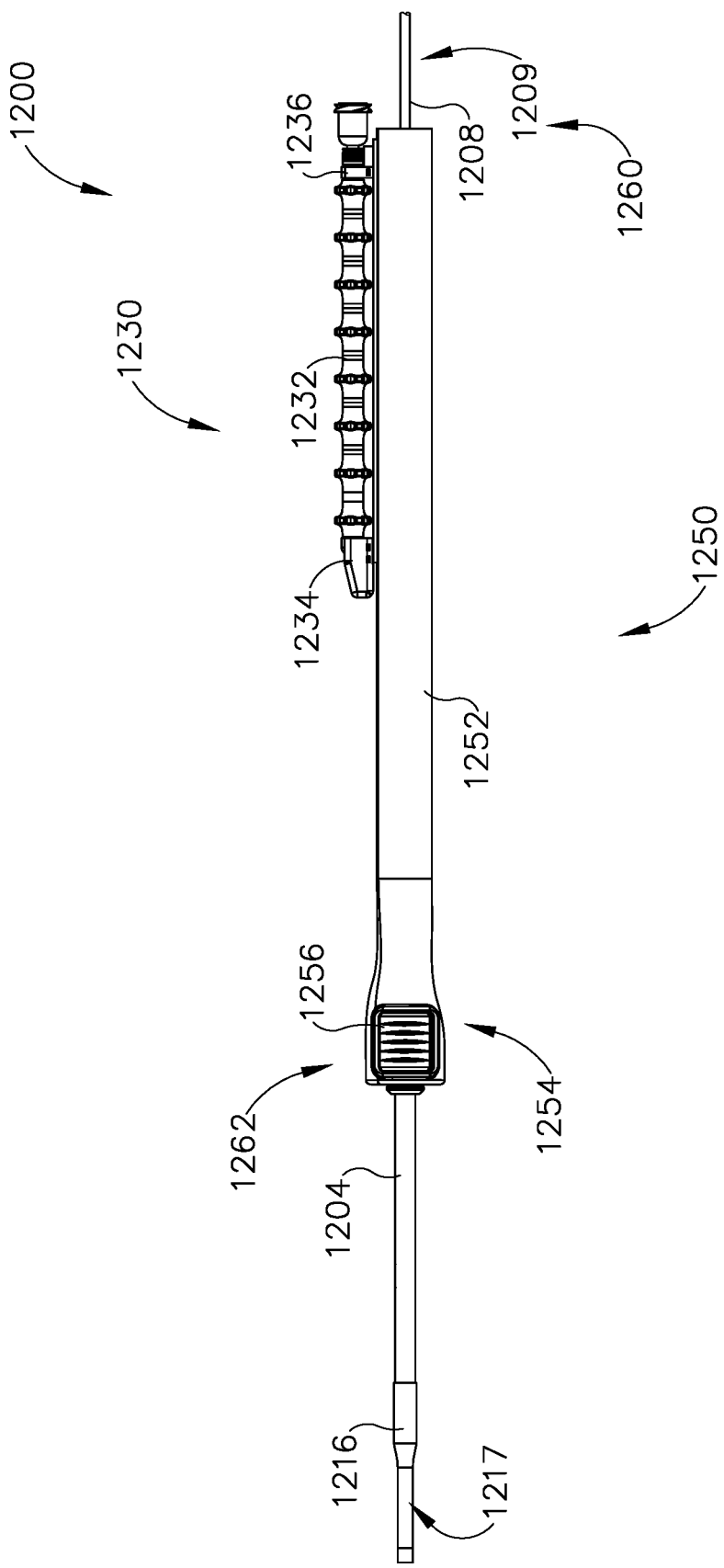
FIG. 35A depicts a side elevational view of the dilation catheter system of FIG. 30, where the actuation assembly, dilation catheter assembly, and guidewire are in a retracted position.
Figure 36:
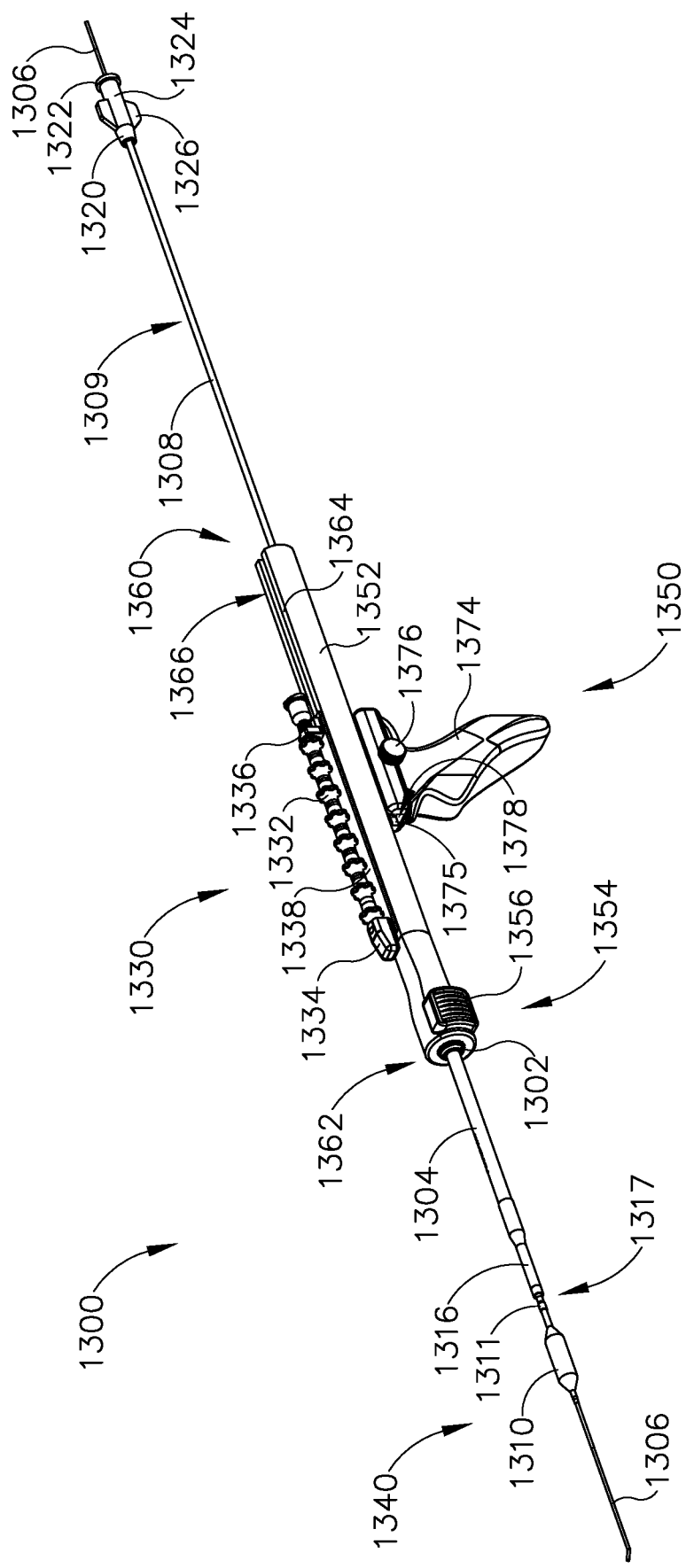
FIG. 36 depicts a perspective view of another exemplary alternative dilation catheter system.
Figure 37:
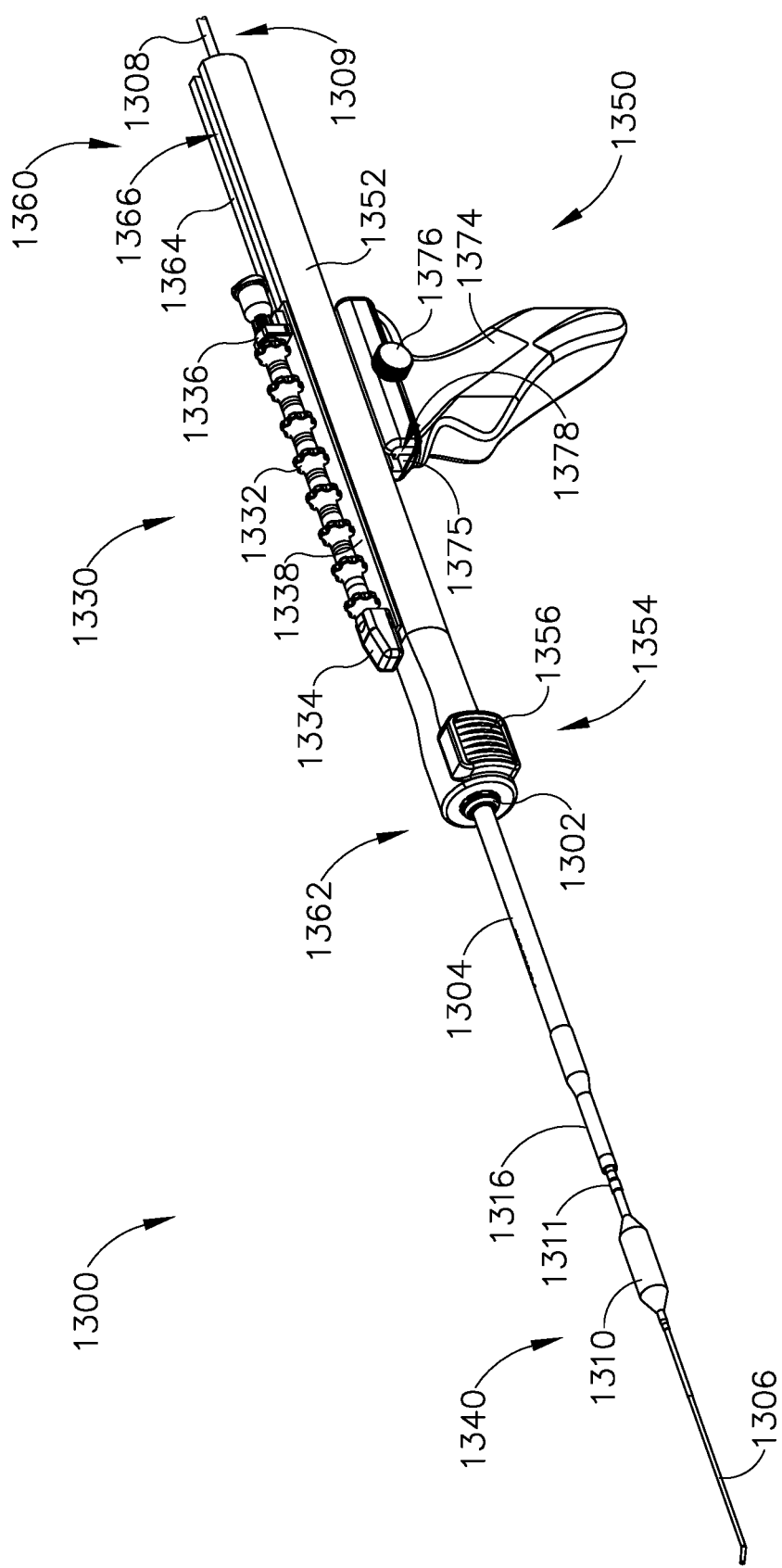
FIG. 37 depicts an enlarged perspective view of the dilation catheter system of FIG. 36.
Figure 38:
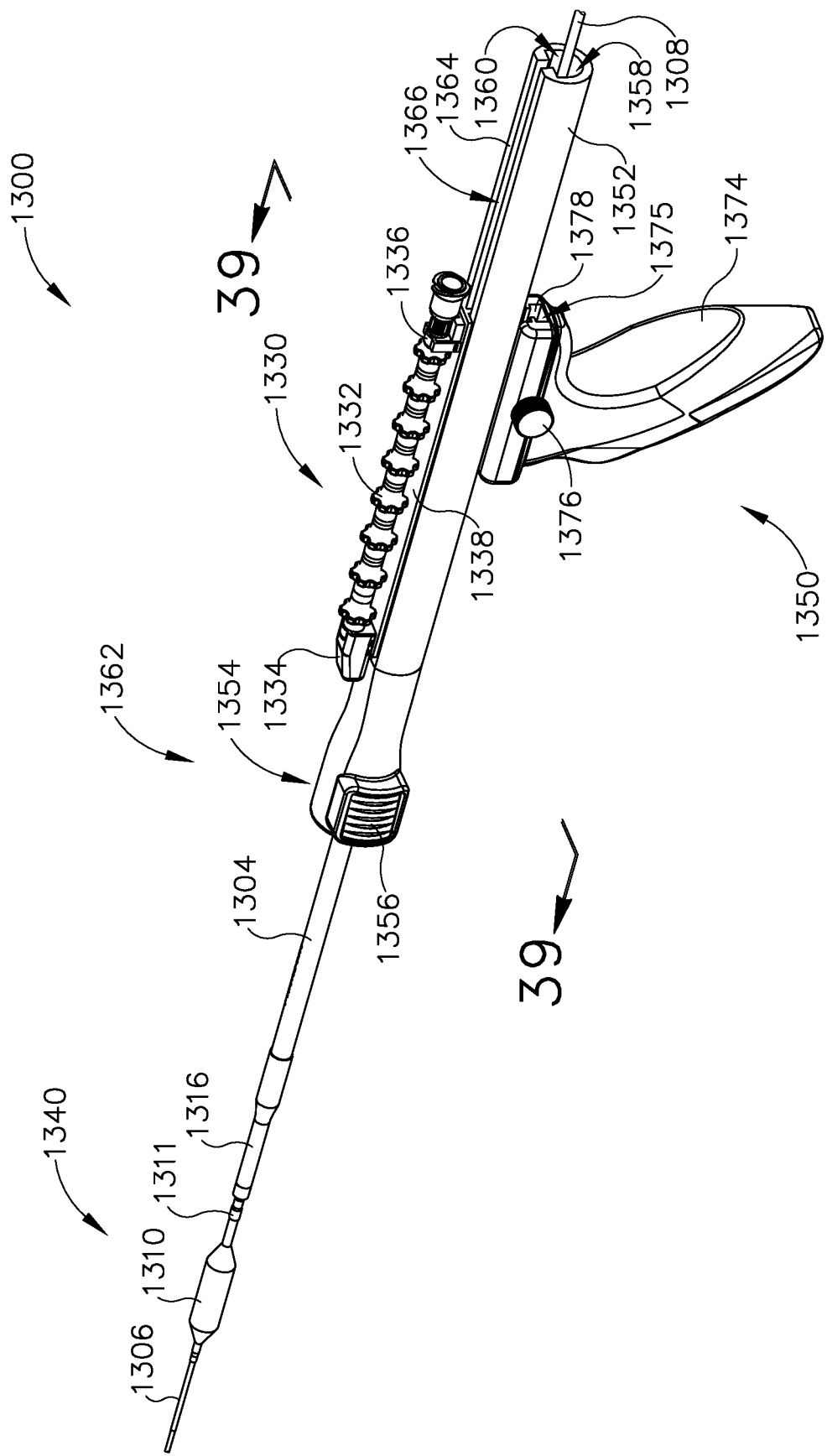
FIG. 38 depicts another perspective view of the dilation catheter system of FIG. 36.
Figure 39:
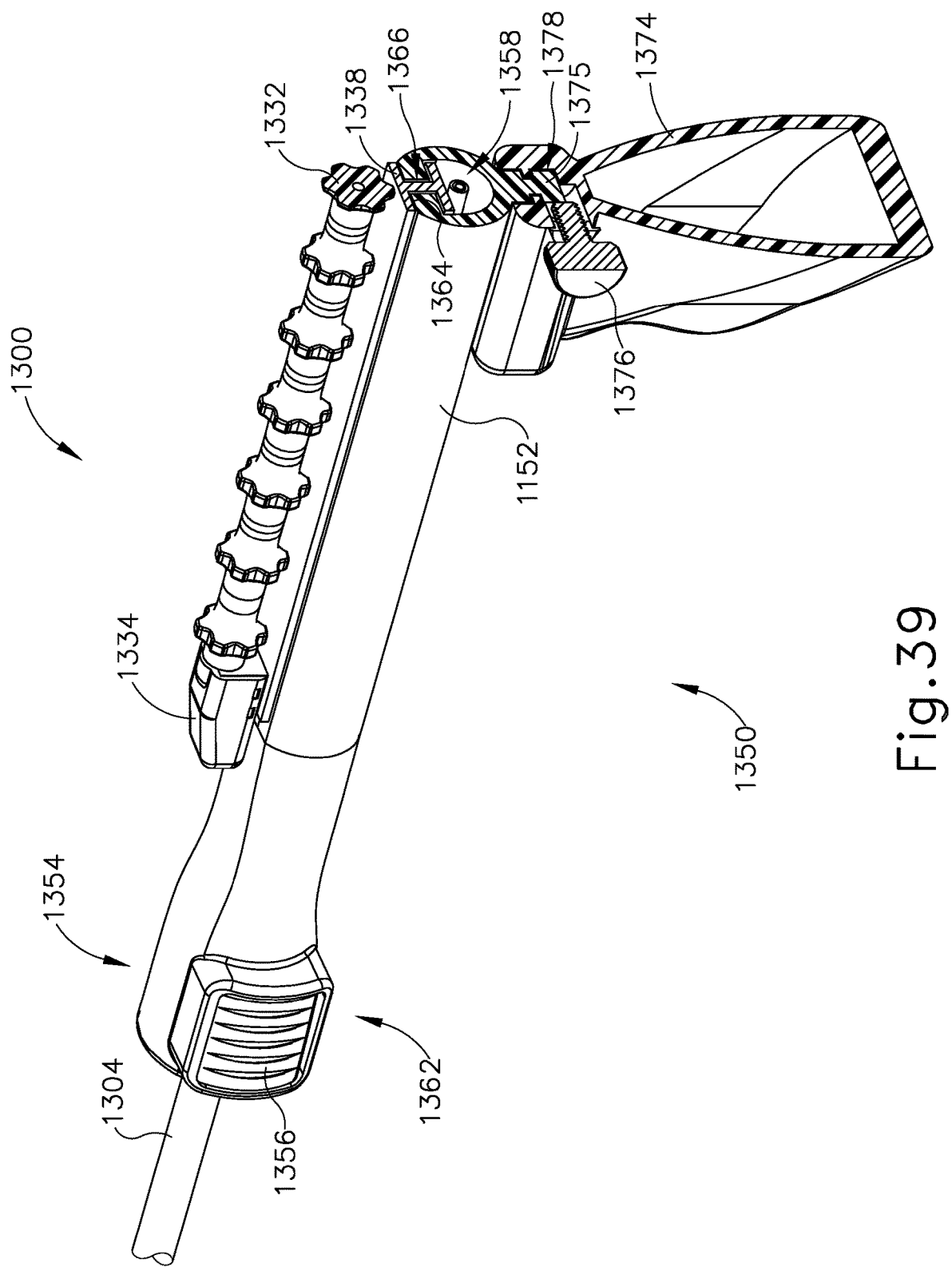
FIG. 39 depicts a cross sectional perspective view of the dilation catheter system of FIG. 36, taken along line 39-39 of FIG. 38.
Figure 40:
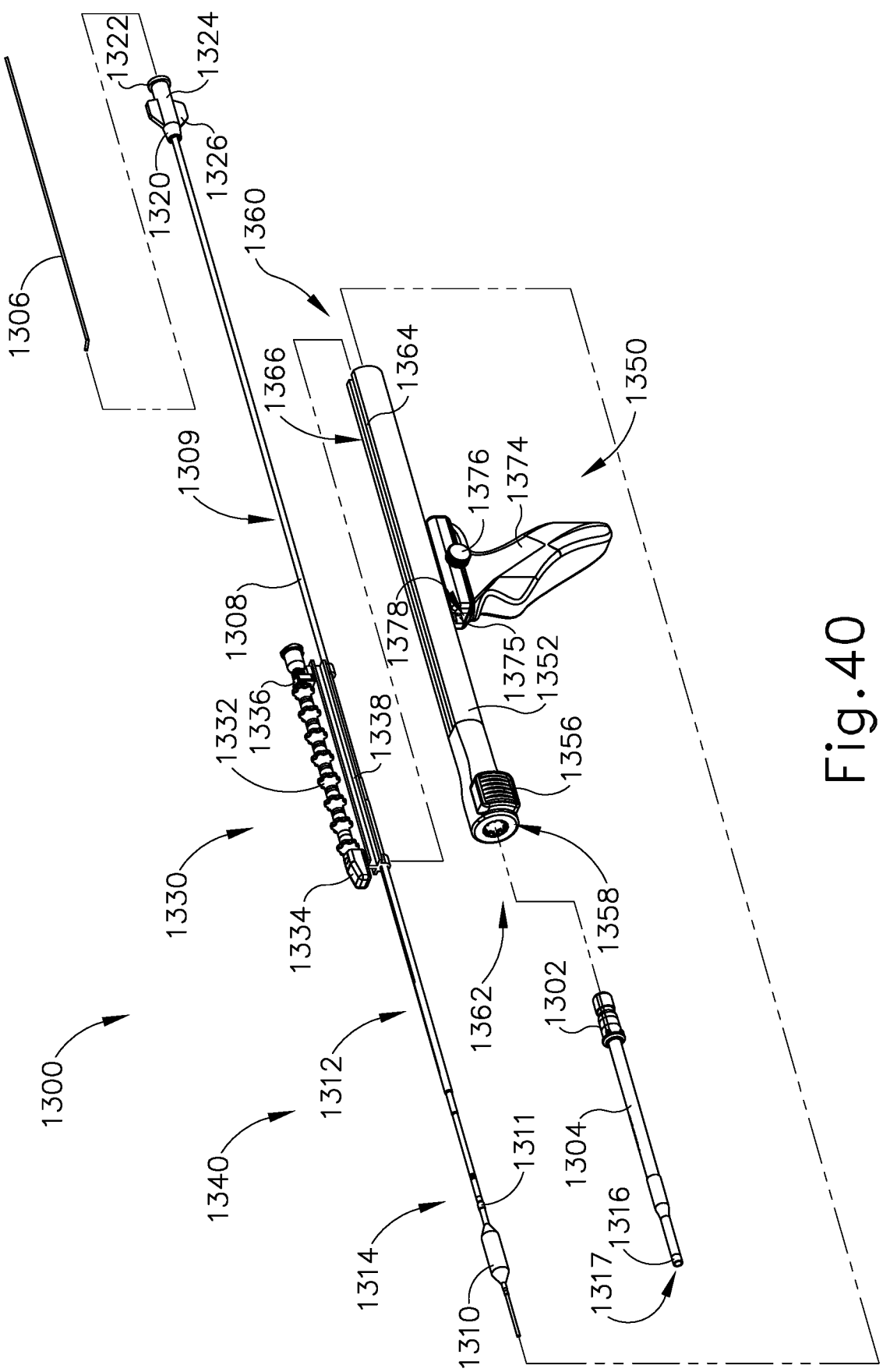
FIG. 40 depicts an exploded perspective view of the dilation catheter system of FIG. 36.

FIGS. 35A-35C show an exemplary use of instrument (1200). First, an operator may insert the distal end of guidewire (1206) through injection port (1224) and through second lumen of shaft (1208) until the distal end of guidewire (1206) extends through the open distal end of shaft (1208) a desired distance. An operator may then utilize locking mechanism (1222) in order to fix guidewire (1206) to shaft (1208). With guidewire (1206) coupled, the operator may place actuation assembly (1230) is in a retracted position, as shown in FIG. 35A, such that the distal end of guidewire (1206) is within guide catheter (1204). The operator may advance instrument (1200) such that detachable tip (1216) and a distal portion of guide catheter (1204) are within a desired location in a patient.

In the present example, at the stage shown in FIG. 35A, dilation catheter assembly (1240) is in a proximal position during the positioning of detachable tip (1216) and a distal portion of guide catheter (1204) within a desired location in a patient, such that the distal portion of dilator catheter assembly (1240) is retracted within detachable tip (1216) and/or further proximally within guide catheter (1204). In addition, the distal end of guidewire (1206) is contained within guide catheter (1204) at the stage shown in FIG. 35A. In some other variations, the distal end of guidewire (1206) protrudes distally from the distal end of guide catheter (1204) during the positioning of detachable tip (1216) and a distal portion of guide catheter (1204) within a desired location in a patient, while the distal portion of dilator catheter assembly (1240) remains retracted within detachable tip (1216) and/or further proximally within guide catheter (1204).

Next, the operator may advance actuation assembly (1230) via finger grip (1232) such that guidewire (1206) and dilation catheter assembly (1240) distally pass detachable tip (1216) and dilator (1210) is in the desired location within a patient, as shown in FIG. 35B. Before and/or during advancement of instrument (1200), the operator may rotate guidewire (1206) and dilation catheter assembly (1240) via manipulation of finger grip (1232) as described above. This may promote entry of the distal end of guidewire (1206) into the targeted anatomical structure (e.g., sinus ostium, Eustachian tube, etc.). It should be understood that dilator (1210) is deflated at this point. Next, the operator may inflate dilator (1210) in order to dilate the targeted anatomical structure in the patient, as shown in FIG. 35C. When finished, the operator may deflate dilator (1210), as shown in FIG. 35B, then retract dilator (1210) and guidewire (1206) to the position shown in FIG. 35A, and finally remove guide catheter (1204) from the patient.

FIGS. 36-41C show another exemplary instrument (1300) that may be used to treat a paranasal sinus drainage passageway (e.g., a frontal recess, a frontal sinus ostium, a maxillary sinus ostium, a sphenoid sinus ostium, etc.) or a Eustachian tube passageway. Instrument (1300) may incorporate any suitable combination of features described above. As best seen in FIG. 34, dilation catheter system (1300) includes a handle assembly (1350), a guide catheter (1304), a dilation catheter assembly (1340), and a guidewire (1306). As will be described in greater detail below, dilation catheter assembly (1340) and guidewire (1306) may actuate relative to handle assembly (1350) and guide catheter (1304) in order to position a distal end of guidewire (1306) and dilation catheter assembly (1340) in a desired position to treat a patient.

Handle assembly (1350) includes a body (1352) extending from an open proximal end (1360) to an open distal end (1362), a distal coupling assembly (1354), and a slidable pistol grip (1374). Pistol grip (1374) is slidably coupled with body (1352) via coupling protrusion (1375) and coupling channel (1378). Coupling protrusion (1375) may extend any suitable length along body (1352). Pistol grip (1374) may slide along protrusion and selectively fix to protrusion (1375) via a thumb screw (1376). In versions where coupling protrusion (1375) extends along a substantial portion of the length of body (1352), the operator may slide pistol grip (1374) to a desired position along the length of body (1352) and then manipulate thumb screw (1376) to secure the position of pistol grip (1374) along the length of body (1352). In any case, the operator may grasp pistol grip (1374) in order to control instrument (1300).

In some versions, the operator may remove pistol grip (1374) and simply grasp body (1352). For instance, when pistol grip (1374) is removed, body (1352) of handle assembly (1350) may be grasped like a pencil such that an operator may grasp instrument (1300) with a single hand. Body (1352) may include a textured gripping surface and/or other features in order to provide a sturdier grip. Other suitable ways in which body (1352) may be grasped will be apparent to those of ordinary skill in the art in view of the teachings herein. It should also be understood that coupling protrusion (1375) may be configured to receive various kinds of grips, such that the operator may select a preferred grip configuration and selectively secure the preferred grip to coupling protrusion (1375).

Body (1352) defines a longitudinal channel (1358) extending from open proximal end (1360) to open distal end (1362). Additionally, body (1352) has a slide deck (1364) defining a slide channel (1366) extending from open proximal end (1360) toward open distal end (1362). Slide Channel (1366) extends into adjacent portions of longitudinal channel (1358). Longitudinal channel (1358) is dimensioned to slidably house selected portions of dilation catheter assembly (1340) while slide deck (1364) and slide channel (1366) are dimensioned to slidably couple with an actuation assembly (1330) of dilation catheter assembly (1340).

Distal coupling assembly (1354) includes a button (1356) that may be pressed such that handle assembly (1350) may selectively couple with a proximal coupling portion (1302) of guide catheter (1304). Distal coupling assembly (1354) may include any suitable coupling features used to selectively attach with guide catheter (104) in instruments (600, 700) described above. Therefore, it should be understood that distal coupling assembly (1354) may selectively couple with guide catheter (1304) such that an operator may selectively rotate guide catheter (1304) to any desired rotational position around its own longitudinal axis relative to handle assembly (1350) and lock the selected rotational position.

Guide catheter (1304) includes proximal coupling portion (1302) and a removable distal tip (1316). Guide catheter (1304) may be substantially similar to guide catheter (104, 704, 1100) described above. Guide catheter (1304) defines an open distal end (1317) that extends all the way to proximal coupling portion (1302). Open distal end (1317) is dimensioned to slidably receive selective portions of dilation catheter assembly (1340).

In the current example, removable distal tip (1316) is rigid and straight.

However, it should be understood that removable distal tip (1316) may have any suitable rigid bend that would be apparent to one having ordinary skill in the art in view of the teachings herein. For example, removable distal tip (1316) may have a bend similar to guide tip (116) described above. In some versions, an operator may be presented with a kit having various distal tips (1316) that are each configured to facilitate access to a drainage passageway associated with different sinuses. For instance, one distal tip (1316) may be configured to facilitate access to a frontal recess; with another distal tip (1316) being configured to facilitate access to a maxillary sinus ostium; and with another distal tip (1316) being configured to facilitate access to a sphenoid sinus ostium. The operator may thus select and secure a particular distal tip (1316) based on the targeted anatomical structure. As yet another merely illustrative example, distal tip (1316) may be malleable rather than being rigid, such that the operator may selectively bend distal tip (1316) to a bend angle that facilitates access to a targeted anatomical structure.

The distal end of dilation catheter assembly (1340) includes an inflatable dilator (1310) that may be substantially similar to dilator (22) described above. The proximal end of dilation catheter assembly (1340) includes a proximal connector (1320) having a locking mechanism (1322), an injection port (1324), and an inflation port (1326). Shaft (1308) of dilation catheter assembly includes a first lumen (not shown) that provides fluid communication between inflation port (1326) and the interior of dilator (1310). An operator may inflate/deflate dilator (1310) similar to inflation of dilator (22) described above. Shaft (1308) also defines a second lumen (not shown) that extends from an open distal end of shaft (1308) to injection port (1324). This second lumen is configured to slidably receive guidewire (1306). The first and second lumens of shaft (1308) are fluidly isolated from each other. Thus, dilator (1310) may be selectively inflated and deflated by communicating fluid along the first lumen via inflation port (1326) while guidewire (1306) is positioned within the second lumen. Injection port (1324) and inflation port (1326) may be substantially similar to injection port (436) and inflation port (430) described above, respectively.

Locking mechanism (1322) may selectively lock guidewire (1306) within second lumen of shaft (1308) such that guidewire (1306) is selectively fixed to dilation catheter assembly (1340). Therefore guidewire (1306) may be inserted through injection port (1324) such a distal end of guidewire (1306) is positioned distally to open distal tip of shaft (1308), then guidewire (1306) may be locked into position utilizing locking mechanism (1322). Locking mechanism (1322) may have any suitable features of locking mechanism of instrument (300) described above. In some variations, locking mechanism (1322) is omitted, such that guidewire (1306) remains slidable relative to dilation catheter assembly (1340).

Dilation catheter assembly (1340) also includes actuation assembly (1330). As will be described in greater detail below, actuation assembly (1330) may selectively rotate, retract, and advance guide catheter assembly (1340) and guidewire (1306) relative to handle assembly (1350) and guide catheter (1304). Actuation assembly (1330) includes a rotating finger grip (1332), a distal rotary coupling (1334), a proximal rotary coupling (1336), and a slide body (1338). Slide body (1338) may slidably couple with body (1352) of handle assembly (1350) via slide deck (1364), slide channel (1366) and longitudinal channel (1358). An operator may insert slide body (1338) through slide channel (136) and longitudinal channel (1358) via open proximal end (1360). Therefore, slide body (1338) may be supported by slide deck (1364), but configured to slide relative handle assembly (1350).

Rotating finger grip (1332) is rotatably coupled to rotary couplings (1334, 1136) such that finger grip (1332) may rotate about its own longitudinal axis relative to slide body (1338). Slide body (1338) is coupled with shaft (1308) such that translation of slide body (1338) leads to translation of dilation catheter assembly (1340). Slide body (1338) is also coupled with shaft (1308) such that shaft (1308) may rotate about its own longitudinal axis relative to slide body (1338). Rotating finger grip (1332) is coupled with shaft (1308) such that rotation of finger grip (1332) about its own longitudinal axis leads to rotation of shaft (1308) about its own longitudinal axis. Rotating finger grip (1332) may be coupled with shaft (1308) through any suitable means as would be apparent to one having ordinary skill in the art in view of the teachings herein. By way of example only, rotating finger grip (1332) may be coupled with shaft (1308) in accordance with at least some of the teachings of U.S. patent application Ser. No. 15/278,588, entitled "Dilation Catheter Assembly with Rapid Change Components," filed Sep. 28, 2016, issued as U.S. Pat. No. 10,625,062 on Apr. 21, 2020, the disclosure of which is incorporated by reference herein.

It should be understood that an operator may actuate or rotate finger grip (1332) in order to actuate or rotate dilation catheter assembly (1340) relative to handle assembly (1350). In the present example, rotating finger grip (1332) is offset from shaft (1308) such their respective longitudinal axis spaced apart from each other. It should also be understood that an operator may actuate (i.e., longitudinally translate) finger grip (1332) and/or rotate finger grip (1332) using the same hand that grasps body (1352) and/or pistol grip (1374).

The portion (1312) of shaft (1308) that is distal of actuation assembly (1330) may be sufficiently stiff to be guided through the nasal cavity and into a Eustachian tube or into a drainage passageway associated with a paranasal sinus. In some versions, portion (1312) is formed of stainless steel, similar to portion (440) described above. The portion (1309) that is proximal of actuation assembly (1330) and the portion (1314) that is distal to portion (1312) may be more flexible than portion (1312). Therefore, portions (1314, 1109) may be substantially similar to portions (450, 438), respectively. Of course, any other suitable stiffness of portions (1312, 1114, 1109) may be used as would be apparent to one having ordinary skill in the art in view of the teachings herein.

Figure 41A:
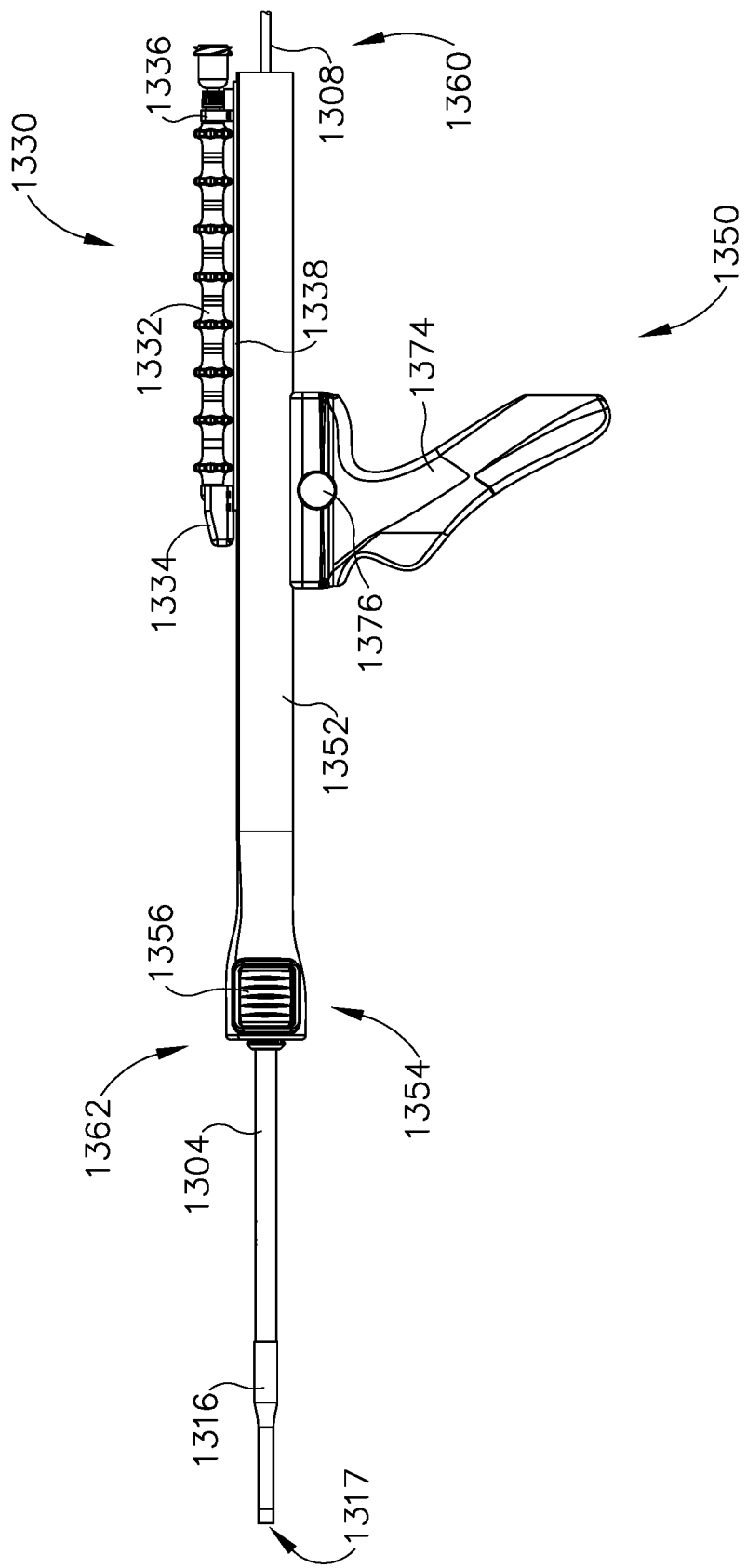
FIG. 41A depicts a side elevational view of the dilation catheter system of FIG. 36, where the actuation assembly, dilation catheter assembly, and guidewire are in a retracted position.

FIGS. 41A-41C show an exemplary use of instrument (1300). First, an operator may insert the distal end of guidewire (1306) through injection port (1324) and through second lumen of shaft (1308) until the distal end of guidewire (1306) extends through the open distal end of shaft (1308) a desired distance. The operator may then utilize locking mechanism (1322) in order to fix guidewire (1306) to shaft (1308). With guidewire (1306) coupled, the operator may place actuation assembly (1330) is in a retracted position, as shown in FIG. 41A, such that the distal end of guidewire (1306) is within dilation catheter (1304). The operator may advance instrument (1300) such that detachable tip (1316) and a distal portion of guide catheter (1304) are within a desired location of a patient.

In the present example, at the stage shown in FIG. 41A, dilation catheter assembly (1340) is in a proximal position during the positioning of detachable tip (1316) and a distal portion of guide catheter (1304) within a desired location in a patient, such that the distal portion of dilator catheter assembly (1340) is retracted within detachable tip (1316) and/or further proximally within guide catheter (1304). In addition, the distal end of guidewire (1306) is contained within guide catheter (1204) at the stage shown in FIG. 41A. In some other variations, the distal end of guidewire (1306) protrudes distally from the distal end of guide catheter (1304) during the positioning of detachable tip (1316) and a distal portion of guide catheter (1304) within a desired location in a patient, while the distal portion of dilator catheter assembly (1340) remains retracted within detachable tip (1316) and/or further proximally within guide catheter (1304)

Next, the operator may advance actuation assembly (1330) via finger grip (1332) such that guidewire (1306) and dilation catheter assembly (1340) distally pass detachable tip (1316) and dilator (1310) is in the desired location within a patient, as shown in FIG. 41B. Before and/or during advancement of instrument (1300), the operator may rotate guidewire (1306) and dilation catheter assembly (1340) via manipulation of finger grip (1332) as described above. This may promote entry of the distal end of guidewire (1306) into the targeted anatomical structure (e.g., sinus ostium, Eustachian tube, etc.). It should be understood that dilator (1310) is deflated at this point. Next, an operator may inflate dilator (1310) in order to dilate the targeted anatomical structure in the patient, as shown in FIG. 41C. When finished, an operator may deflate dilator (1310), as shown in FIG. 41B, then retract dilator (1310) and guidewire (1306) to the position shown in FIG. 41A, and finally remove guide catheter (1304) from the patient.

X. Exemplary Alternative Guide Catheters

It should be understood that the various guide catheters (30, 104, 704, 804, 1104, 1204, 1304) described herein may be constructed in numerous ways. For instance, in some versions, guide catheter (30, 104, 704, 804, 1104, 1204, 1304) comprises a straight proximal portion that is formed of metal (e.g., stainless steel, etc.); with a distal portion that is formed of a plastic material. In such versions, the plastic distal portion may include a preformed bend as described herein (and as described in various references cited herein) to facilitate access to particular anatomical structures (e.g., frontal recess, maxillary sinus ostium, sphenoid sinus ostium, etc.). In some other versions, guide catheter (30, 104, 704, 804, 1104, 1204, 1304) is formed entirely of metal (e.g., stainless steel, etc.). In such versions, the straight proximal portion and bent distal portion may comprise a homogenous continuum of metal, such that guide catheter (30, 104, 704, 804, 1104, 1204, 1304) is a monolithic construction from the straight proximal portion to the distal tip of the bent distal portion.

In versions where guide catheter (30, 104, 704, 804, 1104, 1204, 1304) is formed entirely of metal, the bent distal portion may be rigid. Also in versions where guide catheter (30, 104, 704, 804, 1104, 1204, 1304) is formed entirely of metal, the interior of guide catheter (30, 104, 704, 804, 1104, 1204, 1304) may include a coating (e.g., polytetrafluoroethylene, etc.), an insert, or some other feature that promotes smooth translation of a dilator and/or other component through the interior of guide catheter (30, 104, 704, 804, 1104, 1204, 1304). In addition, in versions where guide catheter (30, 104, 704, 804, 1104, 1204, 1304) is formed entirely of metal, the distal tip may be configured to be atraumatic, such that the distal tip does not damage tissue or other anatomical structures as guide catheter (30, 104, 704, 804, 1104, 1204, 1304) is being positioned in the patient. By way of example only, the distal tip may be rounded. In addition, or in the alternative, the distal tip may include a coating, overmold, or other feature to make the distal tip atraumatic.

In some instances, forming guide catheter (30, 104, 704, 804, 1104, 1204, 1304) entirely of metal will allow guide catheter (30, 104, 704, 804, 1104, 1204, 1304) to have a relatively larger inner diameter than a guide catheter (30, 104, 704, 804, 1104, 1204, 1304) that is formed of a combination of plastic and metal. In other words, in versions where guide catheter (30, 104, 704, 804, 1104, 1204, 1304) has a plastic distal portion, the plastic distal portion may need to have a smaller inner diameter due to wall thickness that is required to maintain a certain level of rigidity. By contrast, having the distal portion formed of metal may enable a thinner wall thickness without compromising rigidity; and the thinner wall thickness may in turn provide a larger inner diameter. The larger inner diameter may provide smoother translation of a dilator or other component through the interior of guide catheter (30, 104, 704, 804, 1104, 1204, 1304). In addition, versions of guide catheter (30, 104, 704, 804, 1104, 1204, 1304) that are formed entirely may be more reusable than guide catheters (30, 104, 704, 804, 1104, 1204, 1304) that are formed of a combination of metal and plastic. In particular, versions of guide catheter (30, 104, 704, 804, 1104, 1204, 1304) that are formed entirely may be more capable of withstanding sterilization processes between patients.

XI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A dilation catheter system, wherein the dilation catheter system comprises: (a) a body, wherein the body comprises a distal end and a proximal end; (b) a guidewire; (c) a dilation catheter, wherein the dilation catheter comprises an expandable dilator; (d) a guide catheter extending distally from the body, wherein the guide catheter is configured to receive the guidewire and the dilation catheter therethrough, wherein the guide catheter defines a longitudinal axis; (e) a cap secured to the guide catheter and the body, wherein the cap defines a chamber therein, and wherein the cap is movable relative to the body between a first longitudinal position and a second longitudinal position; and (f) a biasing member disposed in the chamber and configured to bias the cap toward the first longitudinal position.

Example 2

The dilation catheter system of Example 1, wherein the body comprises a first shoulder, a second shoulder, and a pocket defined therebetween, and wherein the cap comprises a cap shoulder disposed in the pocket.

Example 3

The dilation catheter system of Example 2, wherein the cap shoulder is configured to abut the second shoulder when the cap is in the first longitudinal position, and wherein the cap shoulder is configured to not abut the second shoulder when the cap is in the second longitudinal position.

Example 4

The dilation catheter system of Example 3, wherein the guide catheter is prevented from rotating about the longitudinal axis when the cap is in the first longitudinal position, and wherein the guide catheter is free to rotate about the longitudinal axis when the cap is in the second longitudinal position.

Example 5

A dilation catheter system, wherein the dilation catheter system comprises: (a) a body, wherein the body comprises a distal end and a proximal end; (b) a guidewire; (c) a dilation catheter, wherein the dilation catheter comprises an expandable dilator; (d) a locking mechanism, wherein the locking mechanism is configured to selectively lock the guidewire to the dilation catheter to form a fixed wire unit; and (e) an actuator, wherein the actuator is configured to translate relative to the body to thereby translate the fixed wire unit longitudinally relative to the body.

Example 6

The dilation catheter system of Example 5, further comprising a grip element, wherein the grip element is offset from the body and comprises a proximal neck and a distal neck, and wherein the actuator is disposed between the proximal neck and the distal neck Example 7

The dilation catheter system of Example 6, wherein the actuator is configured to move between the proximal neck and the distal neck.

Example 8

The dilation catheter system of any one or more of Examples 6 through 7, wherein the grip element comprises a plurality of grip features.

Example 9

The dilation catheter system of Example 8, wherein the plurality of grip features define an undulating surface.

Example 10

The dilation catheter system of any one or more of Examples 5 through 9, wherein the actuator further comprises a fixed wire unit rotation feature, wherein the fixed wire unit rotation feature is operable to rote the fixed wire unit relative to the body.

Example 11

A dilation catheter system, wherein the dilation catheter system comprises: (a) a body, wherein the body comprises a distal end and a proximal end; (b) a dilation catheter, wherein the dilation catheter comprises an expandable dilator and an elongate shaft; (c) a guidewire configured to move longitudinally within the elongate shaft; and (d) a locking mechanism configured to selectively prevent longitudinal movement of the guidewire within the elongate shaft.

Example 12

The dilation catheter system of Example 11, wherein the locking mechanism is configured to allow the guidewire to pass therethrough.

Example 13

The dilation catheter system of any one or more of Examples 11 through 12, wherein the locking mechanism comprises one of a luer style lock or a collet style lock.

Example 14

The dilation catheter system of any one or more of Examples 11 through 13, wherein the body further comprises a proximal connector, and wherein the locking mechanism is configured to abut the proximal connector when the guidewire is locked therein.

Example 15

A dilation catheter system, wherein the dilation catheter system comprises: (a) a body, wherein the body comprises a distal end and a proximal end; (b) a dilation catheter, wherein the dilation catheter comprises an expandable dilator and an elongate shaft; (c) a guidewire configured to move longitudinally within the elongate shaft; (d) an actuator secured to the elongate shaft; and (e) a locking mechanism coupled with the actuator and configured to selectively lock the dilation catheter to the guidewire and form a fixed wire unit.

Example 16

The dilation catheter system of Example 15, wherein the locking mechanism is configured to allow the guidewire to pass therethrough.

Example 17

The dilation catheter system of any one or more of Examples 15 through 16, wherein the locking mechanism comprises one of a luer style lock or a collet style lock.

Example 18

The dilation catheter of any one or more of Examples 15 through 17, wherein the dilation catheter system further comprises stabilizing tube disposed in the interior of elongate shaft and extending from actuator, wherein the stabilizing tube is configured to provide rigidity to an associated length of the guidewire.

Example 19

A dilation catheter system, wherein the dilation catheter system comprises: (a) a body, wherein the body comprises a distal end and a proximal end; (b) a guidewire; (c) a dilation catheter, wherein the dilation catheter comprises an expandable dilator; (d) a first actuator, wherein the first actuator is configured to translate relative to the body to thereby translate the guidewire longitudinally relative to the body; (e) a second actuator, wherein the second actuator is configured to translate relative to the body to thereby translate the dilation catheter longitudinally relative to the body; and (f) a grip ring extending from the body, wherein the ring defines an opening therein, wherein the body and the grip ring are configured to enable the body to be grasped using a pencil grip.

Example 20

The dilation catheter system of Example 19, wherein the body comprises an intermediate area disposed longitudinally between distal end and proximal end, and wherein the grip ring is extends from the intermediate area.

Example 21

The dilation catheter system of any one or more of Examples 19 through 20, wherein the body has a length defined by the distance between the proximal end and the distal end, and wherein the length is greater than 8.0 inches.

Example 22

The dilation catheter system of any one or more of Examples 19 through 21, wherein the body has a diameter of between 0.25 inches and 0.5 inches.

Example 23

A dilation catheter system, wherein the dilation catheter system comprises: (a) a body, wherein the body comprises a distal end and a proximal end; (b) a guidewire; (c) a dilation catheter, wherein the dilation catheter comprises an expandable dilator; and (d) an unitary actuation assembly, wherein the unitary actuation assembly is configured to translate and rotate relative to the body, wherein the guidewire and the dilation catheter are configured to translate and rotate relative to the body with the unitary actuation assembly, wherein the unitary actuation assembly comprises: (i) a sliding connector shaft, wherein the sliding connector shaft is rotatably and sliding housed within the body, and (ii) a control knob fixed to the sliding connector shaft.

Example 24

The dilation catheter system of Example 23, wherein the control knob comprises a longitudinal track, wherein the guidewire is configured to selectively fix to the longitudinal track.

Example 25

The dilation catheter system of Example 24, wherein the dilation catheter comprises a slit shaped opening, wherein the guidewire extends within the slit shaped opening.

Example 26

The dilation catheter system of Example 25, wherein the sliding connector shaft comprises a slit shaped opening, wherein the guidewire extends through the slit shaped opening toward the longitudinal track.

Example 27

The dilation catheter system of any one or more of Examples 23 through 26, wherein the control knob comprises a channel, wherein the channel is dimensioned for an interference fit with the dilation catheter.

Example 28

A dilation catheter system comprising: (a) a handle assembly comprising a body extending from a proximal end to a distal end; (b) a guide catheter configured to selectively couple with the handle assembly; (c) a dilation catheter assembly comprising: (i) a shaft defining an inflation lumen and an injection lumen, wherein the shaft comprises a port assembly located proximally relative to the proximal end of the handle assembly; (ii) a dilator coupled with the shaft, wherein the dilator is in fluid communication with the inflation lumen, wherein the injection lumen terminates into an open end distal in relation to the dilator, and (iii) an actuation member slidably attached to the handle; and (d) a guidewire slidably disposed within the port assembly and the injection lumen of the dilation catheter.

Example 29

The dilation catheter system of Example 28, wherein the handle assembly comprises a pistol grip extending from the body.

Example 30

The dilation catheter system of Example 29, wherein pistol grip is slidably coupled with the body.

Example 31

The dilation catheter system of any one or more of Examples 28 through 30, wherein the handle assembly further comprises a finger peg extending from the body.

Example 32

The dilation catheter system of any one or more of Examples 28 through 31, wherein the handle assembly defines a slot, wherein the actuation member is slidably disposed within the slot.

Example 33

The dilation catheter system of Example 32, wherein the actuation member is slidably connected with a portion of the body proximal in relation to the slot.

Example 34

The dilation catheter system of any one of more of Examples 28 through 33, further comprising a coupling assembly configured to rotationally lock the guide catheter with the body of the handle assembly, where in the coupling assembly is configured to allow the guide catheter to rotate relative to body before locking the guide catheter to the body.

Example 35

The dilation catheter system of Example 34, wherein the coupling assembly is configured to rotationally lock the guide catheter with the body independently from the angular position of the guide catheter relative to the body.

Example 36

The dilation catheter system of Example 35, wherein the coupling assembly comprises a cap attached to a proximal end of the guide catheter.

Example 37

The dilation catheter system of Example 36, wherein the cap is biased to rotationally lock the guide catheter relative to the body.

Example 38

The dilation catheter system of Example 37, wherein the coupling assembly further comprises a coil spring to bias the cap.

Example 39

The dilation catheter system of Example 37, wherein the coupling assembly further comprises a spring washer to bias the cap.

Example 40

The dilation catheter system of Example 37, wherein the coupling assembly further comprises a rubber bushing to bias the cap.

Example 41

The dilation catheter system of any one or more of Examples 28 through 40, wherein the shaft comprises a first portion proximal in relation to the actuation assembly, a second portion distal in relation to the actuation assembly, and a third portion distal in relation to the second portion, wherein the second portion is stiffer than the first portion and the third portion.

Example 42

The dilation catheter system of any one or more of Examples 28 through 41, further comprising a stabilizing tube mounted to the actuation assembly, wherein the guidewire extends through the stabilizing tube, wherein the stabilizing tube is configured to provide rigidity to an associated length of the guidewire.

Example 43

The dilation catheter system of any one or more of Examples 28 through 42, wherein the actuation assembly further comprises a finger grip, wherein the finger grip shares a longitudinal axis with the guidewire.

Example 44

The dilation catheter system of any one or more of Examples 28 through 43, wherein the actuation assembly further comprises a finger grip, wherein the finger grip is offset from the guidewire such that the guidewire and the finger grip do not share a longitudinal axis.

Example 45

The dilation catheter system of any one or more of Examples 28 through 44, wherein the guide catheter comprises a straight proximal portion and a bent distal portion, wherein the straight proximal portion and the bent distal portion cooperate to define a first length, wherein the entire first length of the guide catheter is formed of a metallic material.

Example 46

A dilation catheter system, wherein the dilation catheter system comprises: (a) a body, wherein the body comprises a distal end and a proximal end; (b) a guidewire; (c) a dilation catheter, wherein the dilation catheter comprises an expandable dilator; (d) a guide catheter extending distally from the body, wherein the guide catheter is configured to receive the guidewire and the dilation catheter therethrough, wherein the guide catheter defines a longitudinal axis; (e) a cap secured to the guide catheter and the body, wherein the cap defines a chamber therein, and wherein the cap is movable relative to the body between a first longitudinal position and a second longitudinal position, wherein the cap is configured to lock an angular position of the guide catheter relative to the body when the guide catheter is in the first longitudinal position, wherein the cap is configured to unlock the angular position of the guide catheter relative to the body when the guide catheter is in the second longitudinal position; and (f) a biasing member disposed in the chamber and configured to bias the cap toward the first longitudinal position.

Example 47

A dilation catheter system, wherein the dilation catheter system comprises (a) a handle assembly comprising a body extending from a proximal end to a distal end; (b) a guide catheter configured to selectively couple with the handle assembly; (c) a dilation catheter assembly comprising: (i) a shaft defining an inflation lumen and an injection lumen, (ii) a dilator coupled with the shaft, wherein the dilator is in fluid communication with the inflation lumen, wherein the injection lumen terminates into an open end distal in relation to the dilator, (iii) an actuation member slidably attached to the handle, and (iv) a coupling port attached to a proximal end of the shaft, wherein the coupling port has a first connection in communication with the inflation lumen and a second connection in communication with the injection lumen; and (d) a guidewire slidably disposed within the injection lumen of the dilation catheter via the second connection.

Example 48

The dilation catheter system of Example 47, wherein the actuation member is configured to rotate the shaft.

XII. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A dilation catheter system comprising:
 (a) a handle assembly comprising a body extending from a proximal end to a distal end;
 (b) a guide catheter; and
 (c) a dilation catheter assembly comprising:
  a shaft defining an inflation lumen and an injection lumen, wherein the shaft comprises a port assembly located proximally relative to the proximal end of the handle assembly,
  (ii) a dilator coupled with the shaft, wherein the dilator is in fluid communication with the inflation lumen, wherein the injection lumen terminates into an open end distal in relation to the dilator, and
  (iii) an actuation member slidably attached to the handle;
 (d) a guidewire slidably disposed within the port assembly and the injection lumen of the dilation catheter;
 wherein the actuation member further comprises a locking assembly, wherein the locking assembly is configured to selectively fix the guidewire with the shaft of the dilation catheter assembly such that the guidewire and the shaft actuate relative to the handle unitarily with the actuation member.

2. The dilation catheter system of claim 1, wherein the handle assembly comprises a pistol grip extending from the body.

3. The dilation catheter system of claim 2, wherein the pistol grip is slidably coupled with the body.

4. The dilation catheter system of claim 1, wherein the handle assembly further comprises a finger peg extending from the body.

5. The dilation catheter system of claim 1, wherein the handle assembly defines a slot, wherein the actuation member is slidably disposed within the slot.

6. The dilation catheter system of claim 5, wherein the actuation member is slidably connected with a portion of the body proximal in relation to the slot.

7. The dilation catheter system of claim 1, further comprising a coupling assembly configured to rotationally lock the guide catheter with the body of the handle assembly, wherein the coupling assembly is configured to allow the guide catheter to rotate relative to the body before locking the guide catheter to the body.

8. The dilation catheter system of claim 7, wherein the coupling assembly is configured to rotationally lock the guide catheter with the body independently from the angular position of the guide catheter relative to the body.

9. The dilation catheter system of claim 8, wherein the coupling assembly comprises a cap attached to a proximal end of the guide catheter, wherein the cap is biased to rotationally lock the guide catheter relative to the body.

10. The dilation catheter system of claim 9, wherein the coupling assembly further comprises a coil spring to bias the cap.

11. The dilation catheter system of claim 9, wherein the coupling assembly further comprises a spring washer to bias the cap.

12. The dilation catheter system of claim 9, wherein the coupling assembly further comprises a rubber bushing to bias the cap.

13. The dilation catheter assembly of claim 1, wherein the guide catheter comprises a straight proximal portion and a bent distal portion, wherein the straight proximal portion and the bent distal portion cooperate to define a first length, wherein the entire first length of the guide catheter is formed of a metallic material.

14. The dilation catheter system of claim 1, wherein the shaft comprises a first portion proximal in relation to the actuation assembly, a second portion distal in relation to the actuation assembly, and a third portion distal in relation to the second portion, wherein the second portion is stiffer than the first portion and the third portion.

15. The dilation catheter system of claim 1, further comprising a stabilizing tube mounted to the actuation assembly, wherein the guidewire extends through the stabilizing tube, wherein the stabilizing tube is configured to provide rigidity to an associated length of the guidewire.

16. The dilation catheter system of claim 1, wherein the actuation assembly further comprises a finger grip, wherein the finger grip shares a longitudinal axis with the guidewire.

17. The dilation catheter system of claim 1, wherein the actuation assembly further comprises a finger grip, wherein the finger grip is offset from the guidewire such that the guidewire and the finger grip do not share a longitudinal axis.

18. The dilation catheter system of claim 1, wherein the locking assembly comprises a central channel and a plurality of longitudinal tracks extending on an outer surface of the actuation assembly, wherein the central channel is configured to couple with the shaft, wherein the plurality of longitudinal tracks are configured to couple with the guidewire.

19. A dilation catheter system comprising:
(a) a handle assembly comprising a body extending from a proximal end to a distal end;
(b) a guide catheter;
(c) a dilation catheter assembly comprising:
  (i) a shaft defining an inflation lumen and an injection lumen, wherein the shaft comprises a port assembly located proximally relative to the proximal end of the handle assembly;
  (ii) a dilator coupled with the shaft, wherein the dilator is in fluid communication with the inflation lumen, wherein the injection lumen terminates into an open end distal in relation to the dilator,
  (iii) an actuation member slidably attached to the handle, wherein the actuation member defines a central channel, wherein the actuation member comprises a plurality of longitudinal tracks extending on an outer surface of the actuation member, wherein the central channel is configured to couple with the shaft; and
(d) a guidewire slidably disposed within the port assembly and the injection lumen of the dilation catheter, wherein the plurality of longitudinal tracks are configured to couple with the guidewire such that the actuation member and the guidewire actuate relative to the handle unitarily.

20. A dilation catheter system comprising:
(a) a handle assembly comprising a body extending from a proximal end to a distal end;
(b) a guide catheter configured to selectively couple with the handle assembly, wherein a proximal portion of the guide catheter extends along a longitudinal axis;
(c) a dilation catheter assembly comprising:
  (i) a shaft defining an inflation lumen and an injection lumen, wherein the shaft comprises a port assembly located proximally relative to the proximal end of the handle assembly;
  (ii) a dilator coupled with the shaft, wherein the dilator is in fluid communication with the inflation lumen, wherein the injection lumen terminates into an open end distal in relation to the dilator, and
  (iii) an actuation member slidably attached to the handle;
(d) a guidewire slidably disposed within the port assembly and the injection lumen of the dilation catheter; and
(e) a guide catheter locking assembly, wherein the guide catheter locking assembly is configured to transition between a locked position and an unlocked position, wherein the guide catheter is configured to rotate about its own longitudinal axis relative to the handle assembly into any angular position when the guide catheter locking assembly is in the unlocked position, wherein the guide catheter locking assembly is configured to fix the guide catheter relative to handle assembly in the locked position while the guide catheter is in any angular position relative to the handle assembly.

* * * * *